United States Patent
Vanmaele et al.

(10) Patent No.: US 7,355,044 B2
(45) Date of Patent: *Apr. 8, 2008

(54) SELF-ASSEMBLING DYES

(75) Inventors: Luc Vanmaele, Lochristi (BE); Johan Loccufier, Zwijnaarde (BE); Egbert Meijer, Waalre (NL); Henricus Janssen, Eindhoven (NL); Pieter Fransen, Boxtel (NL)

(73) Assignee: Agfa-Gevaert N.V., Mortsel (BE)

( * ) Notice: Subject to any disclaimer, the term of this patent is extended or adjusted under 35 U.S.C. 154(b) by 498 days.

This patent is subject to a terminal disclaimer.

(21) Appl. No.: 10/844,099

(22) Filed: May 12, 2004

(65) Prior Publication Data

US 2005/0051052 A1    Mar. 10, 2005

Related U.S. Application Data

(63) Continuation-in-part of application No. 10/266,297, filed on Oct. 8, 2002, now abandoned.

(60) Provisional application No. 60/336,310, filed on Oct. 31, 2001.

(30) Foreign Application Priority Data

Oct. 25, 2001    (EP)    ................... 01000574

(51) Int. Cl.
 *C07D 239/36*    (2006.01)
 *C09D 11/00*    (2006.01)

(52) U.S. Cl. .................. 544/320; 544/321; 106/31.27; 106/31.43; 106/31.47; 106/31.58

(58) Field of Classification Search ............... 544/320, 544/321
See application file for complete search history.

(56) References Cited

U.S. PATENT DOCUMENTS 3,889,271 A    6/1975    Freytag et al. ................ 346/1

2002/0149656 A1    10/2002    Nohr et al. ................... 347/95
2003/0021983 A1    1/2003    Nohr et al. ................. 428/327
2004/0045477 A1    3/2004    Andrievsky .............. 106/31.27
2004/0050290 A1    3/2004    Andrievsky .............. 106/31.27

OTHER PUBLICATIONS

Dyer et al., CAPLUS Abstract 57:29647, 1962.*
Reiser et al., CAPLUS Abstract 115:250186, 1991.*
Armstrong et al., CAPLUS Abstract 136:199910, 2001.*
Mougin et al., CAPLUS Abstract 138:28948, 2002.*
Derwent ACC No. 2004-125942, 200428, Agfa-Gevaert, JP2003206424 Jul. 22, 2003.

* cited by examiner

*Primary Examiner*—Deepak Rao
(74) *Attorney, Agent, or Firm*—Joseph T. Guy; Nexsen Pruet, LLC

(57) ABSTRACT

A novel dye according to formula (I):

Formula (I)

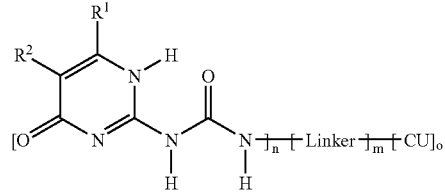

capable of self-assembling thus forming supra-molecular structures. These self-assembling dyes may be advantageously used in an ink-jet ink for improving the stability of ink-jet ink images to light fading.

7 Claims, No Drawings

SELF-ASSEMBLING DYES

CROSS-REFERENCE TO RELATED PATENT APPLICATIONS

This application is a continuation-in-part of application Ser. No. 10/266,297, filed Oct. 8, 2002 now abandoned, which claims the benefit of U.S. Provisional Application No. 60/336,310 filed Oct. 31, 2001, which is incorporated by reference. In addition, this application claims the benefit of European Application No. 01000574.2 filed Oct. 25, 2001, which is also incorporated by reference.

FIELD OF THE INVENTION

The present invention relates to a particular type of novel dye. It further relates to ink-jet compositions and ink-jet printing processes using these dyes, and to an ink-jet printing apparatus provided with an ink cartridge containing such a dye.

BACKGROUND OF THE INVENTION

In the majority of applications printing proceeds by pressure contact of an ink-laden printing form with an ink-receiving material which is usually plain paper. The most frequently used impact printing technique is known as lithographic printing based on the selective acceptance of oleophilic ink on a suitable receptor.

In recent times however so-called non-impact printing systems have replaced classical pressure-contact printing to some extent for specific applications. A survey is given e.g. in the book "Principles of Non Impact Printing" by Jerome L. Johnson (1986), Palatino Press, Irvine, Calif. 92715, USA.

Among non-impact printing techniques ink-jet printing has become a popular technique because of its simplicity, convenience and low cost. Especially in those instances where a limited edition of the printed matter is needed, ink-jet printing has become a technology of choice. A recent survey on progress and trends in ink-jet printing technology is given by Hue P. Le in *Journal of Imaging Science and Technology* Vol. 42 (1), January/February 1998.

In ink-jet printing tiny drops of ink fluid are projected directly onto an ink-receiver surface without physical contact between the printing device and the ink-receiver. The printing device stores the printing data electronically and controls a mechanism for ejecting the ink drops image-wise onto the ink-receiver. Printing can be accomplished by moving a print head across the ink-receiver or vice versa. Early patents on ink-jet printers include U.S. Pat. Nos. 3,739,393, 3,805,273 and 3,891,121.

The jetting of the ink droplets can be performed in several different ways. In a first type of process called continuous ink-jet printing, the ink stream jetted from an orifice of the print head is broken up, by applying a pressure wave pattern to this orifice, into ink droplets of uniform size and spacing. When the jet break-up mechanism is controlled, an electric charge can be applied to the droplets selectively and reliably as they form from the continuous ink stream. The charged drops passing through an electric field are deflected into a gutter for recuperation, while the uncharged drops proceed directly onto the ink-receiver to form an image or vice versa.

According to a second process the ink droplets can be created by a "drop on demand" method (DOD). A drop-on-demand device ejects ink droplets only when they are needed for imaging on the ink-receiver, thereby avoiding the complexity of drop charging, deflection hardware, and ink collection. In drop-on-demand ink-jet printing, the ink droplet can be formed by means of a pressure wave created by the mechanical motion of a piezoelectric transducer (so-called "piezo method"), or by means of discrete thermal pulses (so-called "bubble jet" method, or "thermal jet" method).

Ink receiving layers for ink-jet recording media are either non-absorptive or absorptive. In absorptive ink-receiving layers the ink is either absorbed by swelling of the layer due to the specific polymers present in the layer, or is absorbed by capillarity, due to the microporous character of the layer.

It is known that the ink-receiving layers in ink-jet recording elements must meet different stringent requirements:

the ink-receiving layer should have a high ink absorbing capacity, so that the dots will not flow out and will not increase in size more than is necessary to obtain a high optical density;

the ink-receiving layer should have a high ink absorbing speed (short ink drying time) so that the ink-droplets will not feather if touched immediately after application;

the ink dots that are applied to the ink-receiving layer should be substantially round in shape and smooth at their peripheries. The dot diameter must be constant and accurately controlled;

the receiving layer must be readily wetted so that there is no "puddling", i.e. coalescence of adjacent ink dots, and an previously absorbed ink drop should not show any "bleeding", i.e. overlap with neighbouring or later placed dots;

transparent ink-jet recording elements must have a low haze-value and exhibit excellent transmittance properties;

after being printed the image must have a good resistance regarding water-fastness, light-fastness, and be stable to extreme conditions of temperature and humidity;

the ink-jet recording material must not show any curl or sticky behavior if stacked before or after being printed;

the ink-jet recording element must be able to move smoothly through different types of printers.

All these properties are often in a trade-off relationship with one another, as it is difficult to satisfy them all at the same time.

It will be readily understood that the optimal composition of an ink is dependent on the ink-jetting method used and on the nature of the ink-receiver to be printed.

Ink compositions for ink-jet typically include the following ingredients: dyes or pigments, water and/or organic solvents, humectants such as glycols, detergents, thickeners, polymeric binders, preservatives, etc.

Ink compositions can be roughly divided into:

water based, the drying mechanism involving absorption, penetration and evaporation;

oil based, the drying involving absorption and penetration;

solvent based, the drying mechanism involving primarily evaporation;

hot melt or phase change, in which the ink is liquid at the ejection temperature but solid at room temperature and wherein drying is replaced by solidification;

UV-curable, in which drying is replaced by polymerization.

It is also known that dyes used in inks for ink-jet printing must meet different stringent requirements. For example they are required to provide sharp, non-feathered images having good water-fastness, solvent fastness, light-fastness and optical density. Their solubility must be fine-tuned to the vehicle they are dissolved in. Preferably they have high molecular extinction coefficients. In spite of the many dyes that already exist for application in ink-jet inks, there is still a continuous search for novel dyes and especially for dyes with an improved light-fastness and stability towards (singlet)oxygen, ozone and air pollutants such as sulfur oxides (SOx) and nitrogen oxides (NOx).

OBJECTS OF THE INVENTION

It is an object of the present invention to provide novel dyes for producing ink-jet images exhibiting improved light-fastness.

Further objects of the invention will become clear from the detailed description hereinafter.

SUMMARY OF THE INVENTION

It has been surprisingly found that the use of self-assembling dyes results in a substantial improvement in the stability of ink-jet ink images to light fading.

Objects of the present invention are realized by providing a self-assembling dye according to formula (I):

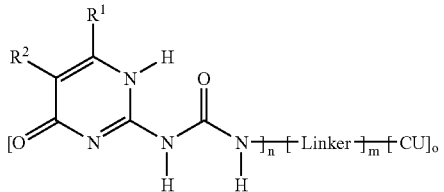

Formula (I)

wherein

Linker represents any linking group containing at least one carbon, nitrogen, silicon, phosphorous, sulfur or oxygen atom;

CU means any chromophore group with an absorption maximum between 200 nm and 2000 nm.

n and o are the same or different and are integers having a value of at least 1; m can be zero or any integer having a value of at least 1;

$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a chromophore group, or $R^1$ and $R^2$ represent the necessary atoms to form a ring system.

DETAILED DESCRIPTION OF THE INVENTION

Definitions

The term "self-assembly" as used in disclosing the present invention means the method of association in which individual molecules spontaneously associate upon Brownian movement in a solvent or gas phase until a stable structure of minimum energy is formed by means of hydrogen bonding.

The abbreviation "SAU" is used for Self-Assembling Unit, which is a part of a molecular structure capable of self-assembly by forming at least three hydrogen bonds.

The term "chromophore group" as used in disclosing the present invention means a part of a molecular structure capable of absorbing light from the visible spectrum and imparting color to other materials, e.g. an ink-jet ink or an ink-jet receiver. The abbreviation "CU" is used for chromophore group.

The term "self-assembling dye" as used in disclosing the present invention means a dye comprising in its molecular structure covalently bonded to each other in any manner at least one SAU and at least one chromophore group, CU.

The term "dye system" as used in disclosing the present invention means a self-assembled structure consisting of one or more self-assembling dyes and/or self-assembling non-dye compounds.

The term "reference dye" as used in disclosing the present invention means a dye that contains no SAU.

The term "ink vehicle" and "vehicle" as used in disclosing the present invention means a medium for dissolving the self-assembling dye, e.g. water, an organic solvent or an oil.

The term "alkyl" as used in disclosing the present invention means all variants possible for each number of carbon atoms in the alkyl group i.e. for three carbon atoms: n-propyl and isopropyl; for four carbon atoms: n-butyl, isobutyl and tertiary-butyl; for five carbon atoms: n-pentyl, 1,1-dimethyl-propyl, 2,2-dimethylpropyl and 2-methyl-butyl etc.

The term "acyl group" as used in disclosing the present invention means —(C=O)-aryl and —(C=O)-alkyl groups.

The term "saturated aliphatic group" as used in disclosing the present invention means saturated straight chain, branched chain and alicyclic hydrocarbon groups.

The term "unsaturated aliphatic group" as used in disclosing the present invention means straight chain, branched chain and alicyclic hydrocarbon groups which contain at least one double or triple bond.

The term "aromatic group" as used in disclosing the present invention means a covalently bonded assemblage of cyclic conjugated carbon atoms, which are characterized by large resonance energies, e.g. benzene, naphthalene and anthracene.

The term "alicyclic hydrocarbon group" means a covalently bonded assemblage of cyclic conjugated carbon atoms, which do not form an aromatic group, e.g. cyclohexane.

The term "substituted" as used in disclosing this invention means that one or more of the carbon atoms and/or that a hydrogen atom of one or more of the carbon atoms in an aliphatic group, an aromatic group or an alicyclic hydrocarbon group, are replaced by an oxygen atom, a nitrogen atom, a phosphorous atom, a silicon atom, a sulfur atom, a selenium atom or a tellurium atom, or a group containing one or more of these said carbon and hydrogen replacing atoms. Such substituents include hydroxyl groups, thiol groups, carbamate groups, urea groups, ether groups, thio-ether groups, carboxylic acid groups, ester groups, sulphonate groups, sulphonamide groups, phosphonate groups, phosphonamide groups, phosphonamidate groups, amide groups and amine groups.

The term "heteroaromatic group" means an aromatic group wherein at least one of the cyclic conjugated carbon atoms is replaced by a nitrogen atom or a phosphorous atom.

The term "heterocyclic group" means an alicyclic hydrocarbon group wherein at least one of the cyclic conjugated carbon atoms is replaced by an oxygen atom, a nitrogen atom, a phosphorous atom, a silicon atom, a sulfur atom, a selenium atom or a tellurium atom Self-assembling Dyes Objects of the present invention are realized with a self-assembling dye according to formula (I):

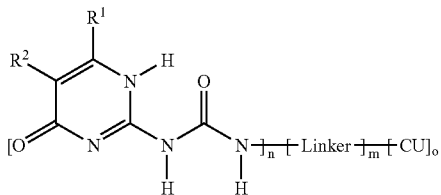

Formula (I)

wherein

Linker represents any linking group containing at least one carbon, nitrogen, silicon, phosphorous, sulfur or oxygen atom;

CU means any chromophore group with an absorption maximum between 200 nm and 2000 nm.

n and o are the same or different and are integers having a value of at least 1; m can be zero or any integer having a value of at least 1;

$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a chromophore group, or $R^1$ and $R^2$ represent the necessary atoms to form a ring system.

The Linker is preferably selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

Preferably n and o are integers independently selected from the range 1 to 100, more preferably integers selected from the range 1 to 10, and particularly preferably integers selected from the range 1 to 5. Preferably m is an integer selected from the range 1 to 10, and particularly preferably selected from the range 1 to 5.

CU means any chromophore group with an absorption maximum between 200 nm and 2000 nm. Preferred chromophore groups are those that absorb light between 300 nm and 1200 nm. Most preferred are chromophore groups absorbing light between 380 nm and 850 nm.

The nature of the vehicle used in the composition or ink-jet ink to be formulated will determine the nature of the functional groups to be incorporated into the CU-fragment. This is different for water based, oil based, solvent based, UV-curable or hot melt inks.

The present invention is not limited to any type of CU-fragment and any dye provided with the necessary reactive group(s) can be used for the CU-fragment. They may be of any chemical class such as azo dyes, anthraquinone dyes, (poly)methine dyes, azomethine dyes, disazo dyes, carbonium dyes, polyene dyes, pyrene dyes, styryl dyes, stilbene dyes, phthalocyanine dyes, coumarin dyes, aryl-carbonium dyes, nitro dyes, naphtholactam dyes, dioxazine dyes, formazan dyes, flavin dyes, etc. Suitable examples include dyes mentioned in:

The Colour Index International

Organic Chemistry in Colour, P. F. Gordon, P. Gregory

Color Chemistry, Heinrich Zollinger, Second revised edition

Colour Chemistry, The design and synthesis of organic dyes and pigments, A. T. Peters, H. S. Freeman Advances in Color Chemistry Series, Volume 3; Modern Colourants, Synthesis and Structure, A. T. Peters, H. S. Freeman Organic Colorants, A Handbook of Data of Selected Dyes for Electro-Optical Applications, M. Okawara, T. Kitao, T. Hirashima, M. Matsuoka Studies in Organic Chemistry 40, Photochromism, Molecules and Systems, Heinz Dürr and in the following U.S. Pat. Nos: 5,510,225, 5,422,334, 5,122,499, 5,571,765, 5,169,828, 5,589,316, 5,366,951, 5,324,601, 5,514,638, 5,455,218, 5,420,097, 5,432,040, 5,665,677, 5,116,806, 5,391,536, 5,314,860, 5,438,030, 5,026,677, 5,397,762, 5,324,621, 5,326,666, 5,043,316, 4,987,119, 5,565,403, 5,021,393, 5,082,823, 5,246,908, 5,326,676, 5,518,984, 4,985,395, 5,356,857, 5,547,815, 5,476,935, 5,084,432, 5,595,574, 5,753,352, 5,468,258, 5,514,516, 5,698,364, 5,489,568, 5,468,870, 5,514,819, 5,571,289, 5,037,731, 5,229,353, 5,371,228, 5,463,045, 5,587,268, 5,616,697, 5,142,089, 5,328,887, 5,438,122

Preferably the chromophore group CU of the self-assembling dye, according to the present invention, is a dye selected from the group consisting of an azo dye with a molar extinction coefficient larger than $10^3$ l.mol$^{-1}$.cm$^{-1}$, an anthraquinone dye, a (poly)methine dye, an azomethine dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye.

Preferably the Linker of the self-assembling dye, according to the present invention, is selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

Preferably the Linker of the self-assembling dye, according to the present invention, incorporates at least one group selected from the group consisting of urea, sulfonate, sulfonamide, carbamate, phosphonamide and phosphoramide groups.

The self-assembling dyes according to the present invention can be prepared using synthetic methods known to those who are skilled in the art of organic synthesis. By way of example the synthesis of several dyes according to the present invention is described in the Examples.

Suitable examples of self-assembling dyes according to the present invention are shown in Table 1.

TABLE 1
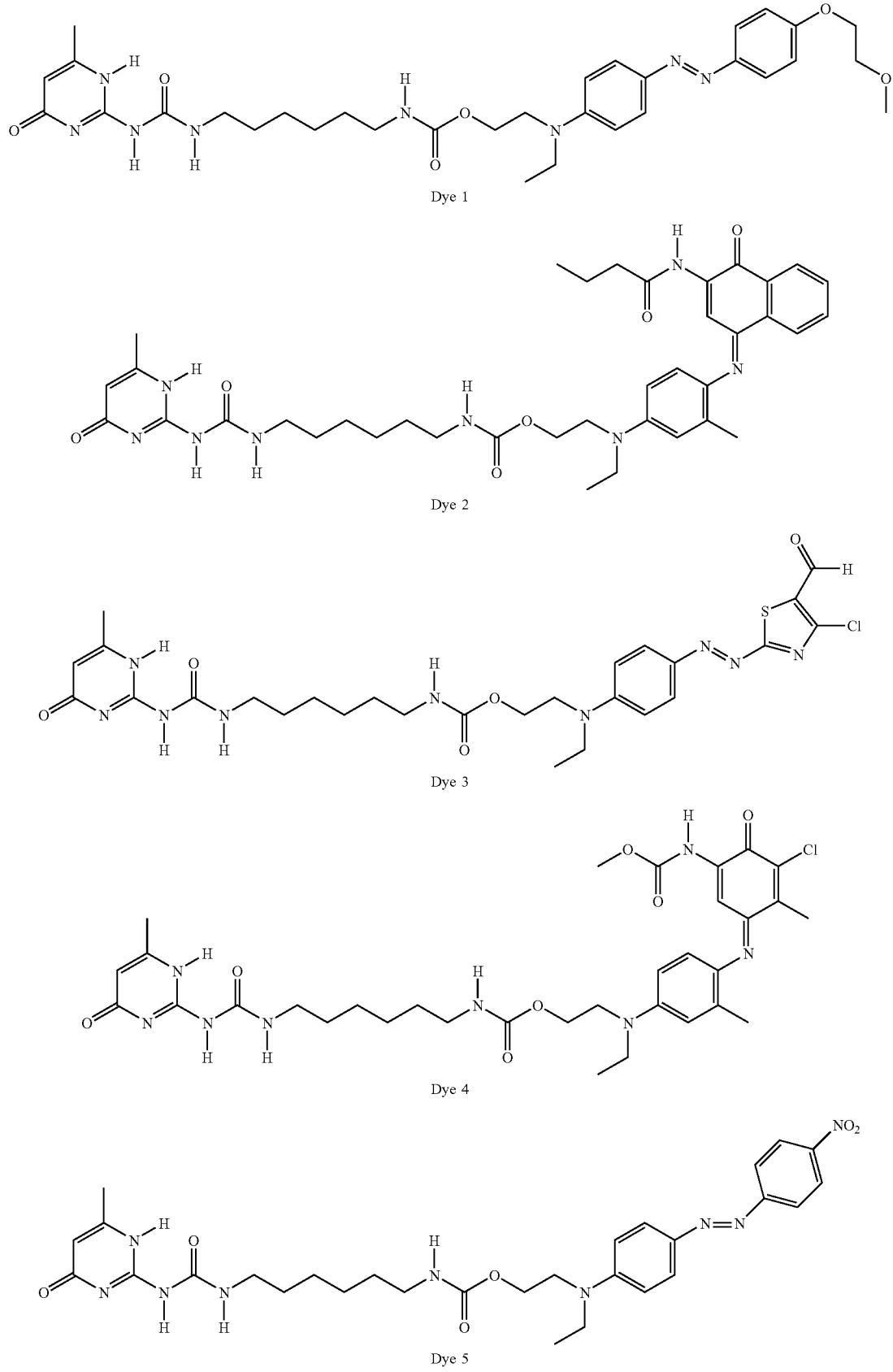

TABLE 1-continued
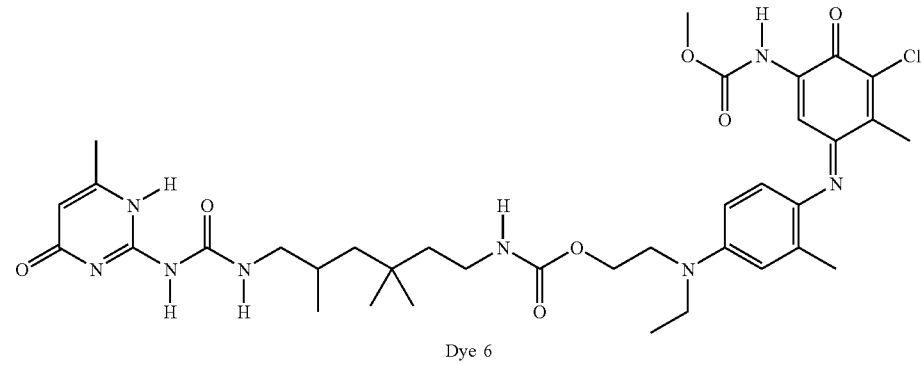
Dye 6
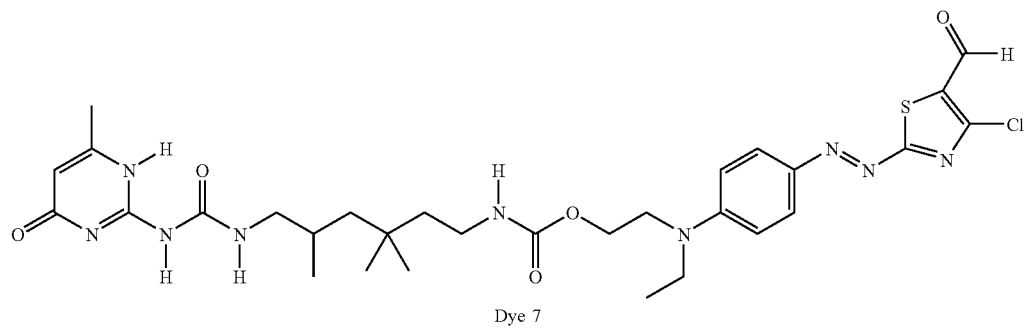
Dye 7
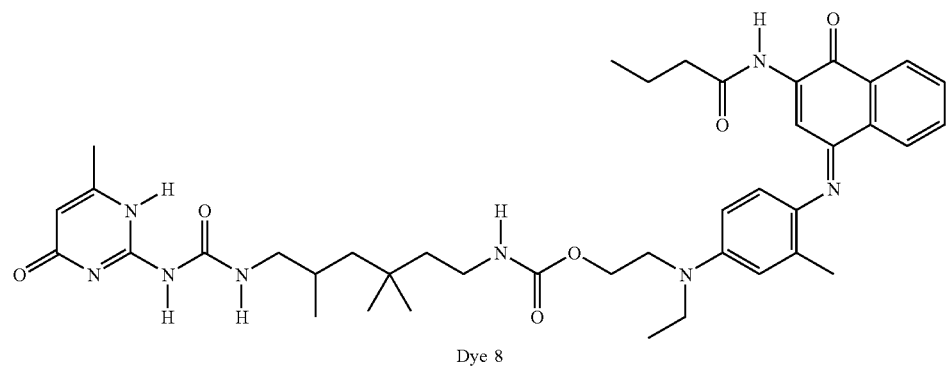
Dye 8
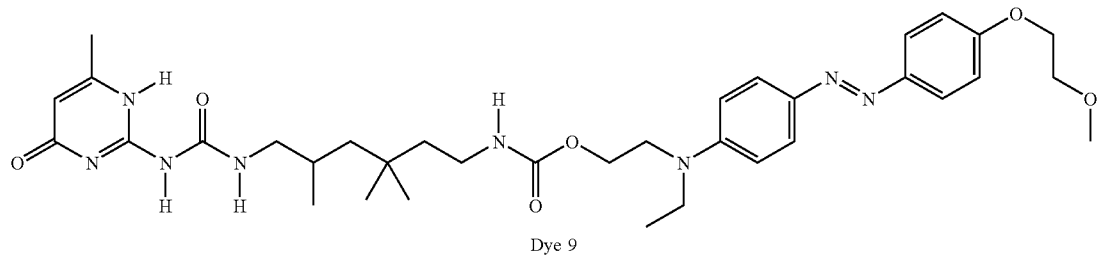
Dye 9

TABLE 1-continued
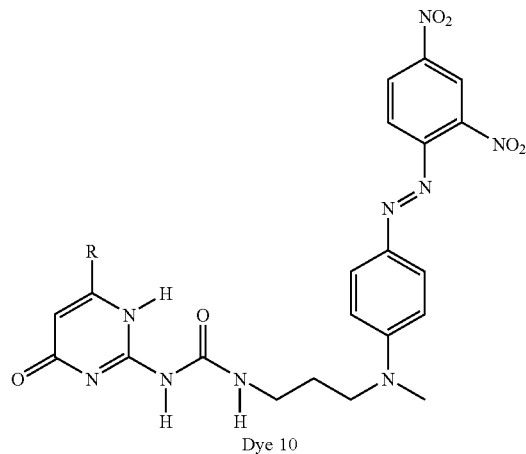
Dye 10
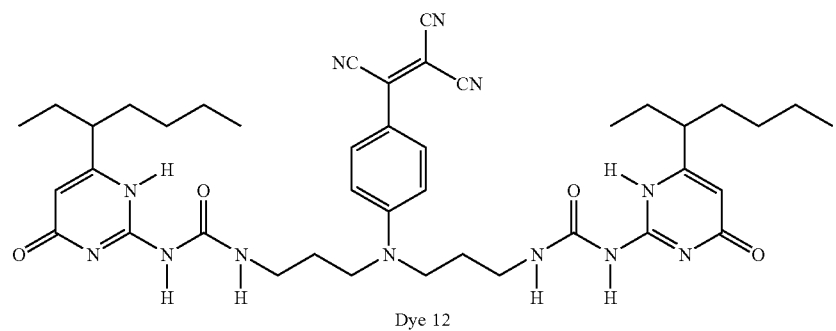
Dye 12
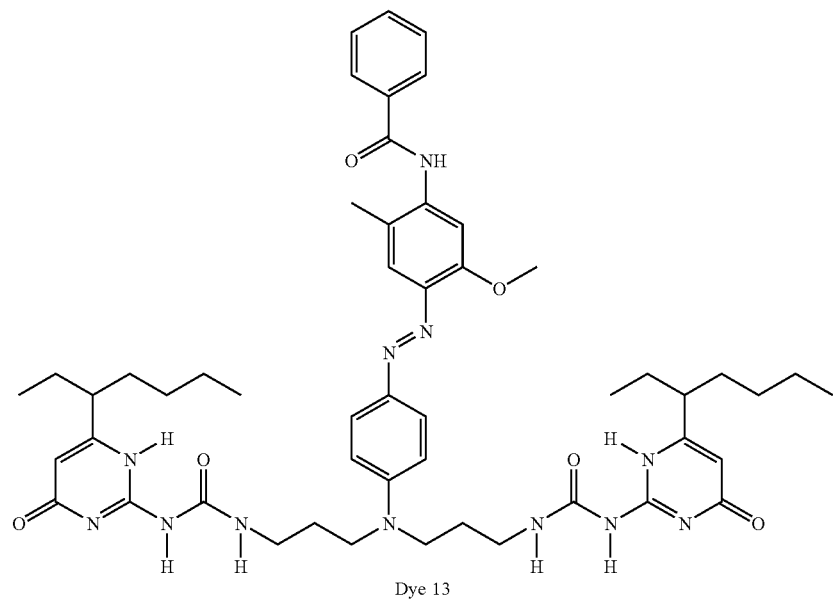
Dye 13

TABLE 1-continued
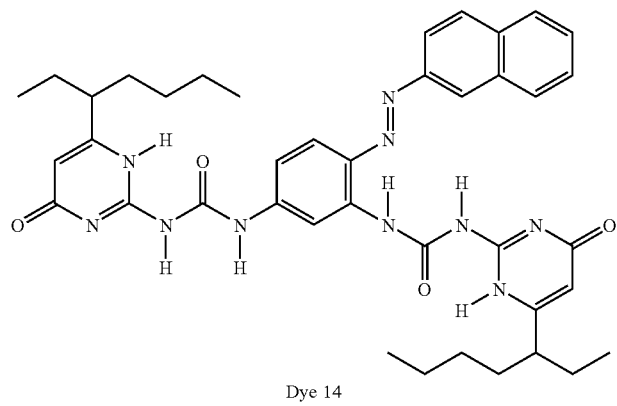
Dye 14
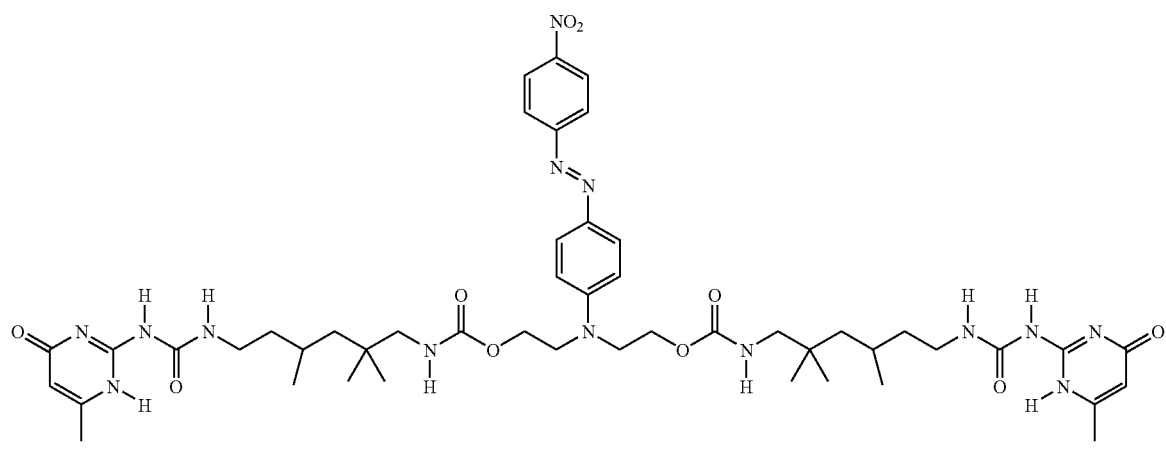
Dye 15
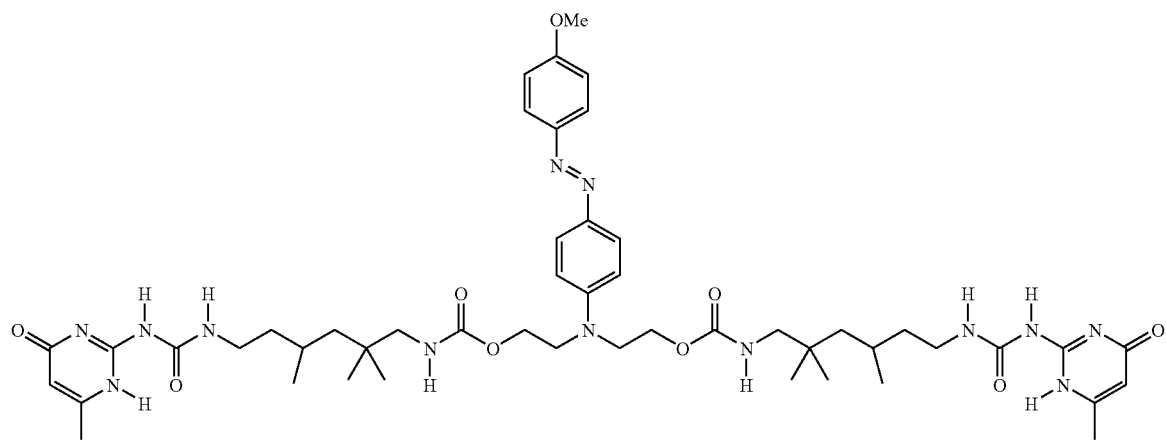
Dye 16
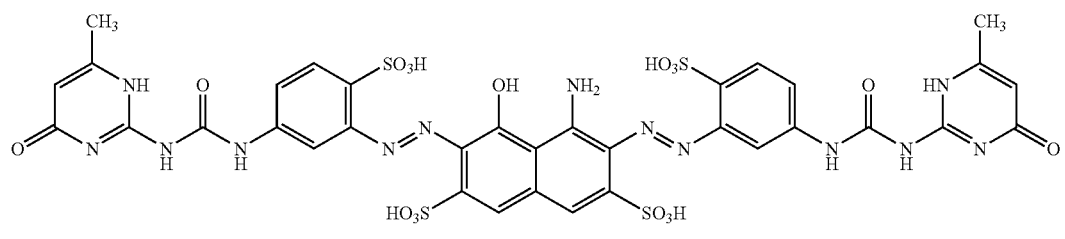
Dye 17

TABLE 1-continued
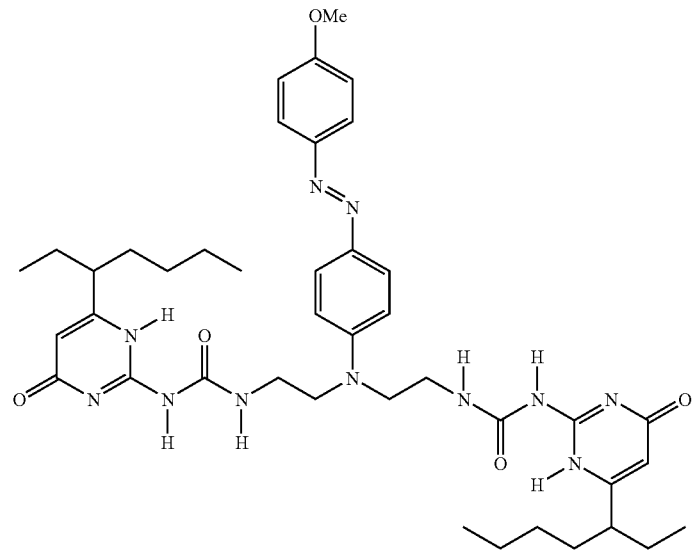
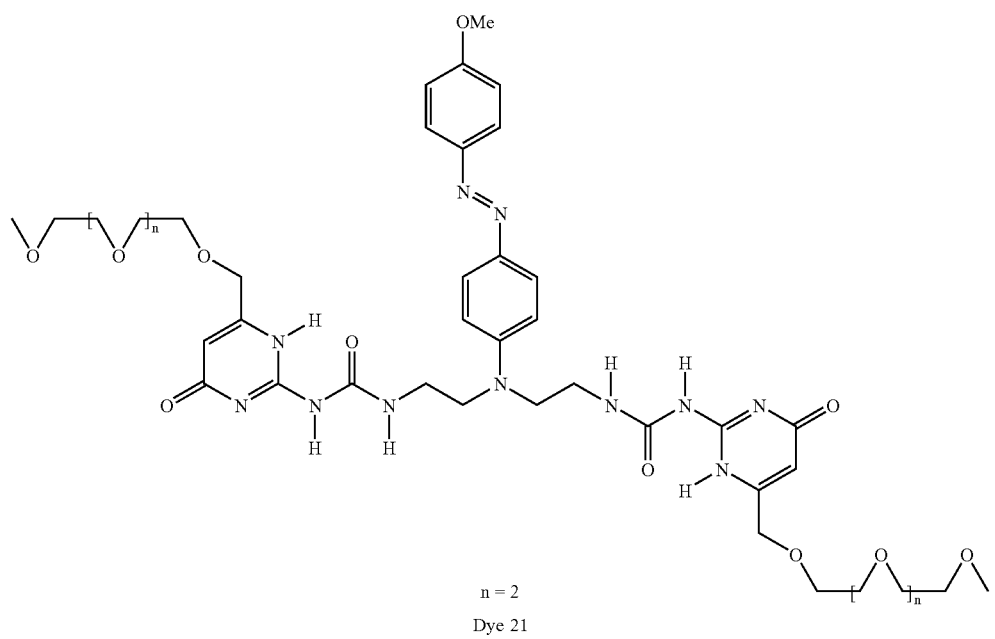
n = 2
Dye 21

TABLE 1-continued
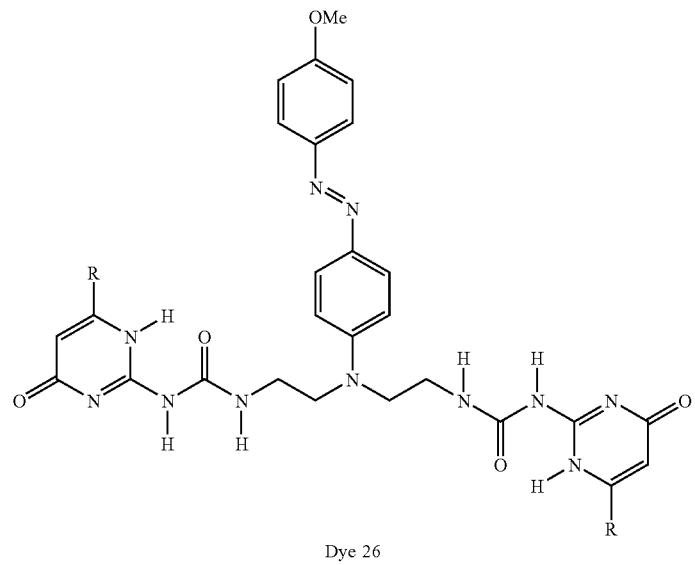
Dye 26
Dye 27
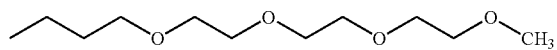
Dye 28
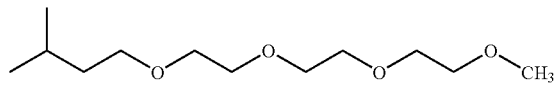
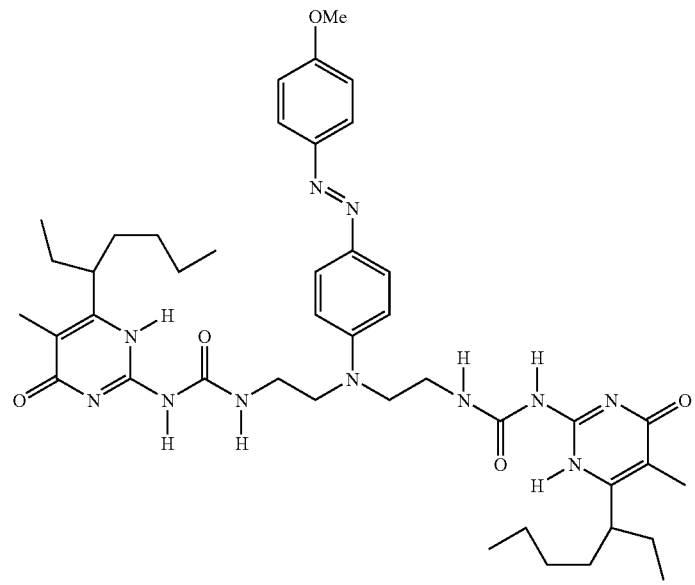
Dye 29
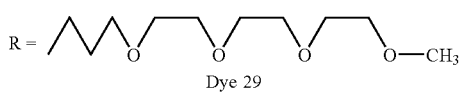

TABLE 1-continued

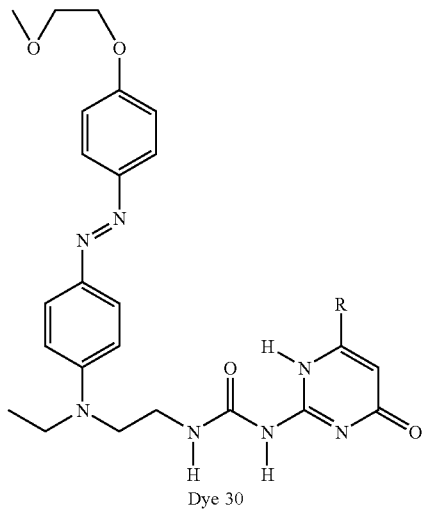
Dye 30

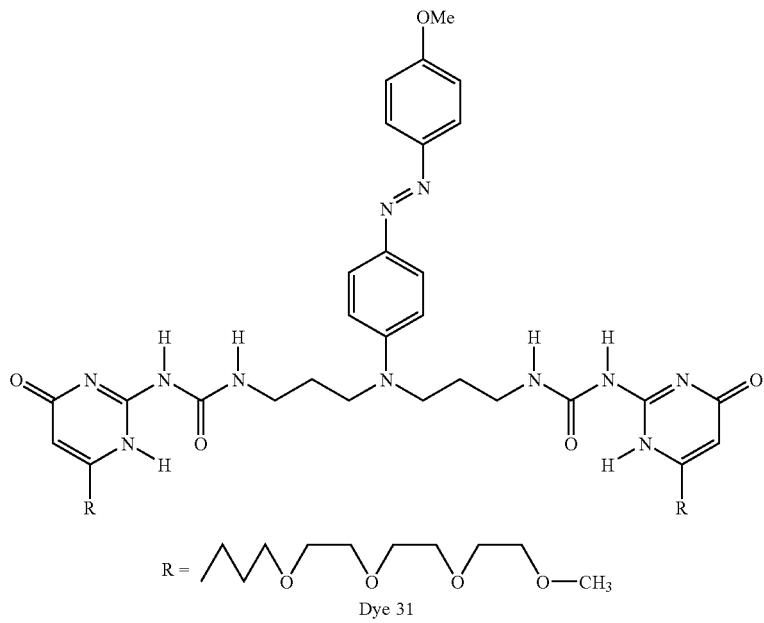
Dye 31

Self-assembling

According to the present invention self-assembling dyes are used to construct supramolecular dye-systems with improved properties such as light-fastness, water and solvent fastness. A distinctive feature of using weak, non-covalent forces in molecular assemblies is that such interactions are normally readily reversible so that the final product is in thermodynamic equilibrium with its components (usually via its corresponding partially assembled intermediates). This leads to an additional property of most supramolecular systems: they have a built-in capacity for error correction not available in fully covalent systems. Supramolecular is systems may also form under kinetic rather than thermodynamic control. This situation will tend to be more likely for larger supra-molecular assemblies incorporating many intermolecular contacts, especially when moderately rigid components are involved.

According to the present invention new self-assembling dyes with improved light-fastness properties have been developed whereby the process of molecular recognition and self-assembly through the formation of intermolecular hydrogen bonds is induced through the removal of the ink vehicle. This process is called "Evaporation Induced Self-Assembly (EISA)". EISA has been used to prepare a photosensitive thin-film mesophase containing a photo-acid generator (Science, Vol. 290, 6 Oct. 2000, 107-111) and for rapid prototyping of patterned functional nanostructures (Nature, Vol.405, 4 May 2000, 56-60). In liquid based inks EISA occurs through evaporation of the liquid. In phase change inks this process occurs through solidification of the ink. As long as the self-assembling dyes are dissolved in the ink no or only partial self-assembly occurs because of the formation of hydrogen bonds with the ink vehicle. Once the ink vehicle (or one of the ink vehicles) is removed through for example evaporation, self-assembly of the dyes is induced resulting in supramolecular structures. In these assemblies the integrity of the individual component molecules normally remains largely intact, that is, the wave functions of the respective molecular components remain largely separate on complex formation. However, after the initial self-assembly process through hydrogen bonding has started, secondary interactions may occur such as π-stacking resulting in more rigid structures with different physical properties such as shifts in spectral absorption and molecular extinction coefficient, extra energy levels for thermal relaxation, etc. Due to multiple intermolecular hydrogen bonding the molecule can absorb UV-radiation transforming it into vibrational energy and/or heat through efficient radiationless deactivation pathways, as described in J. Photochem. Photobiol. A: Chem. 1998, 41, p. 227.

According to the present invention the self-assembly process can occur between the self-assembling dyes themselves but also between (a) self-assembling dye molecule(s) and (a) complementary multiple H-donor/acceptor molecule(s) lacking the dye-fragment, e.g. molecules according to formula II.

Hydrogen bonds are a special type of electrostatic interaction and can be described as an attractive interaction between a proton donor and a proton acceptor. According to the present invention the definition of a hydrogen bond presented by Pimentel and McClellan (G. C. Pimentel, A. L. McClellan, The Hydrogen Bond, Freeman, San Francisco, 1960) is used, which is:

A hydrogen bond exists between a functional group A-H and an atom or a group of atoms B in the same or a different molecule when:
 (a) there is evidence of bond formation (association or chelation);
 (b) there is evidence that this new bond linking A-H and B specifically involves the hydrogen atom already bonded to A.

Both the donor (A) and the acceptor (B) atoms have electronegative character, with the proton involved in the hydrogen bond being shared between the electron pairs on A and B. The inherent directionality of hydrogen bonds makes them ideal for use in achieving complementarity in supramolecular systems.

Dye System

The self-assembly of dyes according to the present invention results in supra-molecular structures, which are called dye systems.

The self-assembly of dyes occurs by those parts of the dye molecules which are called SAU or 'self-assembling units'.

In the dyes according to the present invention the SAU is an ureidopyrimidone group represented by formula (II):

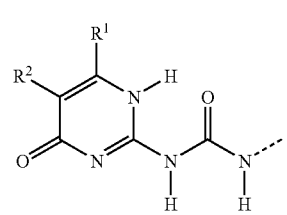

Formula (II)

wherein, $R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a chromophore group, or $R^1$ and $R^2$ represent the necessary atoms to form a ring system.

The self-assembling reaction may occur not only between identical self-assembling dyes according to formula (I), but also between two self-assembling dyes that differ in chemical structure, or between a self-assembling dye according to formula (I) and a self-assembling non-dye compound, as long as the SAU groups of the different dyes and/or non-dye compounds are capable of forming multiple hydrogen bonds with each other.

The association constant of the assembly reaction $K_{ass}$, determined by $^1$H-NMR in $CDCl_3$, is at least 2.5 $M^{-1}$, more preferably at least $10^2$ $M^{-1}$, and most preferably at least $10^5$ $M^{-1}$.

A representative example of a dye system is shown in System Formula 1.

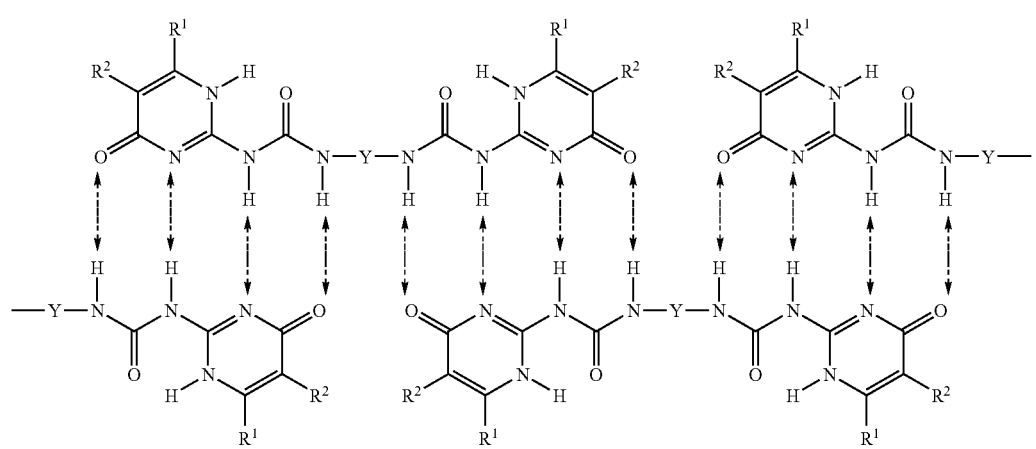

System Formula 1 wherein,

Y represents CU or Z-CU;

CU means any chromophore group absorbing between 200 nm and 2000 nm, such as an azo dye, an anthraquinone dye, a (poly)methine dye, an azomethine dye, a polyene dye, a pyrene dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye, a formazan dye;

$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted sulphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a CU group, or $R^1$ and $R^2$ represent the necessary atoms to form a ring system; and Z represents any linking group containing at least one carbon, nitrogen, silicon, phosphorous, sulfur or oxygen atom, but Z is preferably selected from the group consisting of substituted or unsubstituted alkyl groups, substituted or unsubstituted aryl groups, substituted or unsubstituted aralkyl groups, substituted or unsubstituted acyl groups, substituted or unsubstituted sulphonyl groups, substituted or unsubstituted phosphoryl group and heterocyclic groups.

Ink-jet Ink

The self-assembling dye according to Formula (I) of the present invention may be formulated in an ink-jet ink. Self-assembly through the formation of intermolecular hydrogen bonds, may be induced through evaporation of the ink vehicle. As long as the self-assembling dyes are dissolved in the ink no or partial self-assembly occurs because of the formation of hydrogen bonds with the ink vehicle. Once the ink vehicle (or one of the ink vehicles) is removed through, for example, evaporation, self-assembly of the dyes is induced resulting in supramolecular structures. In these assemblies the integrity of the individual component molecules normally remains largely intact: that is, the wave functions of the respective molecular components remain largely separate on complex formation. However, after the initial self-assembly process through hydrogen bonding has started, secondary interactions may occur such as π-stacking resulting in more rigid structures with different physical properties such as shifts in spectral absorption and molecular extinction coefficient, extra energy levels for thermal relaxation, etc.

Ink Vehicle

The ink compositions containing a self-assembling dye, according to the present invention, can be formulated as water based inks, solvent and/or oil based inks, as UV-curable inks and as hot melt (phase change) inks. Suitable ink compositions are described extensively in the existing patent literature and can be found for example in "Ink-jet Technology and Product Development Strategies, Stephen F. Pond, Torrey Pines Research, 2000, Chapter 5: Ink Design" and references cited therein.

Preferred ink compositions are those comprising dyes according to the present invention in an aqueous vehicle and in a solvent and/or oil based vehicle.

The self-assembling dyes, according to the present invention, are particularly useful as colorants for aqueous inks. The ink compositions preferably contain from 0.5% to 40%, more preferably from 0.5% to 15%, and especially from 1% to 10%, by weight of the dye of formula (I) based on the total weight of the ink. Although many ink compositions contain less than 5% by weight of colorant, it is desirable that the dye has a solubility of around 10 wt % or more. This allows the preparation of concentrated inks, which may be used to prepare more dilute inks and to minimize the chance of precipitation of colorant if evaporation of the liquid vehicle occurs during use of the ink.

When the liquid vehicle is an aqueous vehicle it is preferably water or a mixture of water and one or more water-soluble organic solvents. The weight ratio of water to organic solvent(s) is preferably from 99:1 to 1:99, more preferably from 99:1 to 50:50 and especially from 95:5 to 80:20. The water-soluble organic solvents) is(are) preferably selected from $C_{1-4}$-alkanols such as methanol, ethanol, n-propanol, isopropanol, n-butanol, sec-butanol, tert-butanol; amides such as dimethylformamide or dimethylacetamide; ketones or ketone-alcohols such as acetone or diacetone alcohol; ethers such as tetrahydrofuran or dioxane; oligo- or poly-alkyleneglycols such as diethylene glycol, triethylene glycol, hexylene glycol, polyethylene glycol or polypropylene glycol; alkyleneglycols or thioglycols containing a $C_2$-$C_6$ alkylene group such as ethylene glycol, propylene glycol, butylene glycol, pentylene glycol or hexylene glycol and thiodiglycol; polyols such as glycerol or 1,2,6-hexanetriol; $C_{1-4}$-alkyl-ethers of polyhydric alcohols such as 2-methoxyethanol, 2-(2-methoxyethoxy)ethanol, 2-(2-ethoxyethoxy)ethanol, 2-[2-(2-methoxyethoxy)ethoxy]ethanol, 2-[2-(2-ethoxyethoxy)-ethoxy]-ethanol, ethyleneglycolmonoallylether; heterocyclic amides, such as 2-pyrrolidone, N-methyl-2-pyrrolidone, N-ethyl-2-pyrrolidone and 1,3-dimethylimidazolidone; sulphoxides such as dimethyl sulphoxide and sulpholane or mixtures containing two or more of the aforementioned water-soluble organic solvents, for example thiodiglycol and a second glycol or diethylene glycol and 2-pyrrolidone. Preferred water-soluble organic solvents are 2-pyrrolidone; N-methyl-pyrrolidone; alkylene- and oligo-alkylene-glycols, such as ethyleneglycol, diethyleneglycol, triethyleneglycol; and lower alkyl ethers of polyhydric alcohols such as or 2-methoxy-2-ethoxy-2-ethoxyethanol; and polyethyleneglycols with a molecular weight of up to 500.

The self-assembling dyes, according to the present invention, are also particularly useful as colorants for solvent and/or oil based inks. Solvent based ink compositions are used where fast drying times are required and particularly when printing onto hydrophobic substrates such as plastics, metal or glass. Where the liquid vehicle is solvent based the solvent is preferably selected from ketones, alkanols, aliphatic hydrocarbons, esters, ethers, amides or mixtures thereof. Where an aliphatic hydrocarbon is used as the solvent a polar solvent such as an alcohol, ester, ether or amide is preferably added. Preferred solvents include ketones, especially methyl ethyl ketone and alkanols especially ethanol and n-propanol.

Typical solvents for solvent based ink-jet inks are methanol, ethanol, propanol, diacetone alcohol, methoxypropanol, glycol, methyl ethyl ketone, methyl isopropyl ketone, ethyl acetate, butyl acetate and methoxypropyl acetate, ethyl lactate and butyl lactate, monomethylethers from glycol, n.butylether from diethyleneglycol (Dowanol PM-series) and triethyleneglycol, tripropyleneglycolmonomethylether (TMP), dipropyleneglycolmonomethylether, and (di)methylnaphthalene. The less volatile solvents are more often used in oil based inks.

Solvent and/or oil based ink compositions of the present invention preferably contain from 0.5% to 40%, more preferably from 0.5% to 15%, and especially from 1% to 10%, by weight of the dye of formula (1) based on the total weight of the ink. Although many ink compositions contain less than 5% by weight of colorant, it is desirable that the dye has a solubility of around 10% or more. This allows the preparation of concentrated inks, which may be used to prepare more dilute inks and to minimize the chance of precipitation of colorant if evaporation of the liquid vehicle occurs during use of the ink.

When the vehicle for an ink composition is a low melting point solid, the melting point of the solid is preferably in the range from 60° C. to 125° C. Suitable low melting point solids include long chain fatty acids or alcohols, preferably those with $C_{18}$ to $C_{24}$ chains, or sulphonamides. The dyes according to the present invention or mixtures of the dyes may be dissolved in the low melting point solid or may be finely dispersed in it.

For ink-jet applications the viscosity of the final ink should be between 1-25 mPa·s at 20° C., preferably between 1-15 mPa·s at 20° C. and most preferably between 1-10 mPa·s at 20° C. for water and solvent-based inks, and between 1-25 mPa·s at 45° C., preferably between 2-18 mPa·s at 45° C. and most preferably between 3-12 mPa·s at 45° C. for oil-based inks.

Other Ingredients

The ink compositions containing a self-assembling dye, according to the present invention, may contain further colorants other than the dyes according the present invention, for example to modify the color or brightness of the ink. Colorants may be dyes, pigments or a combination thereof. Both organic and/or inorganic pigments may be used.

The ink compositions containing a self-assembling dye, according to the present invention, may further include a surfactant. The surfactant can be anionic, cationic, non-ionic, or zwitter-ionic and added in a total amount below 20.0 wt % based on the total ink weight.

A biocide may be added to the ink composition containing a self-assembling dye according to the present invention to prevent unwanted microbial growth, which may occur in the ink composition over time. The biocide may be used either singly or in combination. Each of them is preferably added in an amount of 0.001 to 3 wt % based on the total weight of the ink composition.

The ink composition may also contain stabilizing agents, such as UV-absorbers, singlet oxygen quenchers such as hindered amine light stabilizers, peroxide scavengers and other radical scavengers.

The ink composition containing a self-assembling dye according to the present invention may contain a humectant to prevent the clogging of the nozzle, due to its ability to slow down the evaporation rate of ink. Suitable humectants include, for example, triacetin, N-methyl-2-pyrrolidone, glycerol, urea, thiourea, ethylene urea, alkyl urea, alkylthiourea, dialkyl urea and dialkyl thiourea, diols, including ethanediols, propanediols, propanetriols, butanediols, pentanediols, and hexanediols; glycols, including propylene glycol, polypropylene glycol, ethylene glycol, polyethylene glycol, diethylene glycol, tetraethylene glycol, and mixtures and derivatives thereof. A preferred humectant is polyethylene glycol and added to the ink-jet ink formulation in an amount of 0.1 to 20 wt % of the ink composition.

The ink composition containing a self-assembling dye according to the present invention may further contain a thickener used for viscosity regulation, pH controlling agents, evaporation accelerators, rust inhibitors, crosslinking agents, soluble electrolytes as conductivity aid, sequestering agents and chelating agents.

Ink-jet Recording Element

The ink-jet recording element used with an ink composition containing a self-assembling dye according to the present invention comprises a support and optionally at least one ink-receiving layer.

The support of the ink-jet recording element can be chosen from the paper type, metal type and polymeric type support. Paper types include plain paper, cast coated paper, polyethylene coated paper and polypropylene coated paper. Polymeric supports include cellulose acetate propionate or cellulose acetate butyrate, polyesters such as polyethylene terephthalate (PET) and polyethylene naphthalate, polyamides, polycarbonates, polyimides, polyolefins, poly(vinylacetals), polyethers and polysulphonamides. Other examples of useful high-quality polymeric supports for the present invention include opaque white polyesters and extrusion blends of polyethylene terephthalate and polypropylene. Polyester film supports, and especially polyethylene terephthalate, are preferred because of their excellent properties of dimensional stability. When the ink-jet recording material is meant for outdoor use then typical useful supports include PET, wet strength paper, PVC, PVC with an adhesive backing, the polyethylene paper TYVEK, trade name of Du Pont Co., the porous polyethylene paper TESLIN, trade name of International Paper CO., canvas, polypropylene, and polycarbonate. Metal type supports include aluminum and steel plates.

The ink-receiving layer may contain the typical ingredients well known in the art from numerous patent applications. Typical ingredients include binders, pigments, mordants, surfactants, spacing agents, whitening agents, UV-absorbers, hardeners, plasticizers, etc.

Ink-jet Printing Apparatus

The ink-jet printing process can be performed according to any of the well-known techniques, such as the continuous printing method, the thermal jet method and the piezo method.

The present invention will now be illustrated by the following examples without however being limited thereto.

EXAMPLES

The Synthesis Examples 1 to 24 deal with the synthesis of the dyes used in accordance with the present invention, or of intermediates thereof. The evaluation of the dyes according to the present invention is described in the section 'Ink-jet Examples'.

Materials

All materials used in the examples were readily available from standard commercial sources such as ALDRICH CHEMICAL Co.(Belgium) unless otherwise specified.

Reference dyes are commercially available from commercial sources such as ALDRICH CHEMICAL Co.(Belgium), CLARIANT or MERCK are prepared according to published methods, unless described in the Examples.

Measurement Methods

UV data have been recorded in 1 cm sample holders with observed optical densities between 0.1 and 2.0. $\epsilon$ is given as $l.mol^{-1}.cm^{-1}$. Different Perkin Elmer UV-spectroscopes have been used. FT-IR spectra have been recorded on a Spectrum One Perkin Elmer ATR FT-IR spectroscope. NMR spectra have been recorded on a 300 MHz Varian spectroscope. MALDI-TOF MS data have been recorded on a Perceptive Voyager DE Pro spectrometer.

The density, i.e. optical density of the Ink-jet Examples was measured using a MacBeth TR1224 densitometer.

SYNTHESIS EXAMPLES

The Synthesis Examples 1 to 24 deal with the synthesis of the self-assembling dyes used in accordance with the present invention, or of intermediates thereof.

Synthesis Example 1

This example discloses the synthesis of the Isocyanate-1.

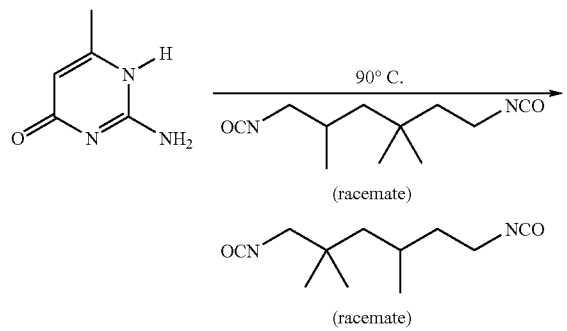

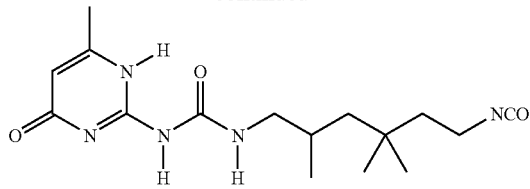

Isocynate-1
(mixture of 8 isomers (four racemates))

3 mL of pyridine were added to a white suspension of the isocytosine (2 gram) and a mixture of 2,2,4-trimethyl-1,6-diisocyanate and 2,4,4-trimethyl-1,6-diisocyanate (24 gram). The mixture was heated for 21 hours at an oil bath temperature of 100° C. under a slight argon flow. The reaction mixture was cooled to room temperature and pentane was added to induce precipitation of a white product. The suspension was filtered and the residue was washed several times with pentane to yield the isocyanate-1 as a white solid. Yield: 60%.

1H NMR (300 MHz, CDCl$_3$): δ=0.95-1.05 (m, 9H), 1.1 (m, 1H), 1.3 (m, 1H), 1.6 (m, 2H), 1.8 (m, 1H), 2.2 (s, 3H), 3.0-3.4 (m, 4H), 5.8 (s, 1H), 10.1 (s, 1H), 11.7 (s, 1H), 13.1 (s, 1H). IR: υ (cm−1)=709, 744, 761, 798, 844, 946, 971, 1028, 1132, 1171, 1248, 1319, 1368, 1381, 1390, 1415, 1439, 1469, 1518, 1580, 1647, 1693, 2260, 2873 2933, 2956, 3143, 3196.

Synthesis Example 2

This example discloses the synthesis of Dye-1.

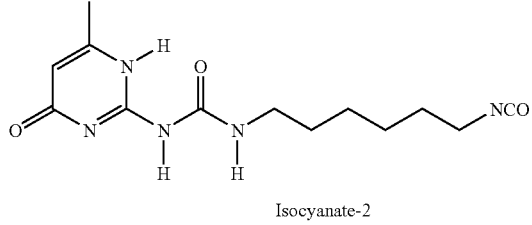

Isocyanate-2

DYE 135620
CHCl$_3$, reflux
dibutyltin dilaurate

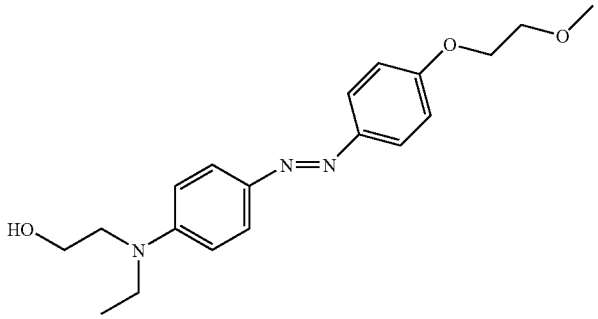

Reference dye-3

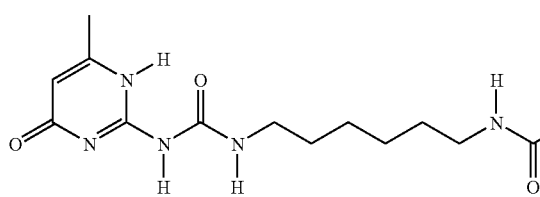

Dye-1

Reference dye-3 (17.4 gram) and the isocyanate-2 (prepared according to Example 1) (14.8 gram) were dissolved in 400 mL of dry chloroform. Several drops of the dibutyltin dilaurate catalyst were added and the reaction mixture was stirred under an argon atmosphere at an oil bath temperature of 80° C. for 21 hours. The reaction mixture was cooled to room temperature and added dropwise to 700 mL of hexane. The precipitated fine yellow powder was filtered and purified through a second precipitation from chloroform into a mixture of hexane/chloroform (500 mL/200 mL). 29.1 gram (90%) of Dye-1 was obtained.

1H NMR (300 MHz, CDCl$_3$): δ=1.1-1.7 (m, 11H), 2.1 (s, 3H), 3.0-3.2 (m, 4H), 3.4 (m, 5H), 3.6 (m, 2H), 3.7 (m, 2H), 4.1 (m, 2H), 4.3 (m, 2H), 5.15 and 5.2 (2s, 1H), 5.8 (s, 1H), 6.75 (d, 2H), 6.95 (d, 2H), 7.8 (d, 4H), 10.1 (s, 1H), 11.7 (s, 1H), 13.1 (s, 1H). MALDI-TOF MS (FW=636.75), found m/z=637.13. IR: υ (cm−1)=666, 750, 823, 837, 923, 942, 1003, 1035, 1058, 1105, 1132, 1151, 1194, 1240, 1315, 1361, 1377, 1396, 1446, 1511, 1546, 1583, 1667, 1682, 1700, 2929, 3290. λmax=409 nm; ε=26321 (CHCl3); λmax=409 nm; ε=29000 (MeOH).

Synthesis Example 3

This example discloses the synthesis of Dye-2.

Reference dye-1 (709 mg) and the isocyanate-2 (470 mg) were dissolved in 50 mL of dry chloroform. Several drops of dibutyltin dilaurate (catalyst) were added. The reaction mixture was refluxed for 21 hours under argon, cooled to room temperature and the solvent was removed under reduced pressure. The compound was purified using column chromatography starting with pure chloroform as the eluent and gradually switching to 2% methanol/chloroform eluent. The collected product was precipitated in hexane (to remove the catalyst that is still present after chromatography). Yield: 90% of Dye-2.

1H NMR (300 MHz, CDCl$_3$): δ=0.9 (t, 3H), 1.1-1.7 (m, 13H), 2.1 (s, 3H), 2.4 (s, 3H), 3.1 (m, 4H), 3.4 (m, 4H), 3.6 (s, 2H), 4.2 (m, 2H), 5.2-5.4 (2s, 1H), 5.8 (s, 1H), 6.6 (m, 1H), 6.7 (m, 2H), 7.5 (m, 1H), 7.6 (t, 1H), 8.1 (d, 1H), 8.4 (m, 2H), 9.3 (m, 1H), 10.1 (s, 1H), 11.7 (s, 1H), 13.1 (s, 1H). MALDI-TOF MS (FW=712.84), found m/z=714.24. IR: υ (cm−1)=667, 753, 799, 842, 937, 988, 1029, 1072, 1101, 1139, 1193, 1250, 1318, 1353, 1393, 1446, 1470, 1501, 1534, 1578, 1606, 1660, 1698, 2859, 2929, 3288. λmax=678 nm; ε=24288 (CHCl3); λmax=681 nm; ε=23000 (MeOH).

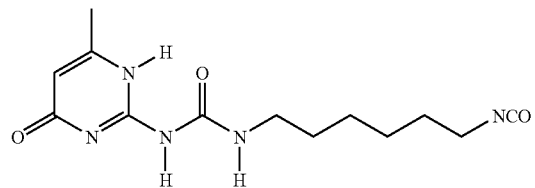

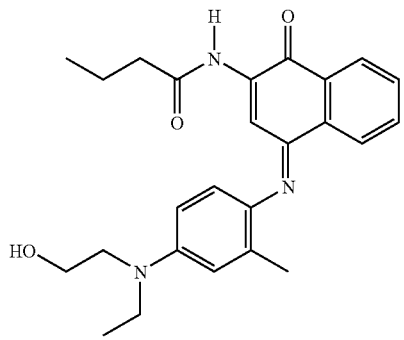

Reference dye-1

DYE 137526
CHCl$_3$, reflux
dibutyltin dilaurate

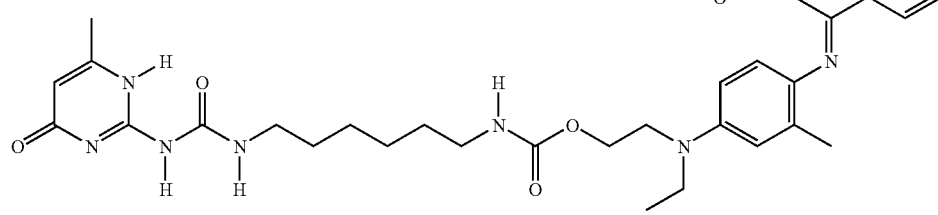

Dye-2

Synthesis Example 4

This example discloses the synthesis of Dye-3.

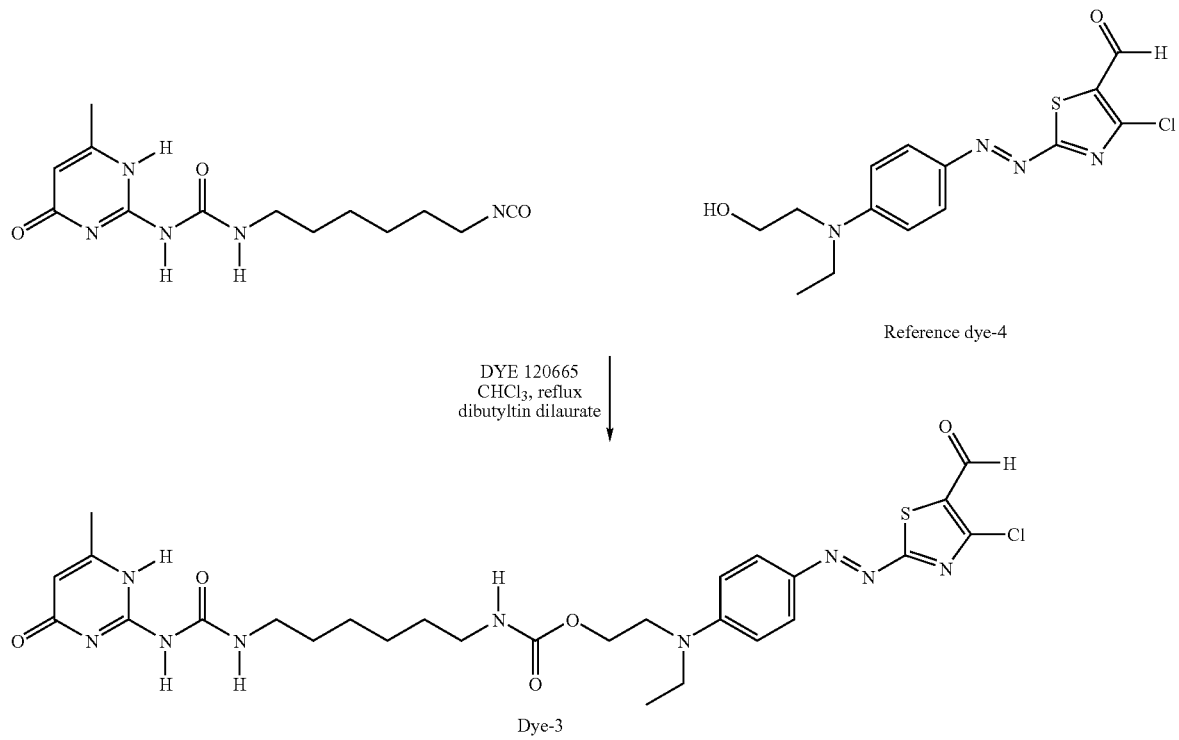

Reference dye-4

Dye-3

Reference dye-4 (706 mg) and the isocyanate-2 (579 mg) were dissolved in 50 mL of dry chloroform. Several drops of dibutyltin dilaurate (catalyst) were added, and the reaction mixture was boiled under an argon atmosphere for 21 hours. The reaction mixture was cooled to room temperature and the solvent was removed under reduced pressure. The compound was purified using column chromatography starting with pure chloroform as the eluent and gradually switching to 2% methanol in chloroform. The collected product was precipitated in hexane (to remove the catalyst) to yield 1.15 gram of Dye-3 (92%).

1H NMR (300 MHz, CDCl$_3$): δ=1.1-1.6 (m, 11H), 2.2 (s, 3H), 3.2 (m, 4H), 3.6 (m, 2H), 3.7 (m, 2H), 4.3 (m, 2H), 5.2-5.4 (2s, 1H), 5.8 (s, 1H), 6.8 (m, 2H), 7.9 (d, 2H), 10.0 (s, 1H), 10.1 (s, 1H), 11.7 (s, 1H), 13.1 (s, 1H). MALDI-TOF MS (FW=632.12), found m/z=632.14.

IR: υ (cm−1)=653, 664, 684, 721, 799, 826, 880, 926, 997, 1072, 1101, 1215, 1242, 1309, 1327, 1372, 1411, 1445, 1482, 1519, 1581, 1595, 1658, 1697, 2856, 2928, 3214. λmax=555 nm; ϵ=44000 (CHCl3); λmax=547 nm; ϵ=38000 (MeOH).

Synthesis Example 5

This example discloses the synthesis of Dye-4.

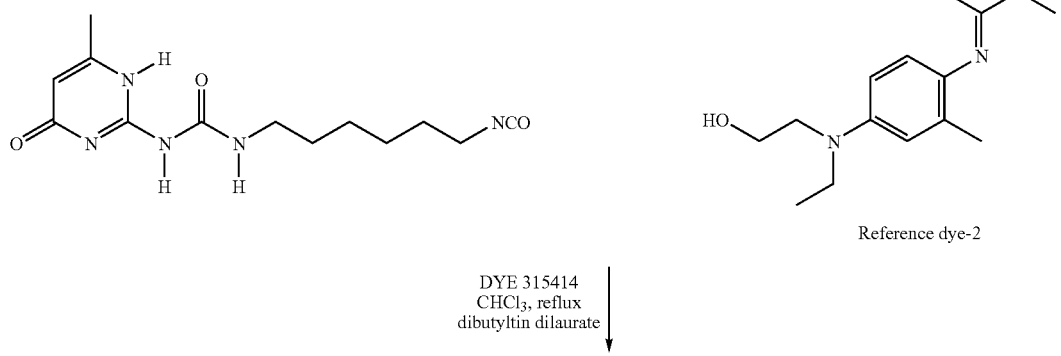

Reference dye-2

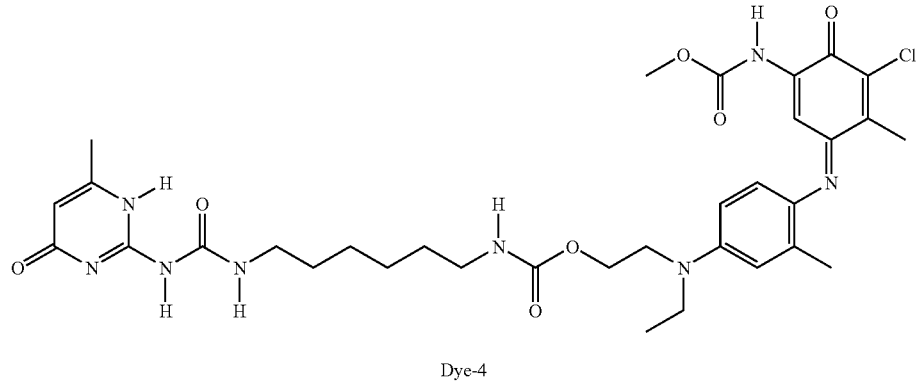

Dye-4

Reference Dye-2 (9.9 gram) and the isocyanate-2 (7.2 gram) were dissolved in 300 mL of dry chloroform. Several drops of dibutyltin dilaurate (catalyst) were added and the reaction mixture was refluxed for 21 hours under an argon atmosphere. The reaction mixture was cooled to room temperature and added dropwise to 700 mL of hexane. After a second precipitation Dye-4 is obtained as a blue powder: 16.1 gram (92%).

1H NMR (300 MHz, CDCl$_3$): δ=1.2 (t, 3H), 1.3 (m, 4H), 1.4-1.6 (m, 4H), 2.2 (s, 3H), 2.3 (s, 3H), 2.5 (s, 3H), 3.0-3.2 (m, 4H), 3.4 (m, 2H), 3.5 (m, 2H), 3.7 (s, 3H), 4.2 (m, 2H), 5.1 and 5.3 (2s, 1H), 5.8 (s, 1H), 6.6 (m, 2H), 6.8 (d, 1H), 7.6 (s, 1H), 7.9 (s, 1H), 10.1 (s, 1H), 11.7 (s, 1H), 13.1 (s, 1H). MALDI-TOF MS (FW=699.20), found m/z=700.25. IR: υ (cm−1)=664, 750, 784, 804, 843, 875, 917, 968, 1042, 1110, 1135, 1179, 1243, 1318, 1348, 1375, 1393, 1455, 1514, 1583, 1630, 1660, 1698, 1700, 2858, 2929, 3216, 3374.

λmax=653 nm; ε=26000 (CHCl3); λmax=652 nm; ε=21000 (MeOH).

Synthesis Example 6

This example discloses the synthesis of Dye-5.

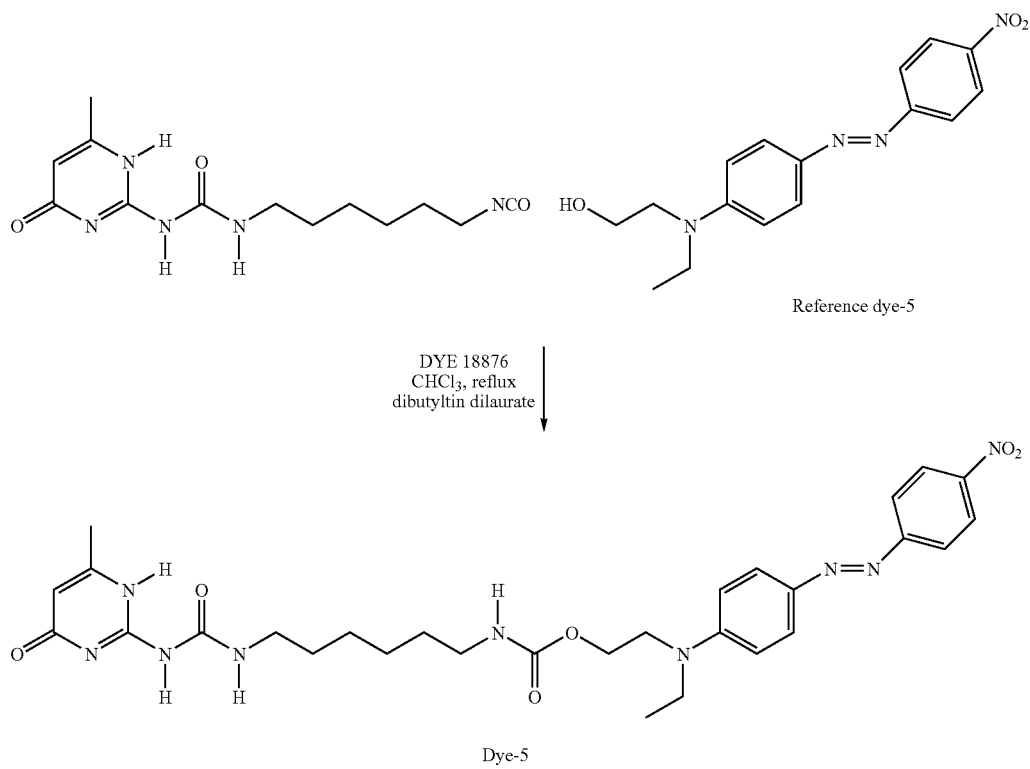

Dye-5

Reference dye-5 (1.0 gram) and the isocyanate-2 (1.0 gram) were mixed in 20 mL dry CHCl3 and 5 mL dry pyridine. Several drops of dibutyltin dilaurate (catalyst) were added and the reaction mixture was boiled and stirred under an argon atmosphere for several hours. The mixture was cooled. Evaporation and co-evaporation with toluene removed the solvent. Dye-5 was obtained as a red powder.

1H NMR (300 MHz, CDCl₃): δ=3.1-3.3 (m, 4H), 3.5 (m, 2H), 3.7 (m, 2H), 4.2 (m, 2H), 5.0-5.2 (2s, 1H), 5.8 (s, 1H), 6.8 (m, 2H), 7.9 (m, 4H), 8.3 (m, 2H), 10.1 (s, 1H), 11.7 (s, 1H), 13.1 (s, 1H).

MALDI-TOF MS (FW=607.7), found m/z=608.2. IR: υ (cm−1)=689, 741, 767, 798, 858, 943, 1041, 1105, 1133, 1194, 1251, 1311, 1338, 1384, 1446, 1512, 1590, 1662, 1698, 2857, 2932, 3230. λmax=479 nm (CHCl3); λmax=476 nm (MeOH).

Synthesis Example 7

This example discloses the synthesis of Dye-6.

remove the catalyst; further purification was achieved with column chromatography (starting with pure chloroform as eluent and changing to 2% MeOH in chloroform). After chromatography, Dye-6 was precipitated from chloroform in pentane. Yield 3.28 gram (75%).

1H NMR (300 MHz, CDCl₃): δ=0.9-1.0 (m, 10H), 1.2-1.4 (m, 4H), 1.5-1.7 (m, 3H), 2.2 (s, 3H), 2.3 (s, 3H), 2.5 (s, 3H), 3.0 (m, 2H), 3.2 (m, 2H), 3.5 (m, 2H), 3.6 (m, 2H), 3.7 (s, 3H), 4.2 (m, 2H), 5.2-5.4 (2s, 1H), 5.8 (s, 1H), 6.6 (m, 2H), 6.75 (d, 1H), 7.7 (s, 1H), 7.9 (s, 1H), 10.1 (s, 1H), 11.7 (s, 1H), 13.1 (s, 1H). IR: υ (cm−1)=666, 705, 745, 768, 784, 804, 842, 875, 917, 968, 1042, 1110, 1135, 1179, 1250,

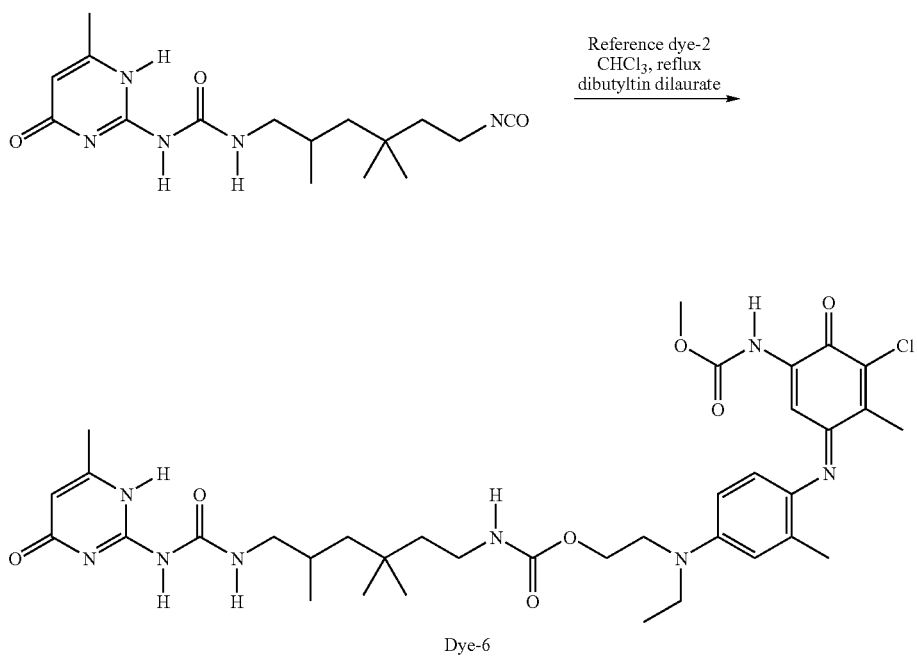

Dye-6

The isocyanate-1 (2.0 g; 5.96 mmol) and reference dye-2 (see example 5) (2.43 g; 5.99 mmol) were dissolved in 120 mL of dry chloroform. A few drops of dibutyltin dilaurate catalyst were added and the mixture was refluxed for 24 hours under an argon atmosphere. The reaction was monitored with TLC (2% MeOH/CHCl₃). Silica was added and the suspension was stirred for a few hours, followed by filtration. The filtrate was concentrated and the residue was dissolved in chloroform and precipitated in pentane to 1319, 1350, 1376, 1394, 1456, 1515, 1595, 1632, 1660, 1697, 1723, 2957, 3218, 3376. λmax=655 nm; ε=25000 (CHCl₃); λmax=647 nm; ε=21000 (MEK); λmax=638 nm; ε=24000 (EtOAc).

Synthesis Example 8

This example discloses the synthesis of Dye-7.

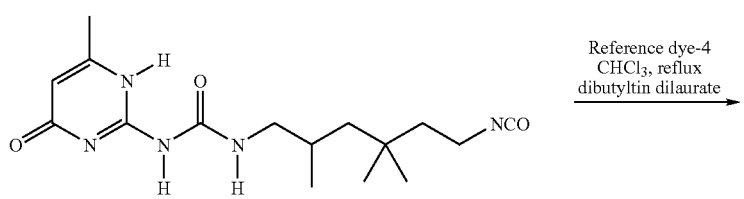

-continued

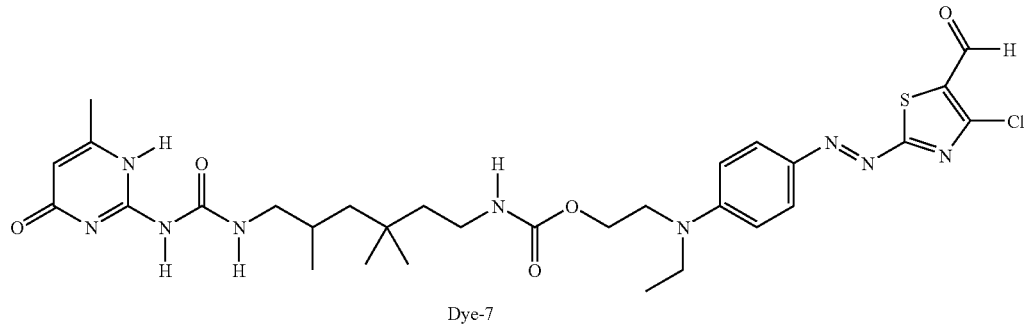

Dye-7

The isocyanate-1 (3.5 g; 10.4 mmol) and reference dye-4 (3.58 g; 10.6 mmol) were dissolved in 120 mL of dry chloroform. A few drops of dibutyltin dilaurate catalyst were added and the mixture was refluxed for 24 hours under argon. The reaction was followed with TLC (2% MeOH/CHCl$_3$). Silica was added and the suspension was stirred for a few hours, followed by filtration. The filtrate was concentrated under reduced pressure and the residue was dissolved in chloroform and precipitated in pentane to remove the catalyst; further purification was achieved with column chromatography (starting with pure chloroform as eluent and changing to 2% MeOH in chloroform; alternatively, EtOAc/hexane mixtures can be used). After chromatography, Dye-7 was precipitated from chloroform into pentane. Yield 4.2 gram (60%).

1H NMR (300 MHz, CDCl$_3$): δ 0.9 (m, 9H), 1.0-1.8 (8H), 2.2 (s, 3H), 2.8-3.0 (m, 4H), 3.5 (m, 2H), 3.7 (m, 2H), 4.3 (m, 2H), 5.2-5.4 (1H), 5.8 (s, 1H), 6.8 (m, 2H), 7.9 (m, 2H), 10.1 (m, 2H), 11.9 (bs, 1H), 13.1 (bs, 1H).

FT-IR: υ (cm−1)=666, 684, 721, 761, 796, 826, 880, 925, 997, 1013, 1073, 1123, 1218, 1244, 1310, 1327, 1372, 1411, 1482, 1520, 1597, 1660, 1698, 2957. λmax=553 nm; ε=3700 (CHCl3); λmax=561 nm; ε=39000 (MEK); λmax=553 nm; ε=36000 (EtOAc).

Synthesis Example 9

This example discloses the synthesis of Dye-8.

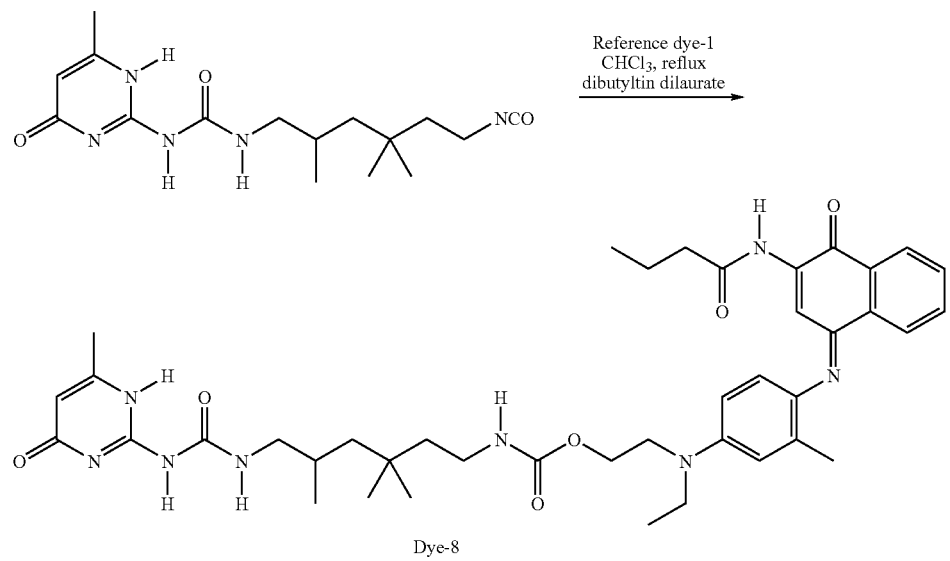

Dye-8

The isocyanate-1 (2.0 g; 5.96 mmol) and reference dye-1 (2.5 g; 5.96 mmol) were dissolved in 120 mL of dry chloroform. A few drops of dibutyltin dilaurate catalyst were added and the mixture was refluxed for 96 hours under argon. The reaction was followed with TLC (2% MeOH/CHCl$_3$). Silica was added and the suspension was stirred for a few hours, followed by filtration. The filtrate was concentrated under reduced pressure and the residue was dissolved in chloroform and precipitated in pentane to remove the catalyst; further purification was achieved with column chromatography (starting with pure chloroform as eluent and changing to 2% MeOH in chloroform; alternatively, EtOAc/hexane mixtures can be used). After chromatography, Dye-8 was precipitated from chloroform into pentane. Yield: 60%.

1H NMR (300 MHz, CDCl$_3$): δ 0.9-1.9 (22H), 2.2 (s, 3H), 2.4 (s, 3H), 3.0 (m, 2H), 3.2 (m, 2H), 3.4 (m, 4H), 3.6 (m, 2H), 4.3 (t, 2H), 5.2-5.4 (1H), 5.8 (s, 1H), 6.6 (d, 1H), 6.7

(m, 2H), 7.6 (t, 1H), 7.7 (t, 1H), 8.2 (d, 1H), 8.48 (s 1H), 8.55 (d, 1H), 9.3 (t, 1H), 10.1 (bs, 1H), 11.9 (bs, 1H), 13.1 (bs, 1H).

FT-IR: υ (cm−1)=696, 754, 797, 841, 936, 1029, 1072, 1100, 1138, 1193, 1246, 1318, 1354, 1393, 1447, 1470, 1501, 1532, 1580, 1607, 1660, 1698, 2958. λmax=684 nm; ϵ=25000 (CHCl3); λmax=679 nm; ϵ=22000 (MEK); λmax=680 nm; ϵ=22000 (EtOAc).

Synthesis Example 10

This example discloses the synthesis of Dye-9.

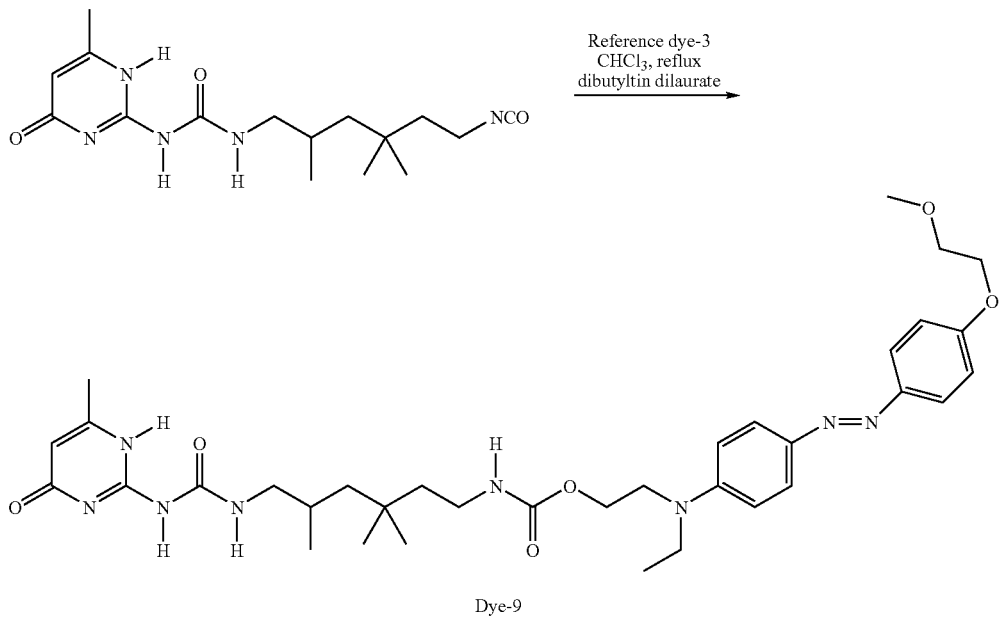

Dye-9

The isocyanate-1 (6.15 g; 18.3 mmol) and reference dye-3 (6.00 g; 17.5 mmol) were dissolved in 180 mL of dry chloroform. A few drops of dibutyltin dilaurate catalyst were added and the mixture was refluxed for 24 hours under argon. The reaction was followed with TLC (2% MeOH/CHCl3) and IR. The reaction mixture was evaporated under reduced pressure and the residue was precipitated from chloroform into pentane to remove the catalysts. The compound was then purified with column chromatography (starting with 1/1 EtOAc/hexane as eluent and changing gradually to 3/1 EtOAc/hexane; the product was collected by eluting with 4% MeOH in chloroform). After chromatography, dye-9 was precipitated from chloroform into pentane.

1H NMR (300 MHz, CDCl3): δ 0.9 (m, 9H), 1.0-1.8 (8H), 2.2 (s, 3H), 3.0 (m, 2H), 3.3 (m, 2H), 3.5 (m, 5H), 3.6 (m, 2H), 3.8 (m, 2H), 4.2-4.4 (m, 4H), 5.0-5.4 (three m, 1H), 5.8 (s, 1H), 6.8 (m, 2H), 7.0 (d, 2H), 7.8 (m, 4H), 10.1 (m, 1H), 11.9 (bs, 1H), 13.1 (bs, 1H).

FT-IR: υ (cm−1)=664, 731, 775, 821, 836, 924, 1033, 1060, 1133, 1149, 1196, 1242, 1316, 1355, 1396, 1447, 1511, 1581, 1594, 1660, 1697, 2956, 3216. λmax=409 nm; ϵ=29112(CHCl3).

Synthesis Example 11

This example discloses the synthesis of Dye-10.

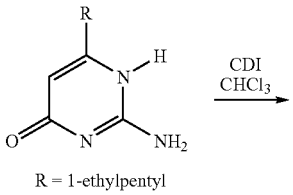

R = 1-ethylpentyl

-continued

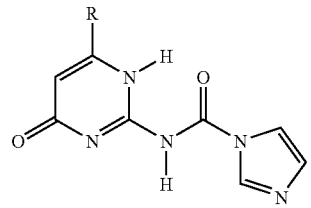

CDI Activation of 6-(1-ethylpentyl)isocytosine.

6-(1-Ethylpentyl)-isocytosine (3.0 gram, 14.4 mmol) and carbonyldiimidazole (CDI; 3.24 gram, 20 mmol) were stirred at room temperature in 40 mL CHCl3 for two hours, during which the mixture was kept under an argon atmosphere. The solution was washed with an aqueous NaCl solution, dried with MgSO4 and concentrated to give a quantitative yield of CDI-activated product. NMR analyses showed signals at the expected resonances and no traces of excess CDI were discerned. (The isocytosine starting product had been prepared by a standard coupling procedure of its β-keto ester precursor and guanidine carbonate).

1H NMR (CDCl$_3$), λ=12.9 (2H, bs), 8.6 (1H, s), 7.5 (1H, s), 6.9 (1H, s), 5.7 (1H, s), 2.4 (1H, m), 1.6 (4H, m), 1.2 (4H, m), 0.95-0.7 (6H, m).

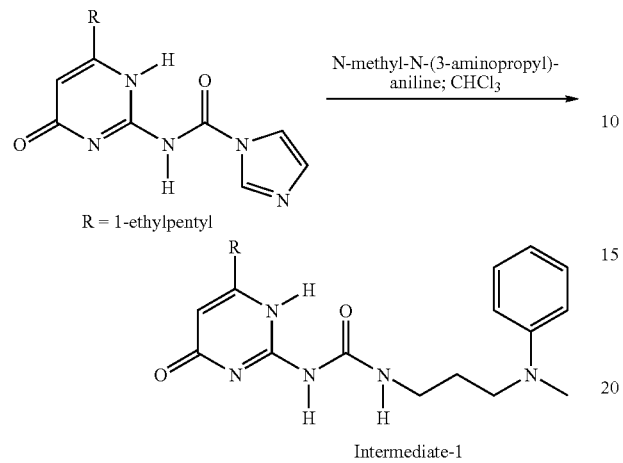

Synthesis of Intermediate-1

The CDI-activated product of (1-ethylpentyl)-isocytosine (4.3 gram, 14.4 mmol) was stirred overnight at room temperature in CHCl$_3$ together with N-methyl-N-(3-aminopropyl)-aniline (2.45 gram, 15 mmol). The solution was subsequently washed with a HCl solution and a NaHCO3 solution, and thereafter dried and concentrated. Column chromatography over silica with hexane/EtOAc 1/1 gave 4.8 gram of Intermediate-1 (85%). The oil solidified on standing.

1H NMR (CDCl$_3$), δ=13.2 (1H, s), 12.0 (1H, s), 10.3 (1H, s), 7.2 and 6.7 (5H), 5.8 (1H, s), 3.5-3.3 (4H, m), 3.0 (3H, s), 2.3 (1H, m), 1.9 (2H, m), 1.8-1.5 (4H, m), 1.3 (4H, m), 0.95-0.8 (6H, m).

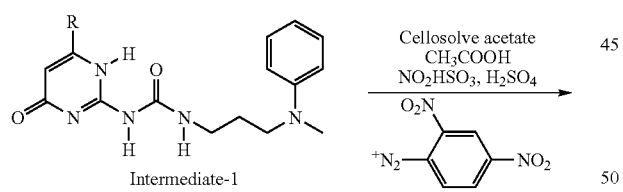

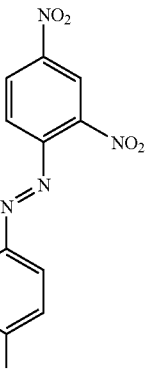

Synthesis of Dye-10.

2,4-Dinitroaniline (0.6 gram, 3.3 mmol) was suspended in 4.5 mL of acetic acid and 0.6 mL of H$_2$SO$_4$. A 40% solution of nitrosyl sulfuric acid (NO$_2$HSO$_3$, 0.9 gram, 2.8 mmol) in H$_2$SO$_4$ was added to this mixture, while remaining the mixture at 15° C. Stirring was continued for 30 minutes. The resulting yellow solution was added dropwise to a cooled solution of Intermediate-1 (0.5 gram, 1.26 mmol) in 4 mL of cellosolve acetate. The mixture turned red and was stirred overnight, while the temperature of the mixture was allowed to rise from 5° C. to room temperature. The clear mixture was poured on crushed ice to yield a purple-reddish solid that was filtered and washed with water. The product was dissolved in CHCl$_3$, washed twice with a NaHCO$_3$ solution, and once with a saturated NaCl solution. After drying over MgSO$_4$, and concentration, the product was dissolved in CHCl$_3$ and a small amount of acetic acid, and this solution was added dropwise to warm ethanol, yielding pure Dye-10 (0.37 gram, 50%).

1H NMR (CDCl$_3$), δ=13.1 (1H, s), 12.0 (1H, s), 10.4 (1H, s), 8.7 (1H, s), 8.4 (1H, d), 7.9 (3H, m), 6.8 (2H, d), 5.8 (1H, s), 3.6 (2H, m), 3.4 (2H, m), 3.2 (3H, s), 2.3 (1H, m), 2.0 (2H, m), 1.7-1.5 (4H, m), 1.3 (4H, m), 0.9 (6H, m).

Synthesis Example 12

This example discloses the synthesis of Dye-12.

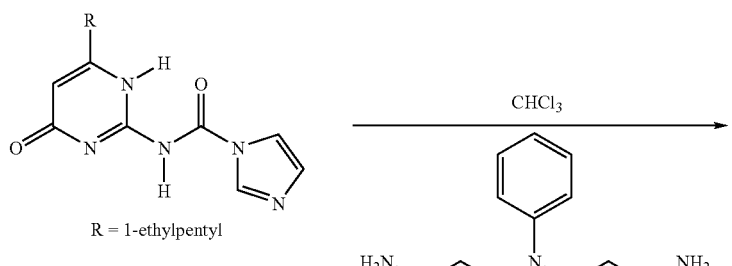

-continued

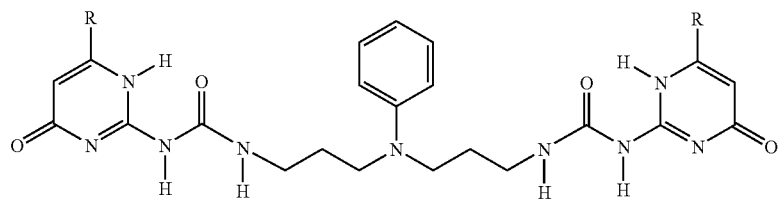

Intermediate-2

Synthesis of Intermediate-2.

The CDI-activated product of (1-ethylpentyl)-isocytosine (2.6 gram, 8.5 mmol, 2.2 equivalents) was stirred overnight at room temperature in CHCl₃ together with N-(bis-3-aminopropyl)-aniline (0.8 gram, 3.85 mmol). The solution was subsequently washed with a HCl solution and a NaHCO3 solution, and thereafter dried and concentrated. The product was dissolved in CHCl₃ and a small amount of acetic acid and was precipitated in ethanol. The suspension was heated until a clear solution was obtained. After cooling, pure Intermediate-2 was isolated as a white precipitate. (The diamine had been prepared by cyanoethylation of aniline, subsequent hydrogenation and purification by distillation under reduced pressure).

1H NMR (CDCl₃), δ=13.1 (2H, s), 12.0 (2H, s), 10.3 (2H, s), 7.4-7.0 and 6.8-6.5 (5H), 5.8 (2H, s), 3.5-3.3 (8H, m), 2.3 (2H, m), 2.0 (4H, m), 1.6 (8H, m), 1.3 (8H, m), 0.95-0.7 (12H, m).

Synthesis of Dye-12.

Tetracyanoethylene (0.104 gram, 0.81 mmol) in 1.5 mL DMF was added dropwise to a heated (65° C.) suspension of Intermediate-2 (0.5 gram, 0.74 mmol) in 1.5 mL DMF. During addition a purple-reddish Colour developed (the reaction mixture was flushed with nitrogen, and the nitrogen was led through a NaOH/NaOCl trap to remove HCN). After the addition was complete, the mixture was stirred for 1.5 hours at 70° C. Addition of 6 mL ethanol, further stirring for an hour, cooling to room temperature and addition of some water resulted in a suspension that was filtered and washed with water and ethanol. After drying the structure of Dye-12 was confirmed by MALDI-TOF MS ([M+]=779, [M+Na+]=802, [M+K+]=818).

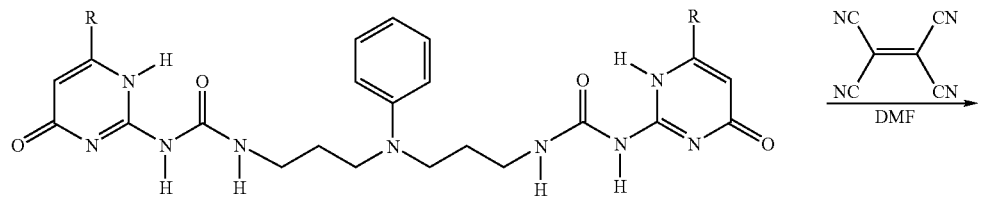

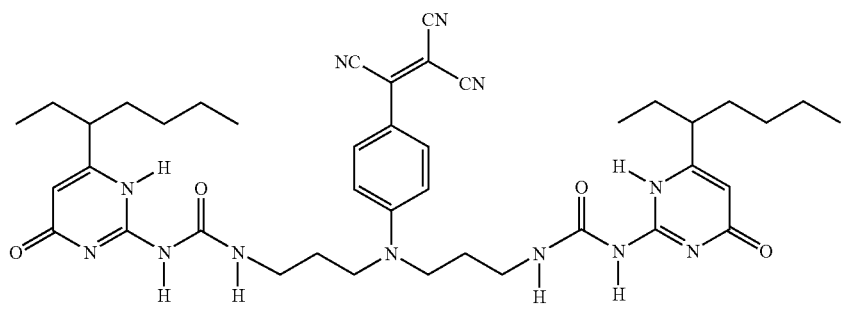

Dye-12

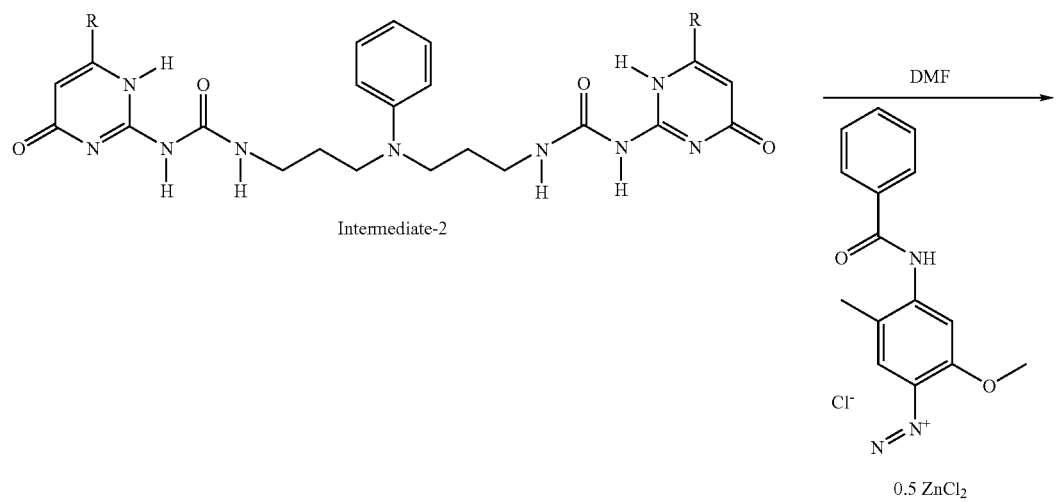

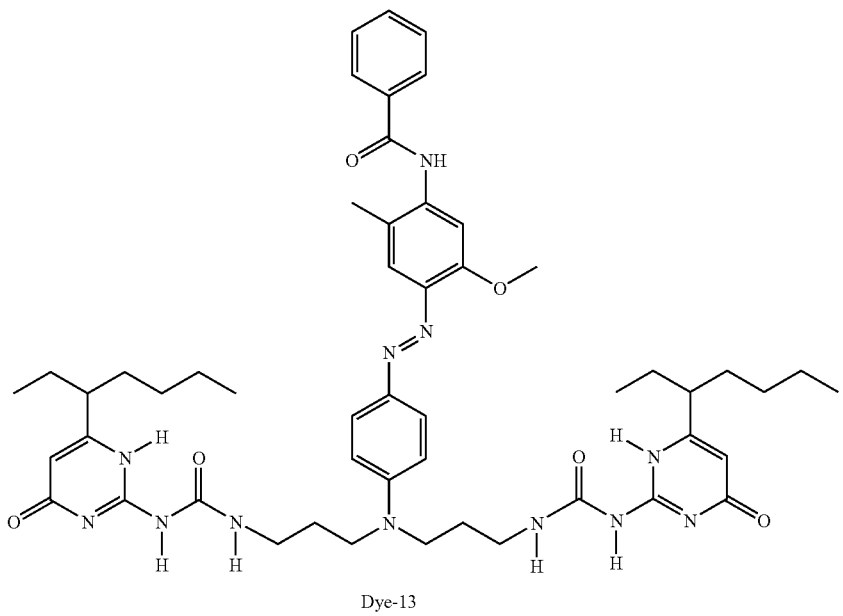

Intermediate-2 (0.25 gram, 0.37 mmol) was stirred in 5 mL DMF at 65° C. together with the commercial diazonium salt (fast violet B salt, 0.283 gram, 0.76 mmol). The mixture became homogeneous and dark and was stirred at the given temperature for 1.5 hours. After cooling, CHCl₃ was added and the mixture was washed with acidic water and with a NaHCO₃ solution. After drying and precipitation the precipitate was purified using column chromatography. MALDI-TOF MS analysis as well as NMR analysis confirmed the structure of Dye-13. ([M+H$^+$]=946, [M+Na+]=968).

Synthesis Example 14

This example discloses the synthesis of Dye-14.

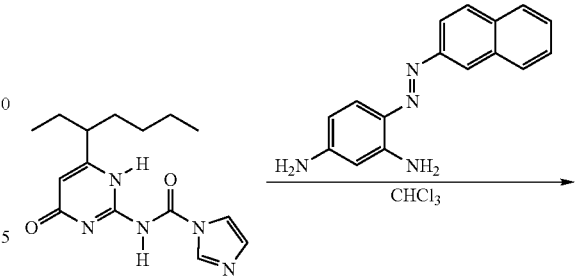

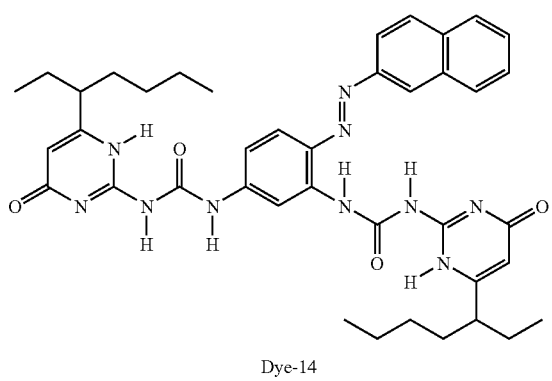
Dye-14

The activated 6-(1-ethylpentyl)isocytosine (2.8 gram; 9.3 mmol) was dissolved in 50 mL dry CHCl$_3$ together with Solvent Brown 1 (Fat Brown RR; C.I.11285) (1.06 gram, 4.0 mmol), and the mixture was heated in an oil bath of 80° C. for about 20 hours. Purification by column chromatography (silica; CHCl$_3$/MeOH, 98/2), and then by precipitation into acetone afforded Dye-14 as an orange solid.

1H NMR (CDCl$_3$, TFA-D1), δ=12.0 (6H, bs), 8.9 (1H, d), 8.4 (1H, bs), 8.0 (4H, m), 7.6 (4H, m), 6.3 (1H, s), 6.2 (1H, s), 2.6 (2H, m), 1.7 (8H, m), 1.4 (8H, m), 1.0 (12H, m). λmax=408 nm; ε=19868 (CHCl$_3$).

MALDI-TOF MS analysis, [M+H$^+$]=734, [M+Na+]=756, [M+K+]=772.

λmax=408 nm; ε=20000 (CHCl$_3$).

Synthesis Example 15

This example discloses the synthesis of Dye-15

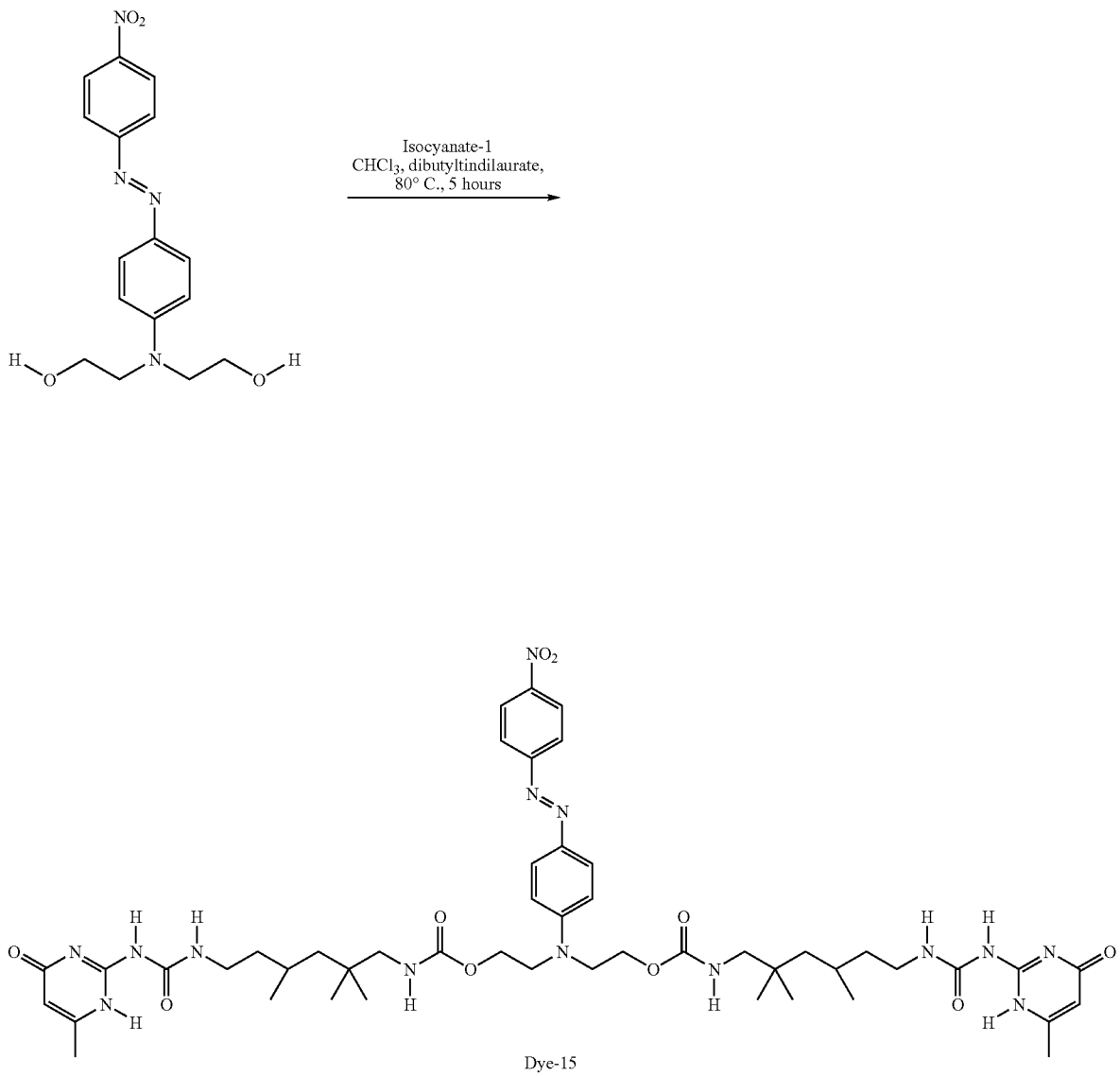
Dye-15

The starting diol (0.5 gram), Isocyanate-1 (1.11 gram) and a drop of dibutyltin dilaurate catalyst were mixed and heated in 100 mL of dry chloroform. After 24 hours of reflux, all isocyanate was consumed (FTIR analysis). The red product Dye-15 was isolated using column chromatography (silica, CHCl$_3$/MeOH, 98/2).

1H NMR (CDCl$_3$), δ=13.1 (2H, bs), 11.8 (2H, bs), 10.1 (2H, bs), 8.3 (2H, m), 7.9 (4H, m), 6.8 (2H, m), 5.8 (2H, s), 5.8-5.2 (2H), 4.2 (4H, m), 3.7 (4H, m), 3.3-2.8 (8H), 2.2 (6H, s), 1.8-1.2 (8H, m), 1.0 (20H, m). λmax=464 nm; ε=28465 (CHCl$_3$).

MALDI-TOF MS analysis, [M+H+]=1001, [M+Na+]=1023.

λmax=464 nm; ε=28000 (CHCl$_3$).

Synthesis Example 16

This example discloses the synthesis of Dye-16.

The starting diol (1 gram), Isocyanate-1 (2.3 gram) and a drop of dibutyltin dilaurate catalyst were mixed and heated in 100 mL of dry chloroform. After 40 hours of reflux isocyanate-1 was completely consumed (FTIR analysis). After column chromatography (silica, CHCl$_3$/MeOH, 98/2) Dye-16 (1.25 gram) was isolated as a yellow powder.

1H NMR (CDCl$_3$), δ=13.1 (2H, bs), 11.8 (2H, bs), 10.1 (2H, bs), 7.8 (4H, m), 6.9 (2H, m), 6.7 (2H, m), 5.8 (2H, s), 5.6-5.2 (2H), 4.2 (4H, m), 3.8 (3H, s), 3.6 (4H, m), 3.3-2.8 (8H), 2.2 (6H, s), 1.8-1.2 (8H, m), 1.0 (20H, m). λmax=405 nm; ε=31920 (CHCl$_3$).

MALDI-TOF MS analysis, [M+H+]=985, [M+Na+]=1009.

λmax=405 nm; ε=32000 (CHCl$_3$).

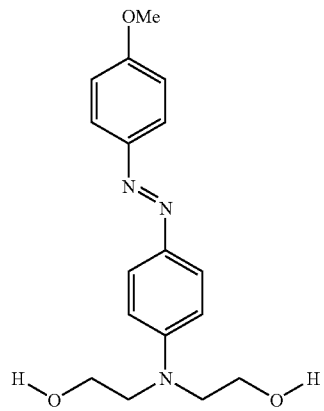

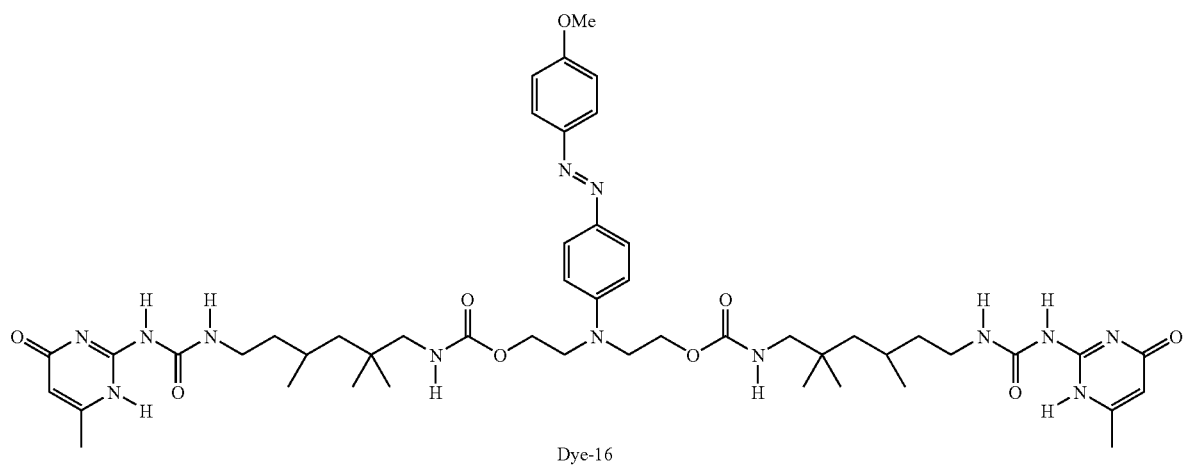

Dye-16

Synthesis Example 17

This example discloses the synthesis of Dye-17.

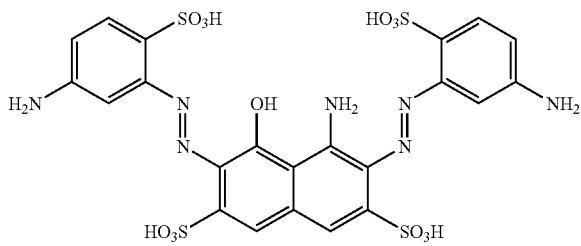

reference dye-5

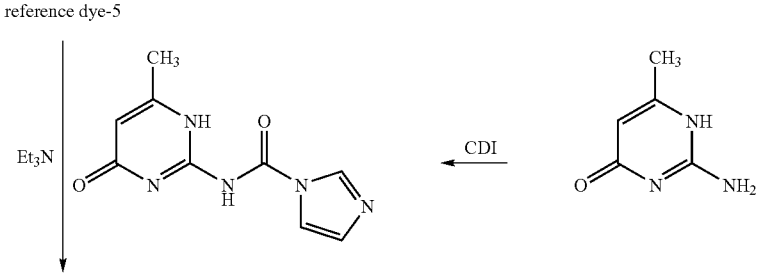

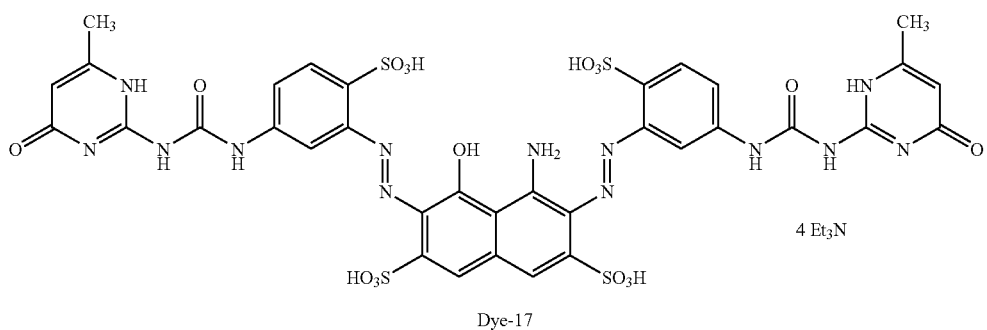

Dye-17

5.9 g (33 mmol) CDI was added to a suspension of 3.8 g (30 mmol) 2-amino-4-hydroxy-6-methylpyrimidine. The reaction is slightly exothermic and the mixture remains a suspension. The mixture is stirred for 30 minutes. 7.2 g of reference dye-5 is dissolved in 50 mL dimethylacetamide at 50° C. by adding 5.6 mL triethylamine. This solution is added to the suspension of CDI activated 2-amino-4-hydroxy-6-methylpyrimidine and the reaction is allowed to continue over night at room temperature. The precipitated mixture of products is isolated by filtration, washed with ethylacetate and dried. The compound was purified using preparative chromatography using a gradient elution from methanol/water 10/90 to methanol/water 90/10, both buffered with 1.05 mL triethylamine and 0.5 mL acetic acid per liter eluent, on a Kromasil C18 (100 A, 10 μm)silica. The chromatography was run on a Prochrom LC80 column at a speed of 150 mL per minute and a gradient elution time of 30 minutes. Dye-17 was isolated with 10% yield and characterized by 1H-NMR spectroscopy and mass spectroscopy.

Synthesis Example 18

This example discloses the synthesis of Dye-21
Synthesis of the Diphthalimide.

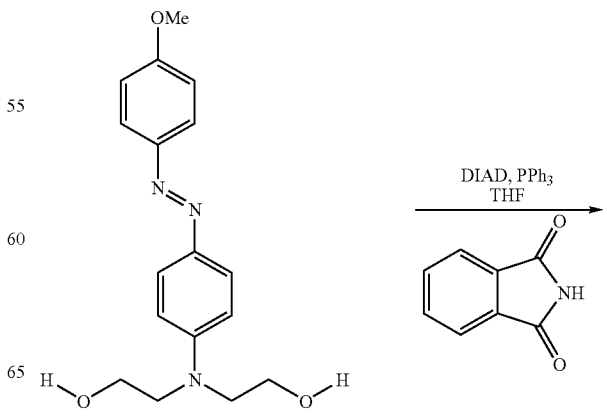

-continued

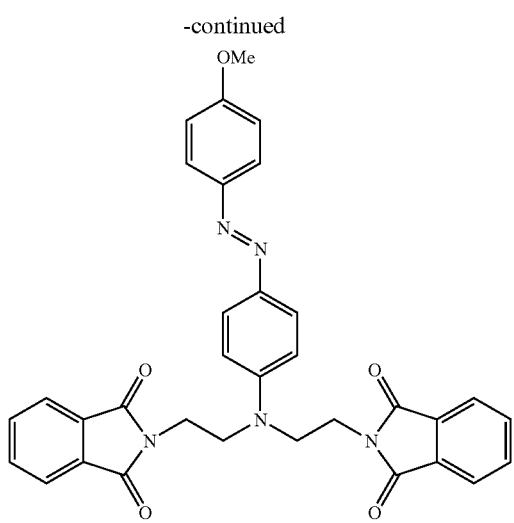

The azodye-diol (1 gram; 3.17 mmol (prepared according to standard procedures) was dissolved in 20 mL of THF together with phthalimide (1.4 gram; 9.5 mmol) and triphenylphosphine (2.4 gram; 9.1 mmol). Diisopropylazodicarboxylate (1.9 gram; 9.4 mmol) in THF was added dropwise to this solution while cooling the mixture in a water bath. Overnight stirring at room temperature yielded a precipitate. Ether was added, stirring was continued for some time and the precipitate was collected by filtration. Yield: 1.43 gram (78%). The diphthalimide was pure according to TLC and NMR analyses.

$^1$H NMR (CDCl$_3$), δ=7.9-7.6 (12H, m), 7.0 (4H, 2), 3.95 (4H, m), 3.9 (3H, s), 3.8 (4H, m).

Synthesis of Dye-21.

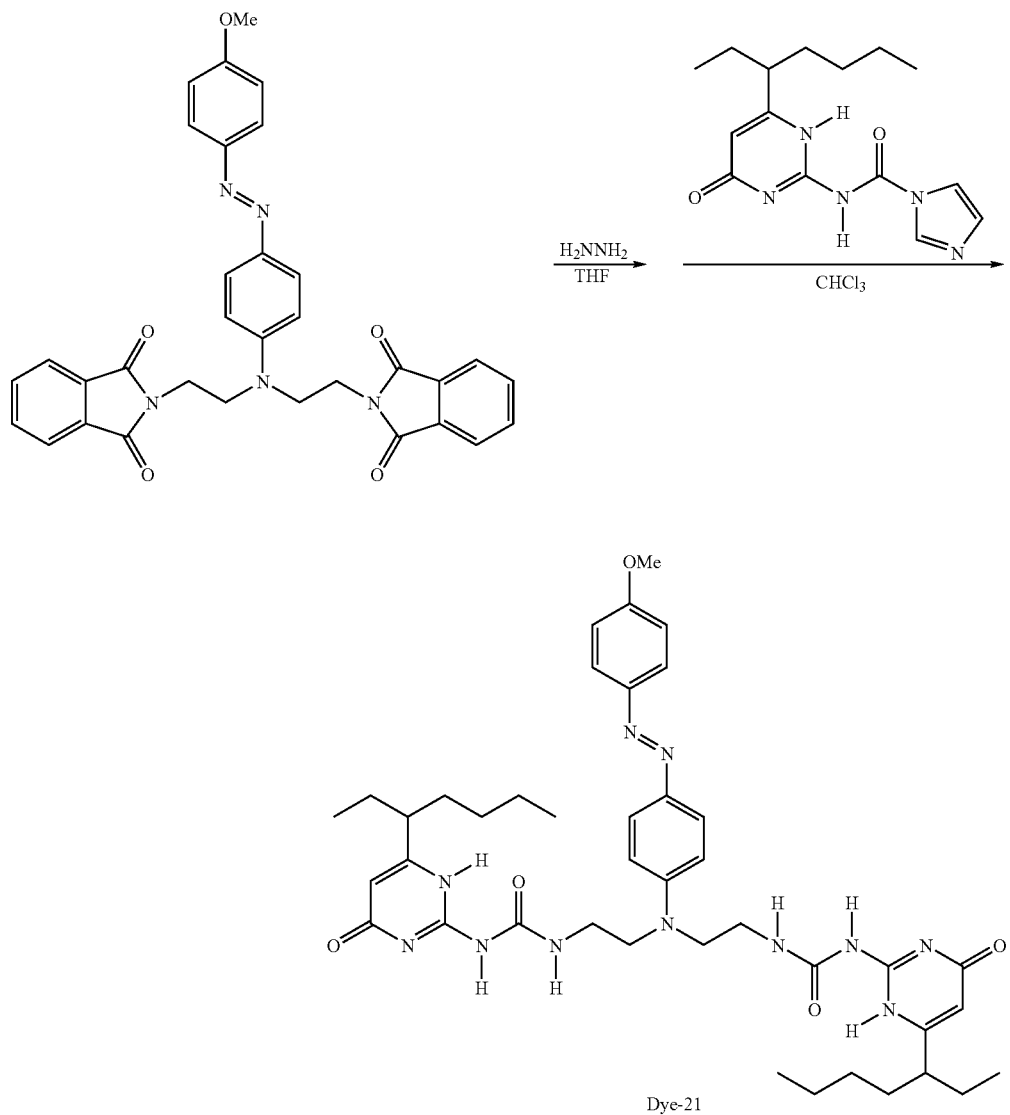

Dye-21

The diphthalimide (1.43 gram; 2.5 mmol) was suspended in 40 mL of boiling THF and hydrazine hydrate (2.6 mL). The suspension developed s into a clear solution and subsequently a white precipitate was formed. After cooling down the mixture it was filtered and the filtrate was concentrated to yield the crude diamine that was used in the next step. The CDI-activated product of (1-ethylpentyl)-isocytosine (2.1 gram, 6.93 mmol) was stirred overnight at room temperature in 50 mL $CHCl_3$ together with the crude diamine (0.87 gram; 2.78 mmol). The mixture was subsequently washed with a HCl solution and a $NaHCO_3$ solution, and thereafter dried and concentrated. The product was precipitated from $CHCl_3$ into methanol and yielded 1.92 gram of Dye-21 as a yellow product (87%).

1H NMR ($CDCl_3$), δ=13.2 (2H, s), 11.9 (2H, s), 10.4 (2H, s), 7.8 (4H, m), 7.0 (4H, m), 5.8 (2H, s), 3.8 (3H, s), 3.7-3.4 (8H, m), 2.3 (2H, m), 1.8-1.5 (8H, m), 1.3 (8H, m), 0.95-0.8 (12H, m).

MALDI-TOF MS, [M+H+]=784.6, [M+Na+]=806.6, [M+K+]=822.6

UV: λmax=408 nm; ε=14000 ($CHCl_3$).

Synthesis Example 19

This example discloses the synthesis of Dye-26

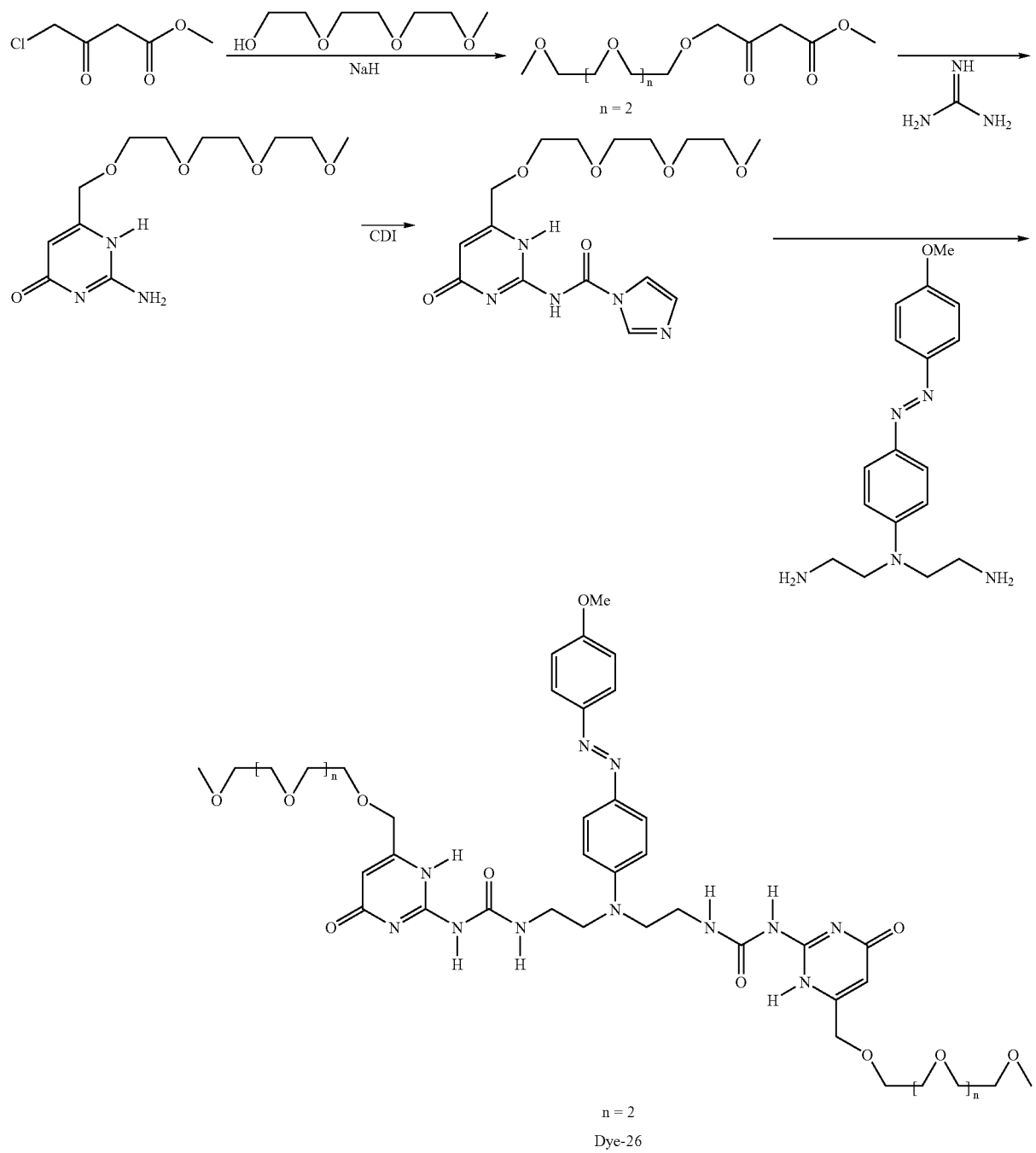

Dye-26

NaH (60%, 1.2 g, 30 mmol) was stirred in 20 mL dry THF under an argon atmosphere. Triethylene glycol (2 g, 12.2 mmol) in 5 mL THF was added dropwise, and after 30 minutes of stirring the β-keto ester (1.8 g, 12 mmol) in 6 mL THF was added dropwise. The mixture was stirred overnight at room temperature, and was thereafter poured into a 10% aqueous solution of acetic acid. Extraction with $CH_2Cl_2$, washing of the organic layer with water and a NaCl solution, drying with $MgSO_4$, filtration and concentration gave the crude β-keto ester oil (2.1 g, 63%) that was used in the next step as isolated. The β-keto ester (2 g, 7.2 mmol) and guanidine carbonate (1.7 g, 18.9 mmol) were boiled in 40 mL of ethanol for 72 hours. The mixture was concentrated, isopropanol was added and the suspension was filtered to remove the excess of guanidine carbonate. The filtrate was concentrated and eluted over a silica column, first using $CHCl_3$ with 4% MeOH to remove contaminations. The isocytosine, a white solid, could be collected by eluting with $CHCl_3$/MeOH (4%) containing 1% triethylamine. Yield: 1.65 g (80%).

The isocytosine (1.65 g, 5.7 mmol) was stripped from possible protic solvents by co-evaporation with toluene and was dissolved in 40 mL of $CHCl_3$ that had been pre-dried over molecular sieves. Carbonyl diimidazole, CDI, (1.7 g, 10.5 mmol) was added and the solution was stirred for 8 hours at room temperature; NMR analysis showed that no isocytosine was present anymore. The solution was washed twice with a saturated NaCl solution, dried with $MgSO_4$, and concentrated to give a white product. Yield of the activated product: 1.9 g (90%). The activated isocytosine (1.16 g, 3.0 mmol) was stirred for three days at room temperature with 4-(4-(N,N-bis-(2-amino ethyl)amine)-phenylazo)-anisole (0.45 g, 1.44 mmol) in 25 mL of $CHCl_3$ under an atmosphere of argon. The mixture was washed with an 1M HCl solution and with a $NaHCO_3$ solution. The organic layer was dried with $Na_2SO_4$ and concentrated to give a yellow solid.

$^1$H NMR ($CD_3SOCD_3$), 67 =11.0-10.0 (6H, bs), 7.7 (4H, m), 7.0 (4H, m), 5.8 (2H, s), 4.2 (4H, s), 3.8 (4H, s), 3.6-3.3 (31H, m), 3.2 (6H, s).

MALDI-TOF MS $C_{43}H_{61}N_{11}O_{13}$, $[M+H^+]$=940.3, $[M+Na^+]$=962.3, $[M+K^+]$=978.3, $[M+2Na^+-H^+]$=984.3, $[M+K^++Na^+-H^+]$=1000.3.

UV: $\lambda_{max}$ ($CHCl_3$)=404 nm; $\epsilon$=28000.

NMR-data on the intermediate products are in agreement with the assigned molecular structures.

Synthesis Example 20

This example discloses the synthesis of Dye-27 and Dye-28

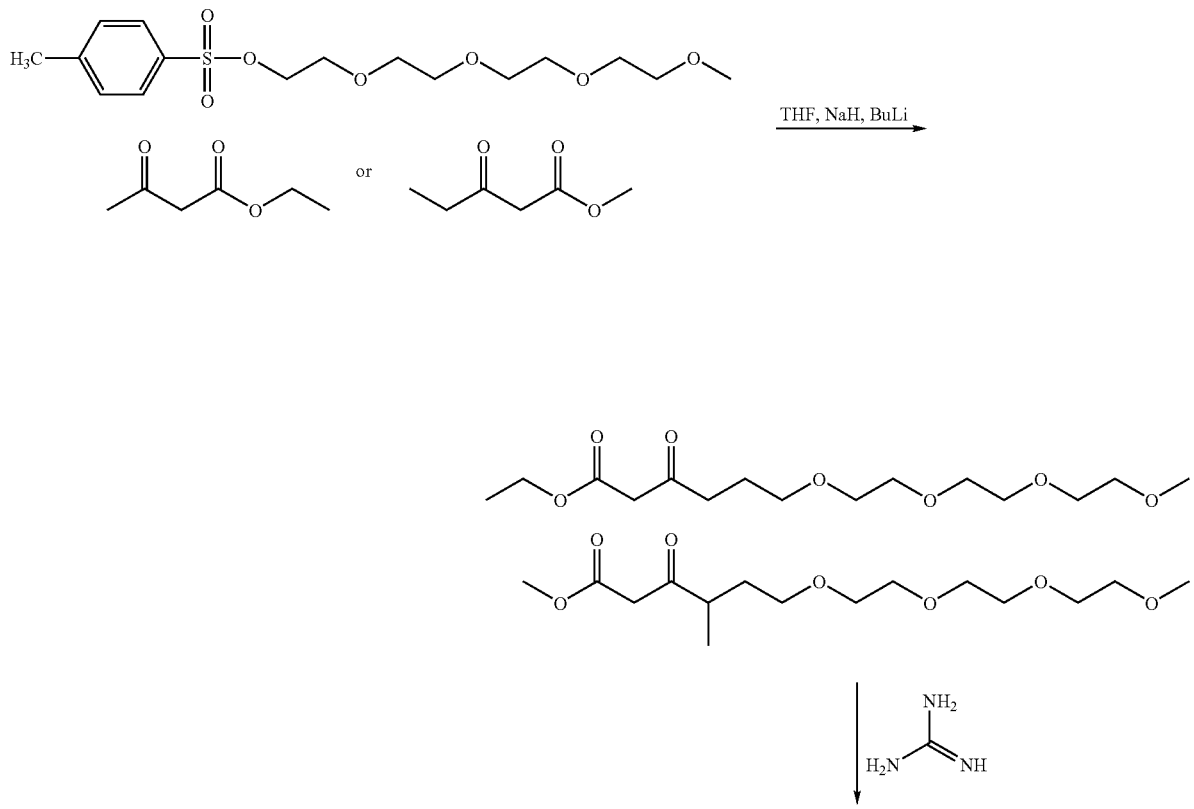

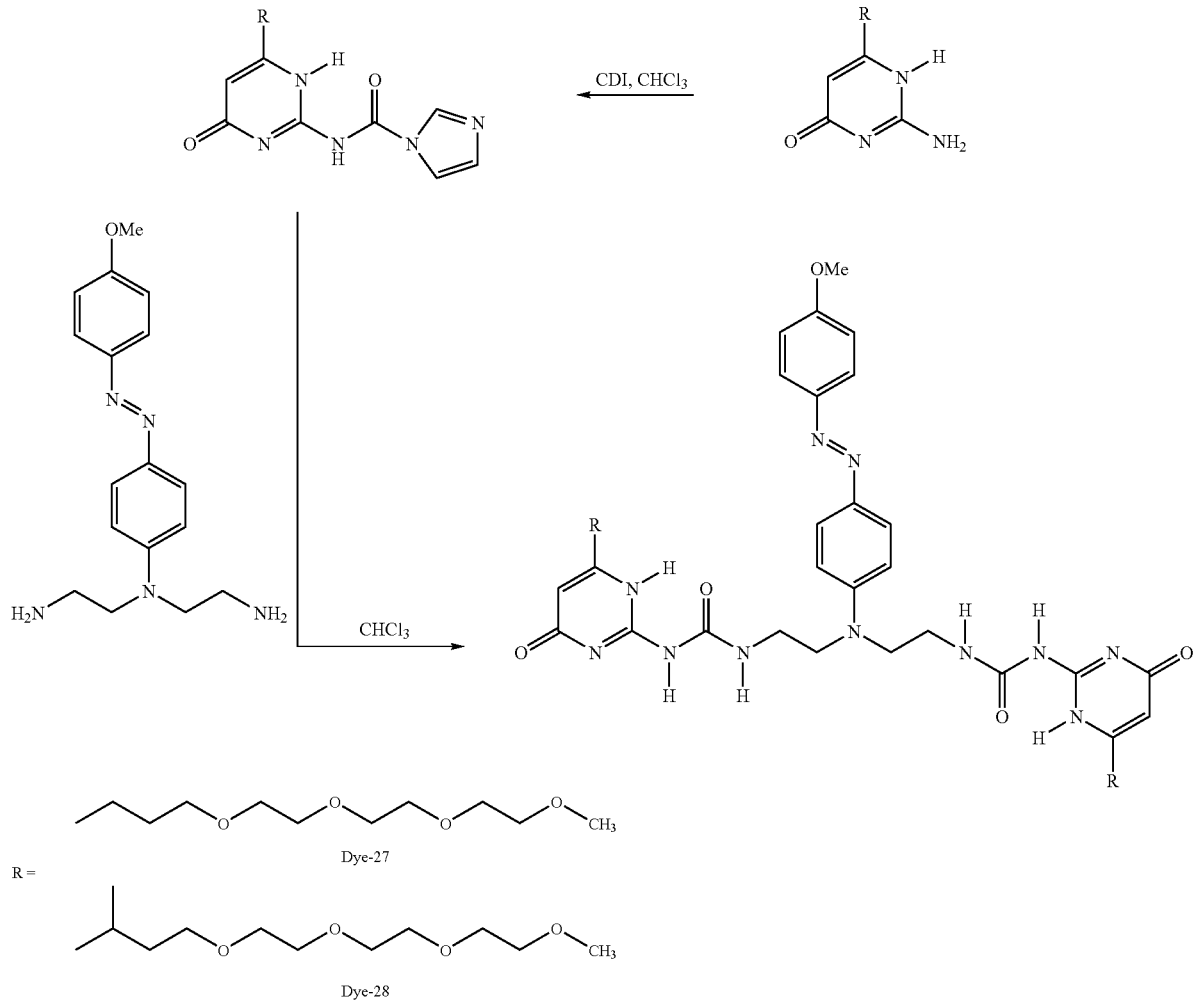

Monomethyl tetraethylene glycol (25.8 g, 124 mmol) was stirred in 35 mL of THF, 35 mL of water and NaOH (7.1 g, 178 mmol). The mixture was kept under 5° C., while TsCl (21.5 g, 113 mmol) in 35 mL of THF was added dropwise; stirring was continued for an additional 4 hours. $CHCl_3$ was added to the solution, and the mixture was washed twice with a saturated NaCl solution. Drying with $MgSO_4$, filtration and concentration gave 37.2 grams of an oily tosylate (91%).

Dye-27. Ethylacetoacetate (2.0 g, 15.4 mmol) was added dropwise to an ice-cooled suspension of NaH (60%, 0.73 g, 18.3 mmol) in 45 mL of dry THF. After one hour of stirring, n-BuLi in hexanes (1.6 M, 9.5 mL, 15.2 mmol) was added, while maintaining ice-cooling of the reaction mixture. After another hour, the monomethyl tetraethylene glycol tosylate (5 g, 13.8 mmol) in 15 mL of dry THF was added dropwise to the ethylacetoacetate mixture and the suspension was put to reflux for 16 hours. The reaction mixture was poured into water and extracted with $CH_2Cl_2$. The organic layer was washed with a saturated NaCl solution, and dried with $Na_2SO_4$. Silica column chromatography using 5% dimethoxyethane in $CHCl_3$ gave 3.2 g β-keto ester product (72%).

The β-keto ester (1.9 g, 5.9 mmol) and guanidine carbonate (1.35 g, 15 mmol) were boiled in 30 mL of ethanol for 16 hours. The mixture was concentrated and eluted over a silica column, first using $CHCl_3$ with 4% MeOH to remove contaminations. The isocytosine, a white solid, was collected by eluting with $CHCl_3$/MeOH (4%) containing 2% triethylamine. Yield: 0.82 g (44%).

The isocytosine (0.82 g, 2.6 mmol) was co-evaporated with toluene and stirred for 6 hours with CDI (0.55 g, 3.4 mmol) in 20 mL of dry $CHCl_3$ under an argon atmosphere. The mixture was washed twice with a saturated NaCl solution, dried with $Na_2SO_4$ and concentrated.

The activated product (0.8 g, 1.95 mmol) was stirred with 4-(4-(N,N-bis-(2-amino ethyl)amine)-phenylazo)-anisole (0.26 g, 0.83 mmol) in 25 mL of $CHCl_3$. After 24 hours, the solution was washed with a 1M HCl and thereafter with a $NaHCO_3$ solution. Drying with $Na_2SO_4$ was followed by filtration and concentration to yield Dye-27 as a yellow solid. The solid was dissolved in $CHCl_3$ and precipitated into pentane. Yield: 0.77 g (95%).

$^1$H NMR ($CDCl_3$), δ=13.0 (2H, bs), 11.9 (2H, bs), 10.4 (2H, bs), 7.8 (4H, m), 6.9 (4H, m), 5.9 (2H, s), 3.9-3.3 (45H, m), 2.6 (4H, t), 1.9 (4H, t).

MALDI-TOF MS $C_{47}H_{69}N_{11}O_{13}$, $[M+H^+]$=996.5, $[M+Na^+]$=1018.5.

UV: $\lambda_{max}$ ($CHCl_3$)=404 nm; $\epsilon$=15000

NMR-data on the intermediate products are in agreement with the assigned molecular structures.

Dye-28. THF (25 mL) was added to NaH (60%, 0.64 g, 16 mmol) which was previously washed with pentane. Methylpropionylacetate (1.5 g, 11.5 mmol) was added, while the suspension was cooled in an ice bath. After 10 minutes of stirring, n-BuLi in hexanes (2.5 M, 4.8 mL, 12 mmol) was added dropwise. Another 10 minutes of stirring was followed by addition of the monomethyl tetraethyleneglycol tosylate (4.6 g, 12.7 mmol) in 15 mL of THF. The mixture was boiled overnight, and then washed with a 1M HCl solution and a saturated NaCl solution. The β-keto ester was purified by silica column chromatography using consecutively $CHCl_3$/MeOH (2%), and $CHCl_3$/MeOH (4%) containing 2% triethylamine as eluents.

The β-keto ester (1.6 g, 5.0 mmol) and guanidine carbonate (1.15 g, 12.8 mmol) were boiled in 20 mL of ethanol for 16 hours. The mixture was concentrated and eluted over a silica column, first using $CHCl_3$ with 4% MeOH to remove contaminations. The isocytosine was collected as a white solid by eluting with $CHCl_3$/MeOH (4%) containing 2% triethylamine. Yield: 1.36 g (83%).

The isocytosine (1.36 g, 4.1 mmol) was stripped from protic contaminants by co-evaporation with toluene and was dissolved in 25 mL of dry $CHCl_3$. CDI (1.05 g, 6.5 mmol) was added and stirring was maintained overnight under an argon atmosphere. The mixture was washed twice with a saturated NaCl solution, dried with $Na_2SO_4$ and concentrated.

The activated product (1.9 g, 4.5 mmol) was stirred with 4-(4-(N,N-bis-(2-amino ethyl)amine)-phenylazo)-anisole (0.55 g, 1.76 mmol) in 50 mL of dry $CHCl_3$. After 24 hours, the solution was washed with a 1M HCl solution and thereafter with a $NaHCO_3$ solution. Drying with $Na_2SO_4$ was followed by filtration and concentration to give Dye-28 as a yellow solid. The solid was dissolved in $CHCl_3$ and precipitated into pentane, followed by crystallization from ethylacetate. Yield: 1.55 (87%).

$^1$H NMR ($CDCl_3$), δ=13.1 (2H, bs), 11.9 (2H, bs), 10.4 (2H, bs), 7.8 (4H, m), 6.9 (4H, m), 5.9 (2H, s), 3.9-3.3 (45H, m), 2.9 (2H, m), 1.9 (4H, t), 1.3 (6H, d).

MALDI-TOF MS $C_{49}H_{73}N_{11}O_{13}$, [M+H$^+$]=1024.5, [M+Na$^+$]=1046.5.

UV: $\lambda_{max}$ ($CHCl_3$)=404 nm; ε ($CHCl_3$)=16000

NMR-data on the intermediate products are in agreement with the assigned molecular structures.

Synthesis Example 21

This example discloses the synthesis of Dye-29

$MgCl_2$ (16.5 g, 173 mmol) was added to a cooled (−15° C.) mixture of potassium malonate (24.4 g, 144 mmol) and triethylamine (22.5 g, 223 mmol) in 200 mL acetonitrile. After stirring for 2 hours at 10-15° C., ethylhexanoyl chloride (11.2 g, 69 mmol) was added, while maintaining cooling in an ice bath. Overnight stirring at room temperature under an argon atmosphere was followed by evaporation of the solvent, addition of ether and an HCl solution. The organic layer was washed with a bicarbonate solution, dried over $MgSO_4$ and concentrated to give an almost quantitative yield of an oil. This β-keto ethyl ester (6.0 g, 28.0 mmol) was added dropwise to an ice cooled suspension of NaH (60%, 1.32 g, 33 mmol) in 75 mL of dried THF.

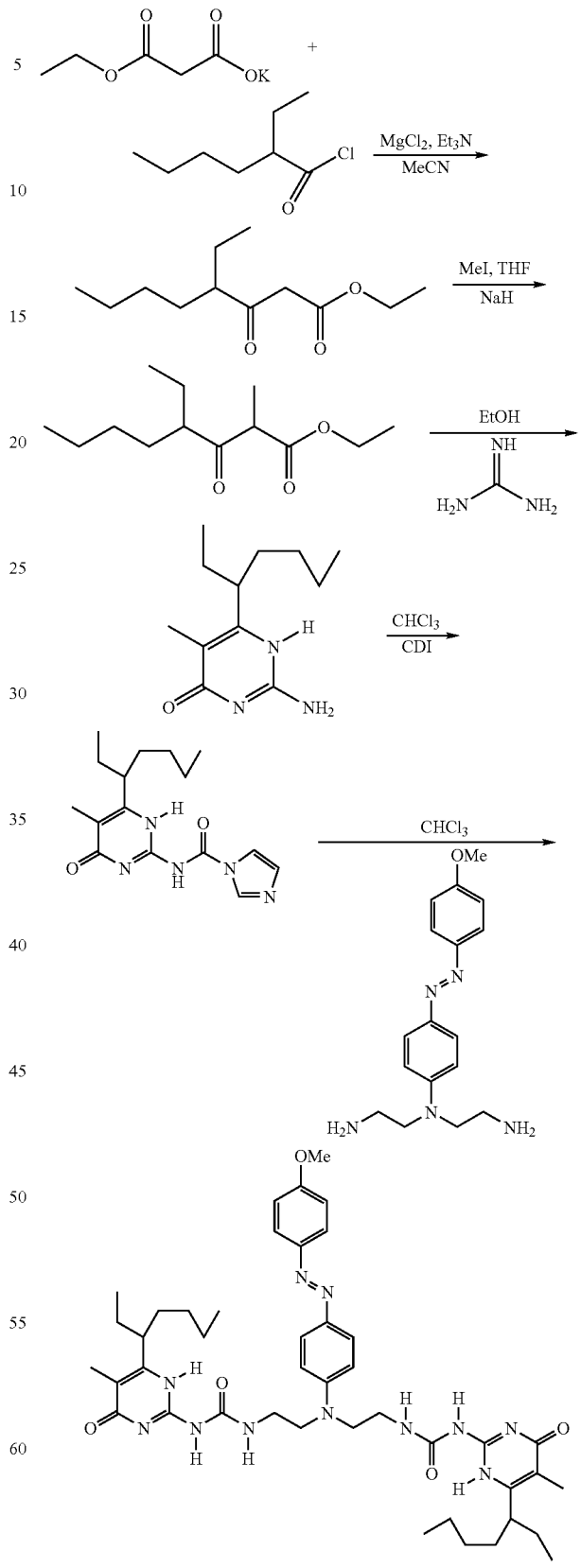

Dye-29

After an hour of stirring, MeI (2.4 mL, 38.5 mmol) was added and the mixture was stirred overnight under an argon atmosphere at 45° C. The product was poured into an aqueous 1M HCl solution and extracted with chloroform. The organic layer was washed with a saturated NaCl solution and dried with Na$_2$SO$_4$. Evaporation of the solvent gave 6.5 grams of an oil. This modified β-keto ethyl ester (11.2 g, 49.1 mmol) and guanidine carbonate (42.2 g, 469 mmol) were put to reflux in 275 mL of ethanol. Reflux was maintained during two days, using a Dean-Stark setup with dried molecular sieves in the receiving arm. Ethanol was removed by evaporation, chloroform was added and the organic solution was washed with a bicarbonate solution. Drying of the solution with MgSO$_4$ was followed by precipitation of the isocytosine into pentane to afford 6.0 grams (55%) of a white solid. The isocytosine (3.0 g, 13.5 mmol) and CDI (3.0 g, 18.5 mmol) were stirred during two hours in 75 mL of chloroform at room temperature. The mixture was washed three times with a saturated NaCl solution and then dried with Na$_2$SO$_4$. The activated product (3.9 g, 90%) was ready for use in the next step as NMR-analysis did not show any imidazole or CDI traces. The activated isocytosine (3.9 g, 12.3 mmol) was stirred overnight with 4-(4-(N,N-bis-(2-amino ethyl)amine)-phenylazo)-anisole (1.47 g, 4.7 mmol) in 120 mL of chloroform. The mixture was consecutively extracted with a 1 M aqueous HCl solution and a bicarbonate solution, followed by drying over Na$_2$SO$_4$. Evaporation of the solvent was followed by precipitation from chloroform into methanol, and then from chloroform into pentane to yield 1.5 grams of Dye-29 as a yellow solid.

$^1$H NMR (CDCl$_3$), δ=13.0 (2H, bs), 11.9 (2H, bs), 10.5 (2H, bs), 7.8 (4H, m), 7.0 (2H, m), 6.9 (2H, m), 3.8 (3H, s), 3.7 (4H, m), 3.5 (4H, m), 2.8 (2H, m), 2.1 (6H, s), 1.8-1.5 (8H, m), 1.4-1.2 (8H, m), 0.9 (12H, m).

MALDI-TOF MS C$_{43}$H$_{61}$N$_{11}$O$_5$, [M+H$^+$]=812.1, [M+Na$^+$]=834.1.

UV: λ$_{max}$ (CHCl$_3$)=410 nm; ε (CHC$_3$)=22000

NMR-data on the intermediate products are in agreement with the assigned molecular structures.

Synthesis Example 22

This example discloses the synthesis of Dye-30

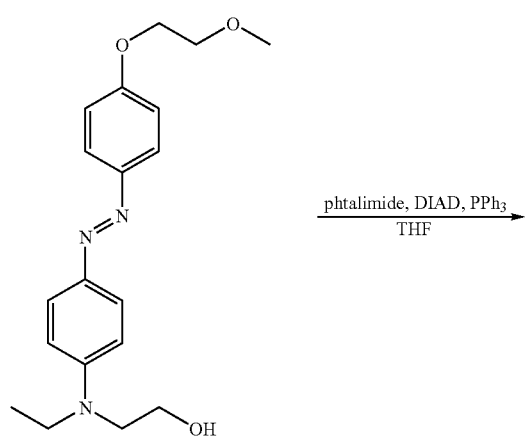

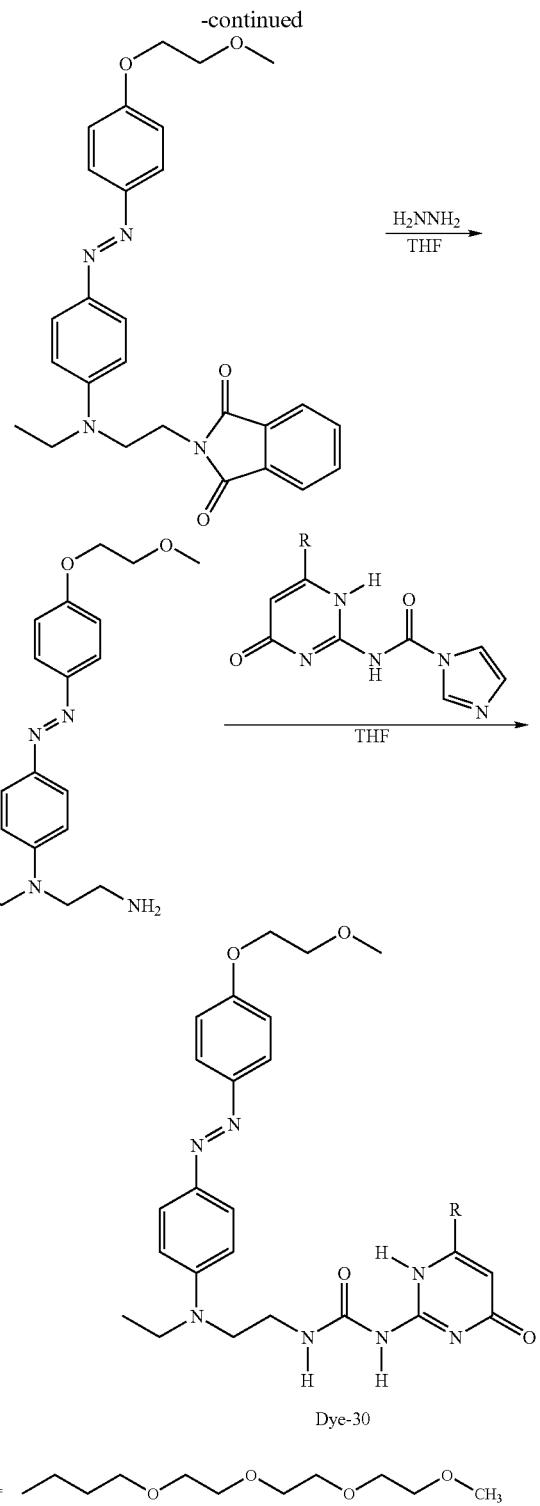

The CDI-activated glycolated isocytosine has been described in Example 11.

The dye alcohol (10 g, 29.2 mmol; prepared according to standard procedures), phthalimide (5.1 g, 34.7 mmol) and triphenylphosphine (9.2 g, 35.1 mmol) were dissolved in 200 mL THF. DIAD (7.1 g, 35.1 mmol) was added dropwise at room temperature. After overnight reaction, the product was concentrated and purified on a silica column (CHCl$_3$/

MeOH, 1%). Stirring in ether/THF 20/1 gave a precipitola that was filtered and dried. Yield: 11.9 g (86%). Hydrazine hydrate (2 g, 40 mmol) was added to the phthalimide dye (11.9 g, 25.2 mmol) in boiling THF. After overnight reflux the white precipitate was removed by filtration. The filtrate was stirred overnight at 40° C. after an additional portion of hydrazine hydrate (1.5 g, 30 mmol) was added. Filtration and co-evaporation of the filtrate with toluene gave the amine product. This amine (1.35 g, 3.9 mmol) and the activated isocytosine (2.2 g, 5.4 mmol) were stirred overnight at room temperature in 20 mL of THF. The solution was concentrated, CHCl$_3$ was added and the organic solution was washed consecutively with 0.01 M HCl, salt and bicarbonate solutions. After drying on MgSO$_4$ the residue was purified by column chromatography on silica using CHCl$_3$/MeOH 1% to 4% as eluent. 1.54 g of Dye-30 was obtained (57%).

$^1$H NMR (CDCl$_3$), δ=13.0 (1H, bs), 11.9 (1H, bs), 10.4 (1H, bs), 7.8 (4H, m), 7.0 (2H, m), 6.8 (2H, m), 5.8 (1H, s), 4.2 (2H, t), 3.8 (2H, m), 3.7-3.4 (26H, m), 2.7 (2H, t), 2.0 (2H, m), 1.3 (3H, t).

MALDI-TOF MS C$_{34}$H$_{49}$N$_7$O$_8$, [M+H$^+$]=684.1, [M+Na$^+$]=706.1.

UV: λ$_{max}$ (CHCl$_3$)=413 nm; ε=17000

NMR-data on the intermediate products are in agreement with the assigned molecular structures.

Synthesis Example 23

This example discloses the synthesis of Dye-31

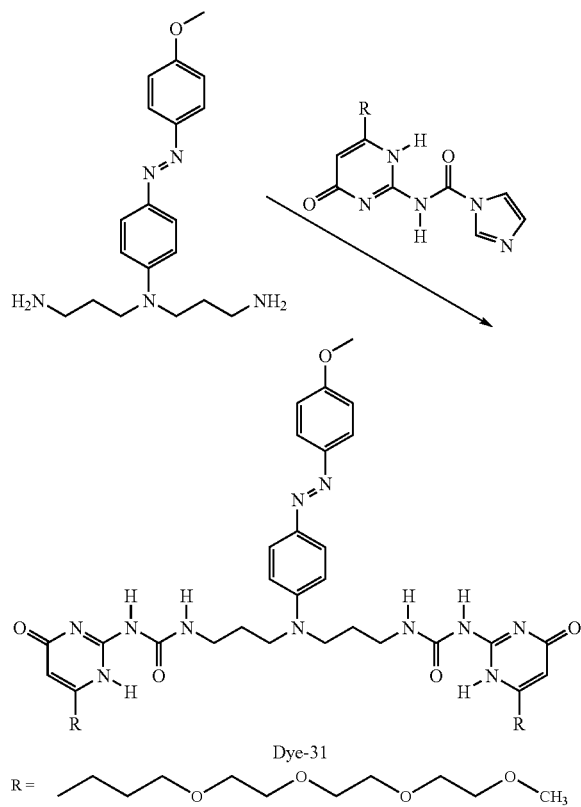

Dye-31

The CDI-activated glycolated isocytosine has been described in Example 11. The diamine (0.7 g, 2.1 mmol) and the CDI-activated isocytosine (2.0 g, 4.9 mmol) were stirred overnight in 20 mL of THF at room temperature under an argon atmosphere. Chloroform was added and the mixture was washed with a 0.01 M HCl solution and a saturated bicarbonate solution. The organic phase is dried over Na$_2$SO$_4$, filtered and concentrated under reduced pressure. The residue is purified by column chromatography over silica using CHCl$_3$/MeOH (2%) as eluent to yield 0.95 g of pure Dye-31.

$^1$H NMR (CDCl$_3$), δ=13.2 (1H, s), 13.0 (1H, s), 11.9 (1H, s), 11.7 (1H, s), 10.2 (1H, s), 10.0 (1H, s), 7.8 (4H, m), 7.0 (2H, m), 6.8 (2H, m), 5.8 (1H, s), 5.7 (1H, s), 3.9 (6H, s), 4.0-3.3 (39H, m), 3.1 (2H, m), 2.5 (4H, m), 2.1 (2H, m), 1.8 (4H, m).

MALDI-TOF MS C$_{49}$H$_{73}$N$_{11}$O$_{13}$, [M+H$^+$]=1024.4, [M+Na$^+$]=1046.4.

UV: λ$_{max}$ (CHCl$_3$)=418 nm; ε=24000

Synthesis Example 24

This example discloses the synthesis of Reference Dye-6

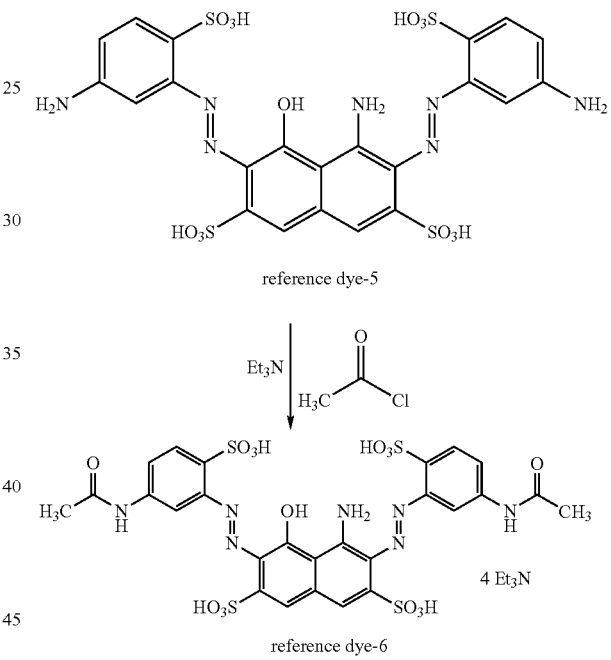

0.9 g (11 mmol) acetyl chloride in 5 mL dimethylacetamide was added dropwise at 35° C. to a suspension of 3.6 g (5 mmol) of reference dye-5 and 2.8 mL (20 mmol) triethylamine in 50 mL dimethylacetamide. The reaction is slightly exothermic but remains a suspension. The reaction is allowed to continue over night at room temperature. The precipitated compound is isolated by filtration and washed with ethyl acetate. Reference dye-6 is re-suspended in 25-mL ethyl acetate, isolated by filtration and dried. From the combined filtrates, a second crop precipitates and is isolated by filtration and washed with methylene chloride. The two fractions were combined yielding 4.2 g of reference dye-6 (70%). Reference dye-6 was characterized by $^1$H-NMR spectroscopy and mass spectroscopy.

INK-JET EXAMPLES

In the Ink-jet Examples below the characteristics of self-assembling dyes according to formula (I) are investigated.

Ink-jet Example 1
In this example a comparison is made between the light-fastness characteristics of some invention dyes and some reference dyes. The following compounds were involved:
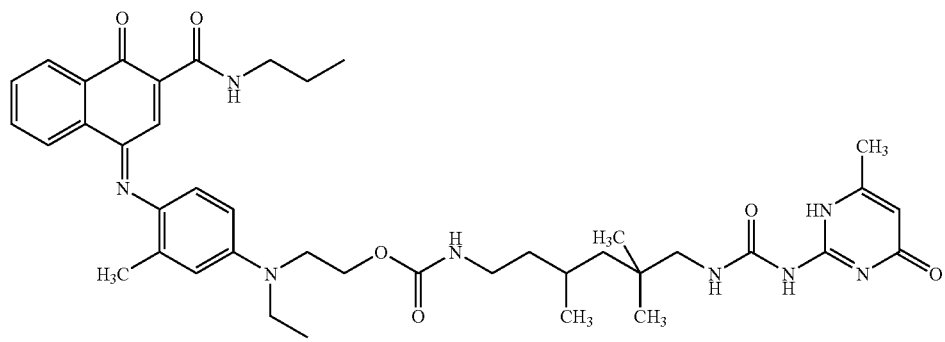
invention dye-8
reference dye-1
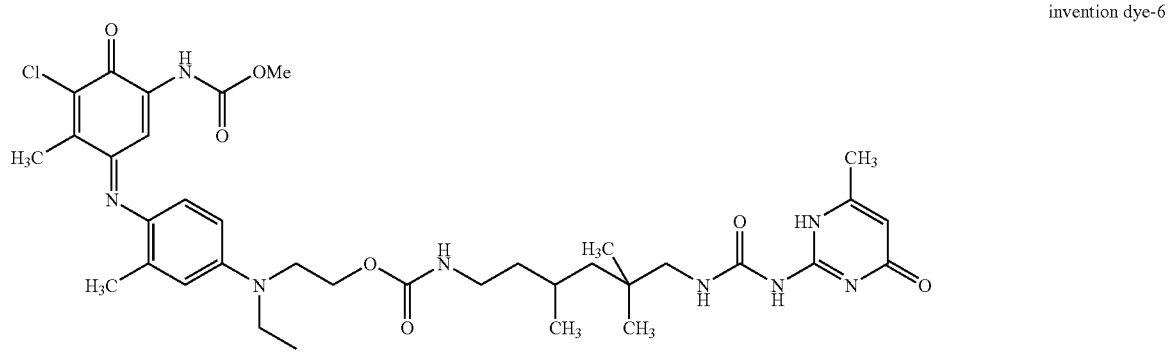
invention dye-6
reference dye-2

-continued invention dye-9
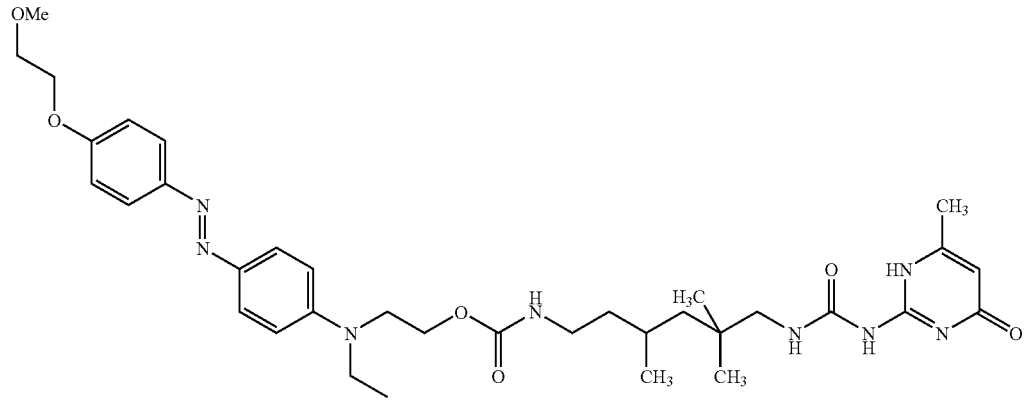

reference dye-3
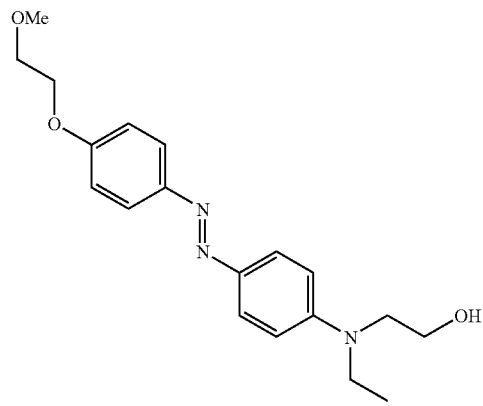

invention dye-7
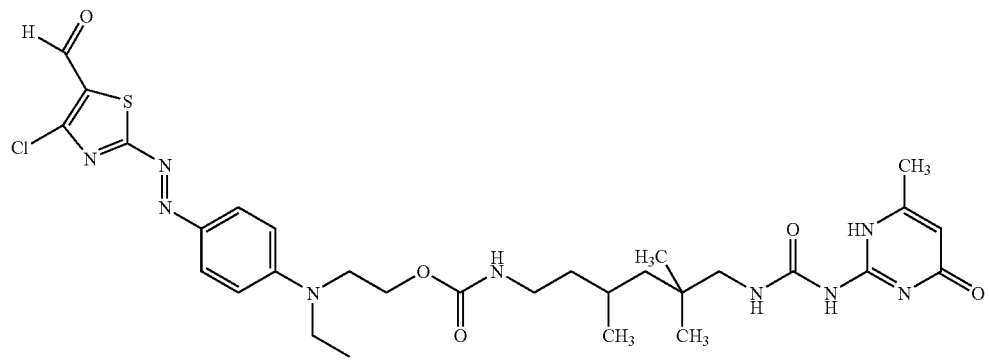

reference dye-4
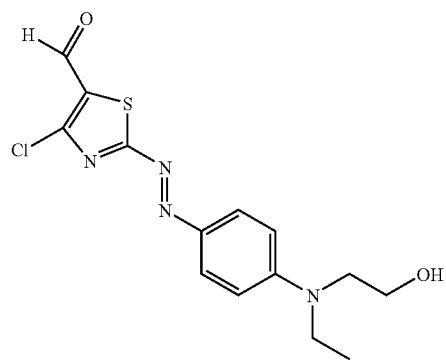

Both reference and invention dyes were dissolved in 2-butanone as a 0.015 molar solution. Samples of 5 mL of the dye solutions were diluted with 5 mL methanol. From each sample, 20 μl of each solution was spotted on a Polar DTR receiver (trademark from AGFA) using an Anachem SK233 apparatus. Each sample was spotted 5 times and the average density value was taken as initial density for each dye at the start of the light-fastness test. The spotted samples were exposed during 8 hours using a Xenon-apparatus (Xenotest 150, equipped with a 7IR-filter, working in indoor mode). After one, two, four and eight hours, the density was measured again and the average density of the five spots was taken as the residual density. The percentage residual density is expressed as (residual density/initial density)×100. The results are summarized in Table 2.

TABLE 2

| Dye | 1 h exposure % residual density | 2 h exposure % residual density | 4 h exposure % residual density | 8 h exposure % residual density |
| --- | --- | --- | --- | --- |
| Invention dye-8 | 86 | 78 | 73 | 42 |
| Reference dye-1 | 75 | 60 | 36 | 21 |
| Invention dye-6 | 92 | 89 | 80 | 61 |
| Reference dye-2 | 90 | 71 | 58 | 34 |
| Invention dye-9 | 98.5 | 97 | 77 | 63 |
| Reference dye-3 | 94 | 81 | 58 | 39 |
| Invention dye-7 | 99 | 87 | 77 | 56 |
| Reference dye-4 | 89 | 73 | 58 | 33 |

The results shown in Table 2 clearly show that use of the self-assembling dyes, according to the present invention, in ink compositions results in significantly higher light-fastness of ink-jet images.

Ink-jet Example 2

In this example a comparison is made between the light-fastness characteristics of some invention dyes and some reference dyes. The following compounds were involved:

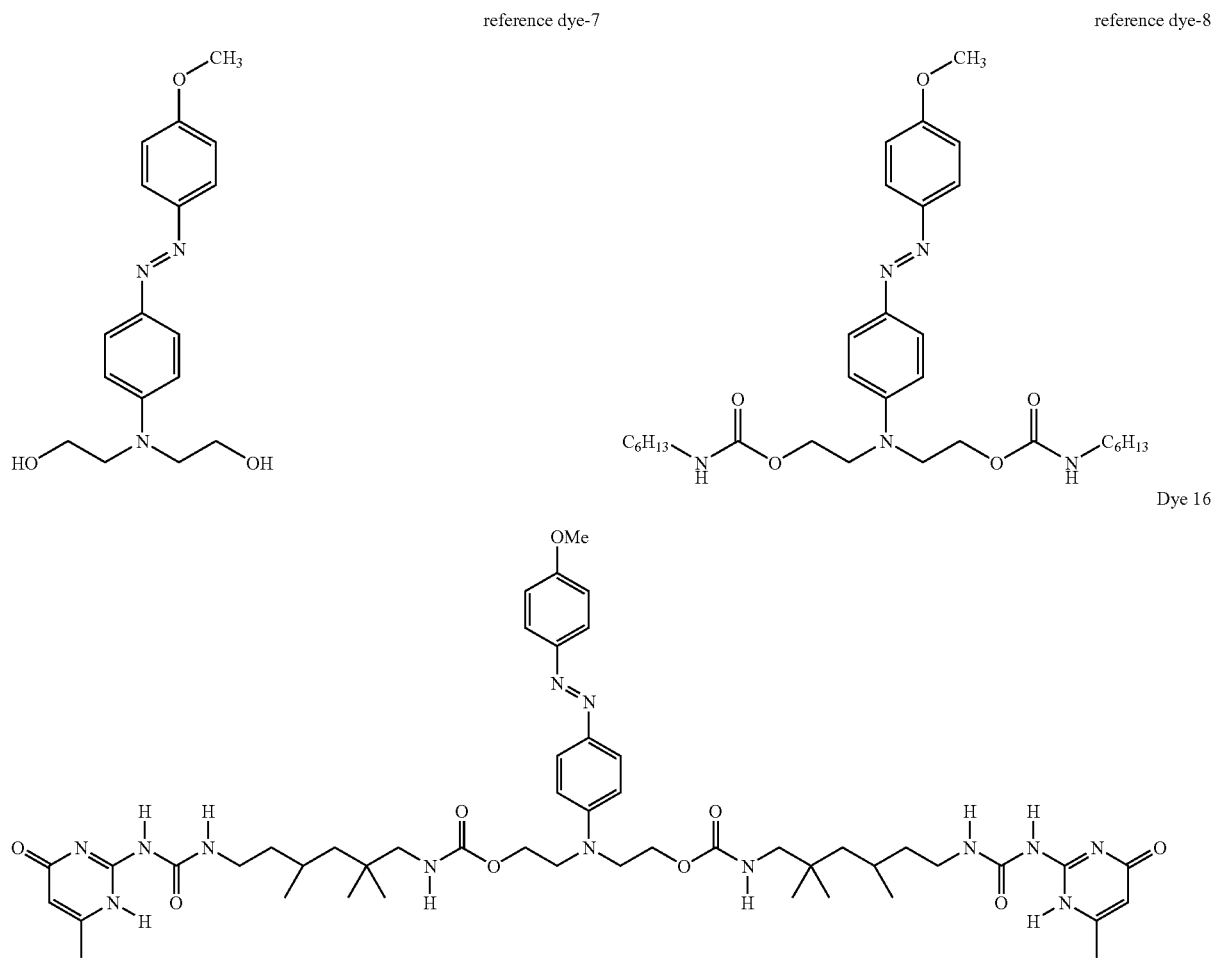

Both reference compounds and the invention dye were dissolved in CH$_2$Cl$_2$/2-methoxypropanol (1/1). Reference dye-7 was dissolved as a 0.25% solution (w/v). The reference dye-8 and the invention dye-16 were dissolved as a 0.5% solution (w/v). 1 mL of the samples was diluted with 0.75 mL 2-methoxypropanol and 0.75 mL CH$_2$Cl$_2$. A second sample of 1 mL was diluted with 1.75 mL 2-methoxypropanol and 2 mL CH$_2$Cl$_2$. For each sample 10 μl was spotted on a Polar DTR receiver (trademark from AGFA). Each sample was spotted 5 times and the average value was taken as the initial density for each dye at the start of the light-fastness test. The spotted samples were exposed during 8 hours using a Xenon-apparatus (Xenotest 150, equipped with a 7IR-filter, working in indoor mode). After one, two, four and eight hours, the density was measured again and the average density of five spots was taken as the residual density. The percentage residual density is expressed as (residual density/initial density)×100. The results are summarized in Table 3 and represent the percentages for the initial samples. The percentage residual density for both the initial samples and the diluted samples showed the same degradation rate.

TABLE 3

| Dye | 1 hr exposure % residual density | 2 hrs exposure % residual density | 4 hrs exposure % residual density | 8 hrs exposure % residual density |
|---|---|---|---|---|
| Invention dye-16 | 100 | 100 | 100 | 90 |
| Reference dye-7 | 100 | 95 | 82 | 68 |
| Reference dye-8 | 100 | 100 | 95 | 75 |

The results shown in Table 3 clearly show that ink compositions with self-assembling dyes, according to the present invention, containing a multiple hydrogen bonding moiety, have a significantly higher light-fastness.

Ink-jet Example 3

In this example a comparison is made between the light-fastness characteristics of some invention dyes and some reference dyes. The following compounds were involved:

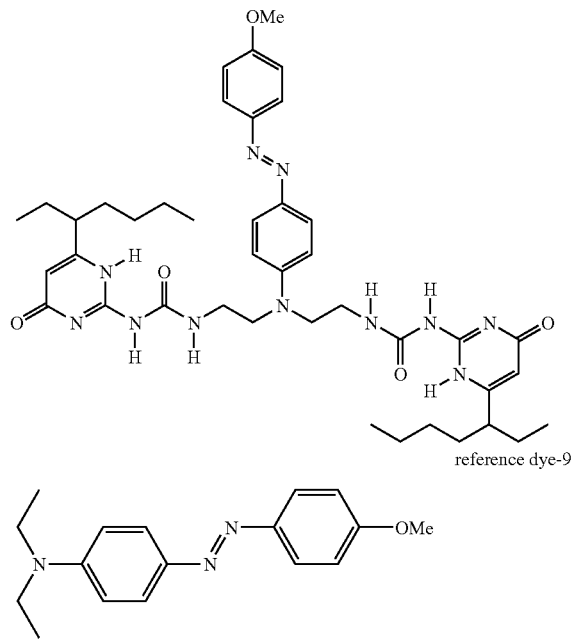

Dye 21 reference dye-9

Both reference dye-9 and the invention Dye-21 were dissolved in $CH_2Cl_2$/2-methoxypropanol (1/1). Reference dye-9 was dissolved as a 0.25% solution (w/v). The invention Dye-21 was dissolved as a 0.5% solution (w/v). 1 mL of the samples was diluted with 0.75 mL 2-methoxypropanol and 0.75 mL $CH_2Cl_2$. A second sample of 1 mL was diluted with 1.75 mL 2-methoxypropanol and 2 mL $CH_2Cl_2$. For each sample 10 μl was spotted on a Polar DTR receiver (trademark from AGFA). Each sample was spotted 5 times and the average value was taken as the initial density for each dye at the start of the light-fastness test. The spotted samples were exposed during 8 hours using a Xenon-apparatus (Xenotest 150, equipped with a 7IR-filter, working in indoor mode). After one, two, four and eight hours, the density was measured again and the average density of five spots was taken as the residual density. The percentage residual density is expressed as (residual density/initial density)×100. The results are summarized in Table 4 and represent the percentages for the initial samples. The percentage residual density for both the initial samples and the diluted samples showed the same degradation rate.

TABLE 4

| Dye | 1 hr exposure % residual density | 2 hrs exposure % residual density | 4 hrs exposure % residual density | 8 hrs exposure % residual density |
|---|---|---|---|---|
| Invention dye-21 | 100 | 100 | 100 | 100 |
| Reference dye-9 | 92 | 85 | 77 | 55 |

The results shown in Table 4 clearly show that ink compositions with self-assembling dyes according to the present invention, containing a multiple hydrogen bonding moiety, have a significantly higher light-fastness.

Ink-jet Example 4

This example deals with ink preparation and the evaluation of some physical properties.

Solubility.

A 5% solution of Dye-6, Dye-7 and Dye-9 in butyl lactate, ethyl lactate, diacetone alcohol, propylene glycol methyl ether and tripropylene glycol methyl ether were prepared by adding the dyes to the solvents and sonicating the suspension for one hour. Clear solutions were obtained. Reference magenta dye RM1 (Table 7) was only partially soluble under the same conditions; reference cyan dye RC1 (Table 7) was soluble in butyl lactate (5%) but only partially soluble in the other solvents. Reference yellow dye RY1 (Table 7) was only soluble in methoxypropyl acetate and N-methyl pyrrolidinone.

Inks.

Table 5 shows the basic formulation, which the dyes were assessed in. The ink raw materials were placed into a plastic bottle and sonicated for one hour. The inks were then filtered to 1 μm and the physical properties measured. Table 6 shows the physical property measurements for each ink. The dyes according to the invention have similar physical ink properties and the filtration times are all good. Generally a filtration time of less than 45 seconds is expected for a dye-based ink.

TABLE 5

| Ink | % Composition w/w |
|---|---|
| Dye (Dye-6; Dye-7) | 3 |
| Vinyl chloride/vinyl acetate copolymer UCAR VAGD | 2 |
| Butyl lactate | 95 |
| Dye (Dye-9) | 3 |
| Vinyl chloride/vinyl acetate copolymer UCAR VAGD | 2 |
| Butyl lactate | 75 |
| N-Methyl Pyrrolidone | 20 |

Priming and Loading.

Inks Ink 1-6 (see table 7 for reference dyes) were tested under standard operating conditions in a Trident UltraJet printhead. The standard conditions are defined as:
a. 150V printhead driver
b. printhead temperature=25° C.
c. sub-pulse off
d. 354 dpi The results obtained show that all inks are easy to load and prime, and achieve good wetting of the internal architecture of the printhead. No visible air entrapment is noticed. Initial start-up is almost immediate and all channels work after maximum 4 primes. The print quality is very good on AGFA Outdoor Material (Polar DTR receiver; trademark from AGFA) and good on polyester (Melinex 347) and PVC substrates.

TABLE 6

|  | Ink1/Dye-6 Cyan | Ink2/Dye-7 Magenta | Ink3/RM1 Magenta | Ink4/RC1 Cyan | Ink5/Dye-9 Yellow | Ink6/RY1 Yellow |
|---|---|---|---|---|---|---|
| Viscosity (mPa · s) | 7.70 | 8.24 | 7.15 | 8.27 | 8.44 | 7.56 |
| Surface Tension dynes/cm | 31.5 | 31.5 | 31.5 | 31.5 | 31.5 | 30 |
| Filtration Performance[1] | 27 sec. | 26 sec. | 29 sec. | 28 sec. | 33 | 33 |

[1] the filtration performance is the time taken to filter 15 mL of ink through a one μm filter paper using a vacuum of 200 mm Hg.

TABLE 7

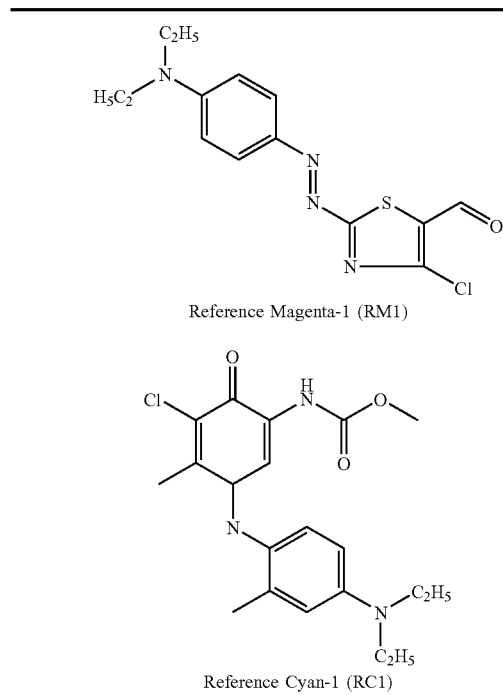

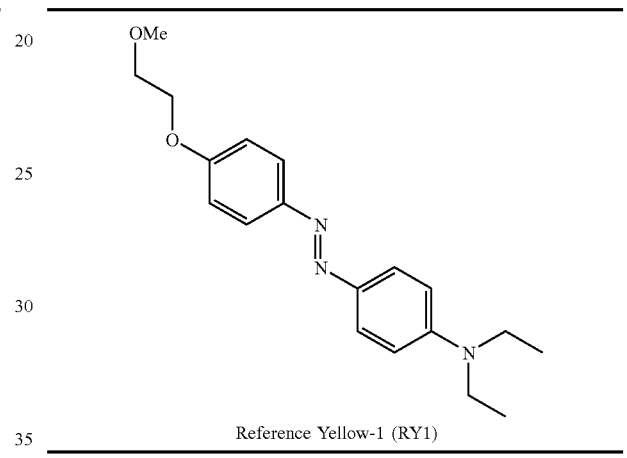

TABLE 7-continued

Ink-jet Example 5

A 0.02 M solution of reference dye-5, reference dye-6 and invention dye-17 were dissolved in water/MeOH 90/10 and diluted twice and five times. The solutions were spotted onto an AGFA POLAR DTR outdoor medium and exposed to Xenon light for eight hours. The % density loss at density 1 was measured after eight hours exposure. The results are summarized in Table 8.

TABLE 8

| Sample | % density loss after 8 hours exposure at density 1 |
|---|---|
| invention dye-17 | 1% |
| reference dye-6 | 5% |
| reference dye-5 | 20% |

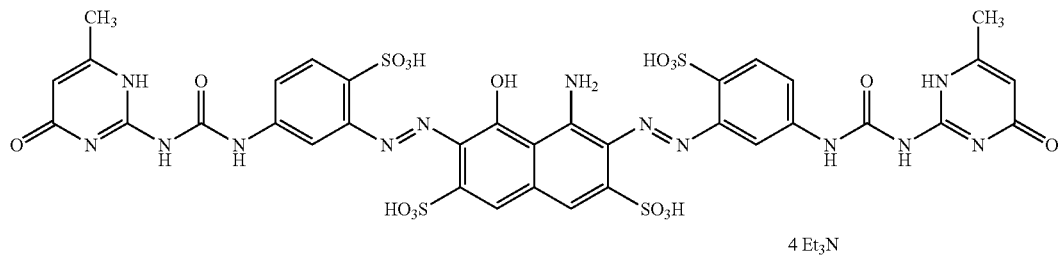

TABLE 8-continued

| Sample | % density loss after 8 hours exposure at density 1 |
|---|---|

Dye 17

[Structure of Reference dye-5: naphthalene core with OH, $NH_2$, two $SO_3H$ groups, bearing two azo linkages to phenyl rings each substituted with $SO_3H$ and $NH_2$, and with $H_2N$/$NH_2$ groups]

Reference dye-5

[Structure of Reference dye-6: naphthalene core with OH, $NH_2$, two $SO_3H$ groups, bearing two azo linkages to phenyl rings each substituted with $SO_3H$ and an acetamido ($H_3C-C(O)-NH-$) group]

Reference dye-6

This example clearly illustrates that the introduction of a self-assembling unit gives superior light fastness as compared to both the parent amino dye and the acetylated reference dye.

Ink-jet Example 6

0.02 M solutions of the invention dyes summarized in Table 11 and reference dye-9 were prepared in $CH_2Cl_2$/MeOH/ethyl lactate 50/40/10 and diluted twice, four times, eight times and sixteen times. All solutions were sprayed onto an AGFA POLAR DTR outdoor medium, resulting in a density wedge. All samples were exposed to Xenon light for eight hours and the percentage density loss after eight hours exposure was measured at density 1. All results are summarized in Table 9.

TABLE 9

| Compound | R1 | R2 | % density loss at density 1 after eight hours Xenon exposure |
|---|---|---|---|
| invention dye-21 | $CH_3(CH_2)_3CHCH_2CH_3$ | H | 24% |
| invention dye-29 | $CH_3(CH_2)_3CHCH_2CH_3$ | $CH_3$ | 29% |
| invention dye-27 | $-(CH_2)_3O(CH_2CH_2O)_3CH_3$ | H | 11% |
| invention dye-25 | $-CH_2O(CH_2CH_2O)_3CH_3$ | H | 10% |
| invention dye-28 | $-CH(CH_3)CH_2CH_2O(CH_2CH_2O)_3CH_3$ | H | 8% |
| reference dye-9 | — | — | 51% |

(comparative)

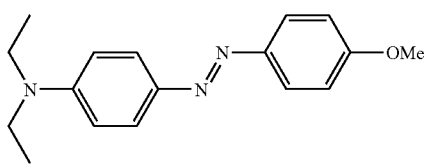

TABLE 9-continued

| Compound | R1 | R2 | % density loss at density 1 after eight hours Xenon exposure |
|---|---|---|---|
| Reference dye-9 | | | |

[Structure of Reference dye-9 shown]

From the results in Table 9 it is clear that the introduction of self-assembling units on the basic chromophore group significantly increases the light-fastness of the dyes.

Having described in detail preferred embodiments of the current invention, it will now be apparent to those skilled in the art that numerous modifications can be made therein without departing from the scope of the invention as defined in the following claims.

All references, including publications, patent applications, and patents, cited herein are hereby incorporated by reference to the same extent as if each reference were individually and specifically indicated to be incorporated by reference and were set is forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A self-assembling dye according to

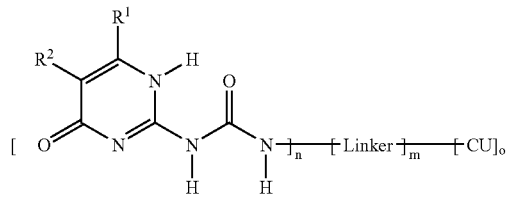

Formula (I)

wherein
Linker represents any linking group containing at least one carbon, nitrogen, silicon, phosphorous, sulfur or oxygen atom;
CU means any chromophore group with an absorption maximum between 200 nm and 2000 nm
n and o are the same or different and are integers having a value of at least 1; m can be zero or any integer having a value of at least 1;
$R^1$ and $R^2$ are the same or different and represent hydrogen, a halogen, a substituted or unsubstituted alkoxy group, a substituted or unsubstituted thioalkoxy group, a substituted or unsubstituted sulphoxy group, a substituted or unsubstituted suiphone group, a substituted or unsubstituted amino group, a nitrile group, a substituted or unsubstituted, saturated or unsaturated alkyl group, a substituted or unsubstituted acyl group, a substituted or unsubstituted sulphonyl group, a substituted or unsubstituted phosphoryl group, a substituted or unsubstituted aryl group, a substituted or unsubstituted aralkyl group, a heterocyclic group, a chromophore group, wherein said chromophore group CU is a dye selected from the group consisting of an azo dye with a molar extinction coefficient larger than $10^3$ $l.mol^{-1}cm^{-1}$, an anthraquinone dye, a (poly)methine dye, an azomethine dye, a disazo dye, a carbonium dye, a styryl dye, a stilbene dye, a phthalocyanine dye, a coumarin dye, an aryl-carbonium dye, a nitro dye, a naphtholactam dye, a dioxazine dye, a flavin dye and a formazan dye; and wherein said Linker is selected from the group consisting of a substituted or unsubstituted, saturated or unsaturated aliphatic group, a substituted or unsubstituted alicyclic hydrocarbon group, a substituted or unsubstituted aromatic group and a substituted or unsubstituted heteroaromatic group.

2. A self-assembling dye according to claim 1, wherein said chromophore group CU is a chromophore group with an absorption maximum between 300 nm and 1200 nm.

3. A self-assembling dye according to claim 1, wherein said chromophore group CU is a chromophore group with an absorption maximum between 380 nm and 850 nm.

4. A self-assembling dye according to claim 1, wherein the association constant $K_{ass}$ of the self-assembling reaction, determined by $^1$H-NMR in $CDCl_3$, is at least 2.5 $M^{-1}$.

5. A self-assembling dye according to claim 4 wherein said association constant $K_{ass}$ is at least $10^2$ $M^{-1}$.

6. A self-assembling dye according to claim 4 wherein said association constant $K_{ass}$ is at least $10^5$ $M^{-1}$.

7. A self-assembling dye selected from the group consisting of

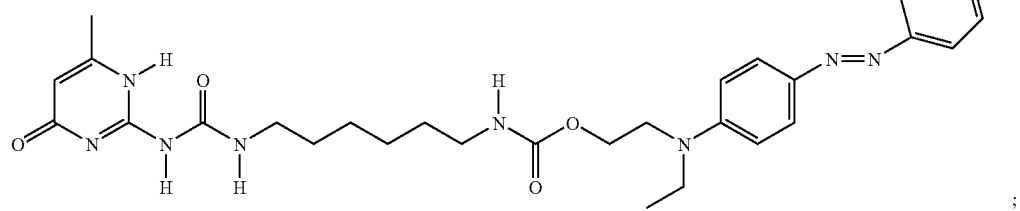

;

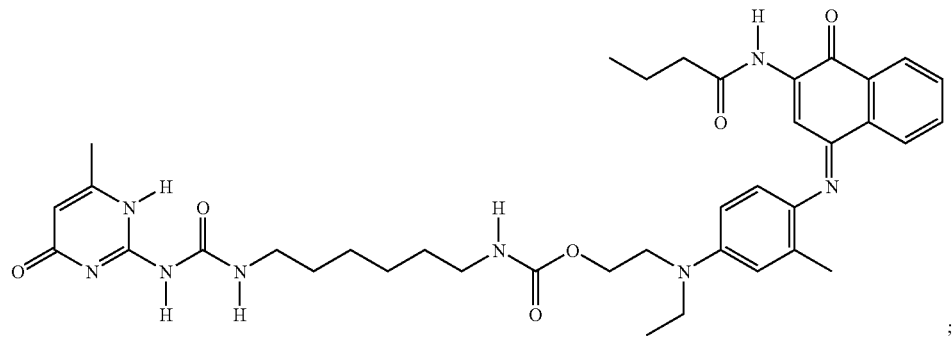

;

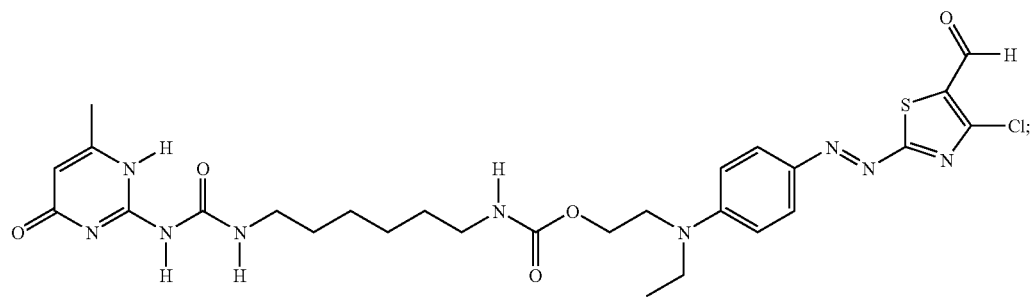

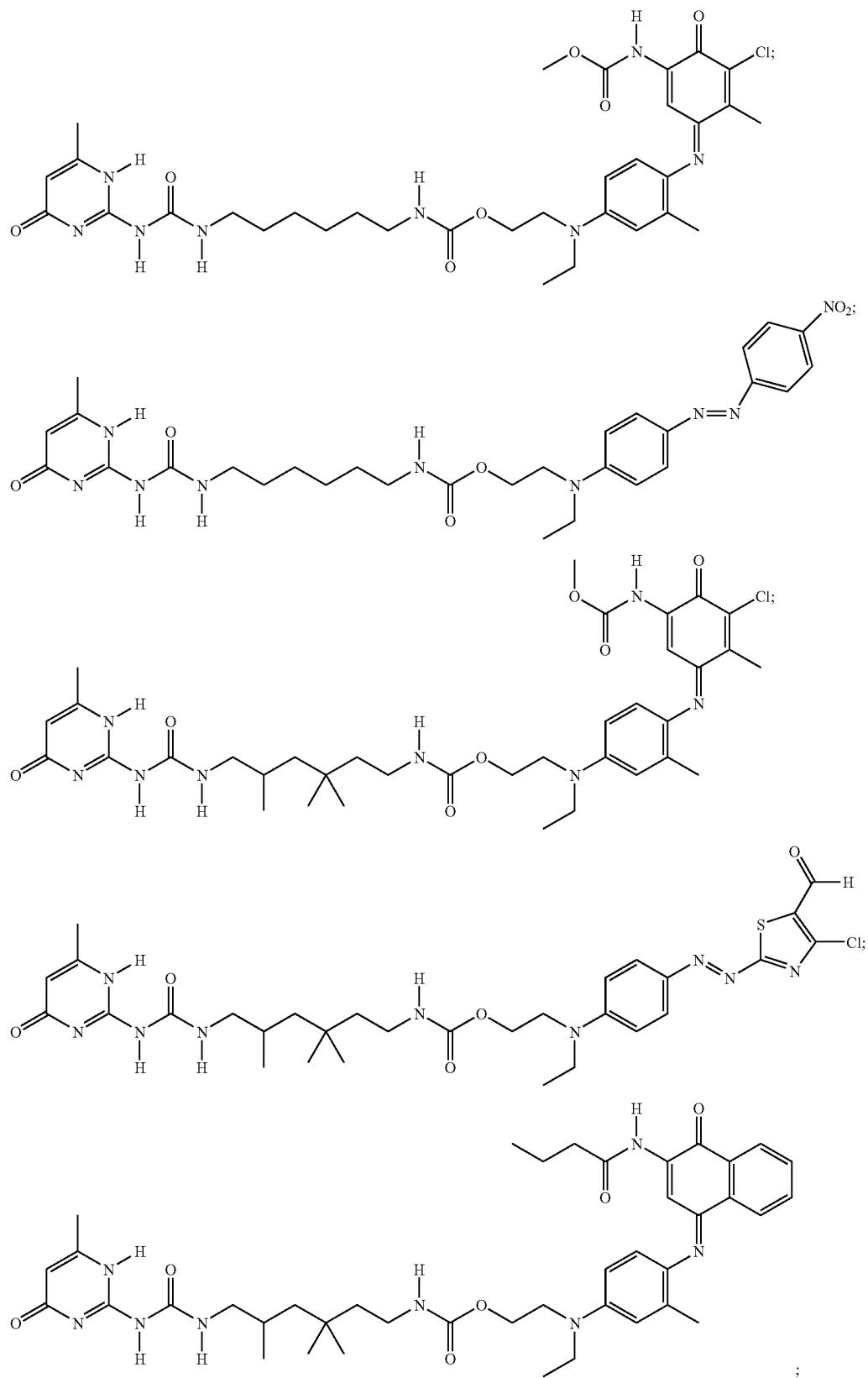

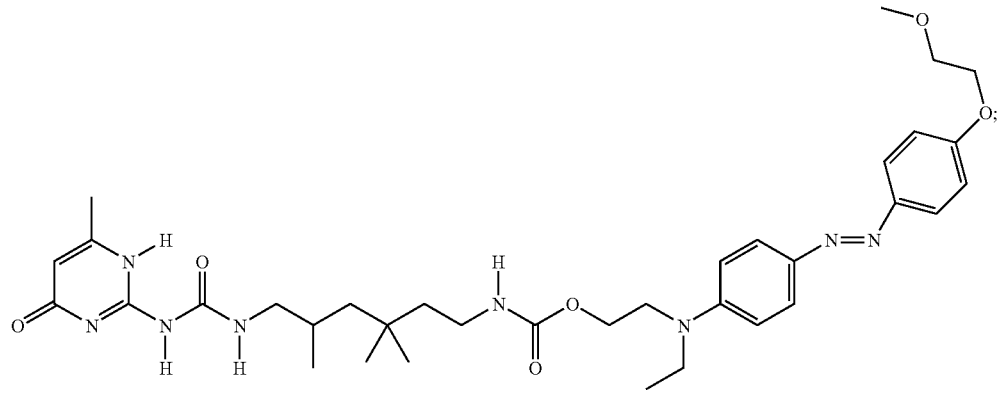
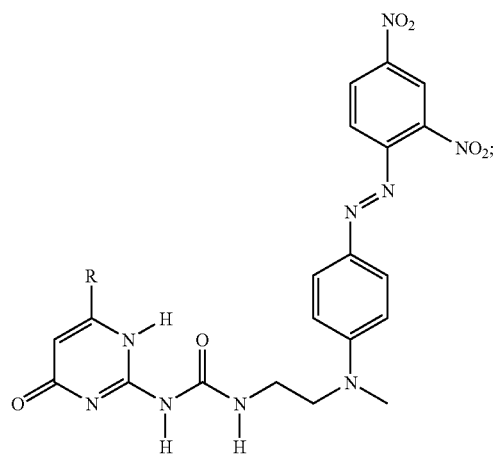
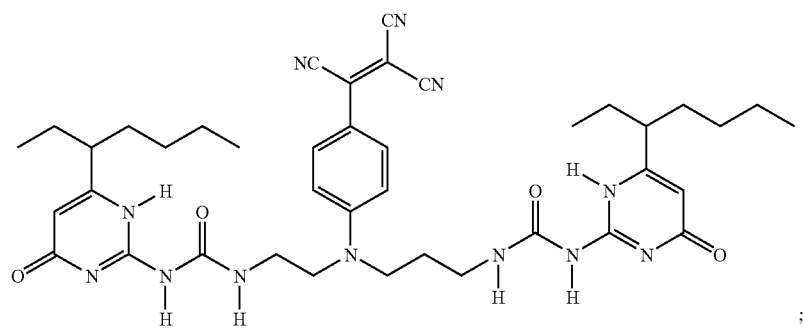

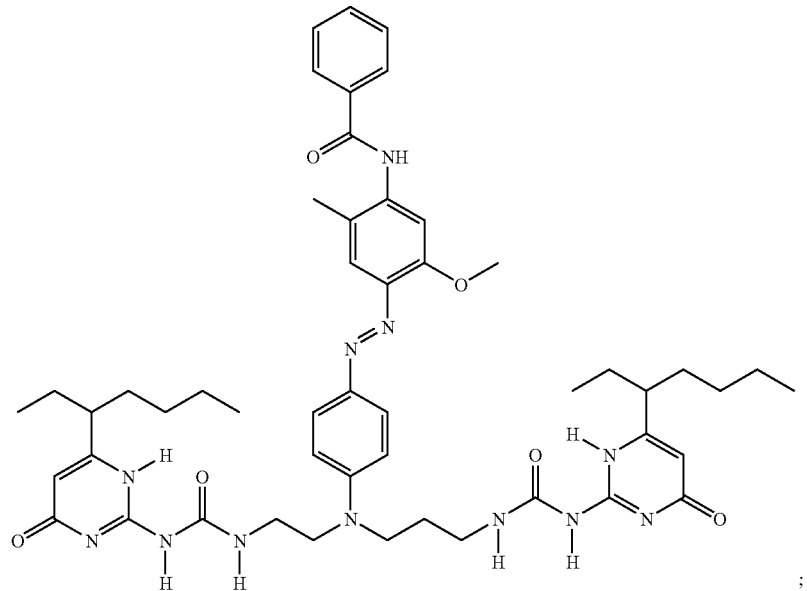
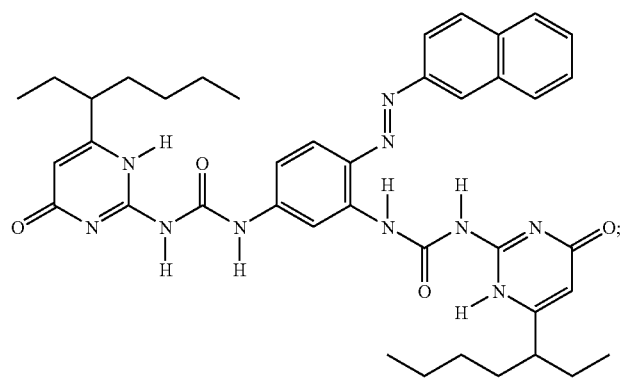
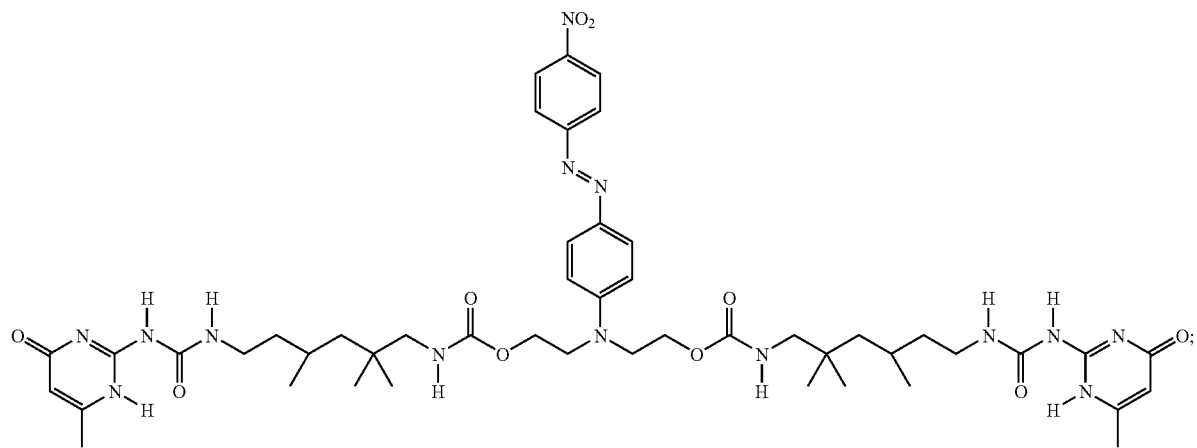

-continued
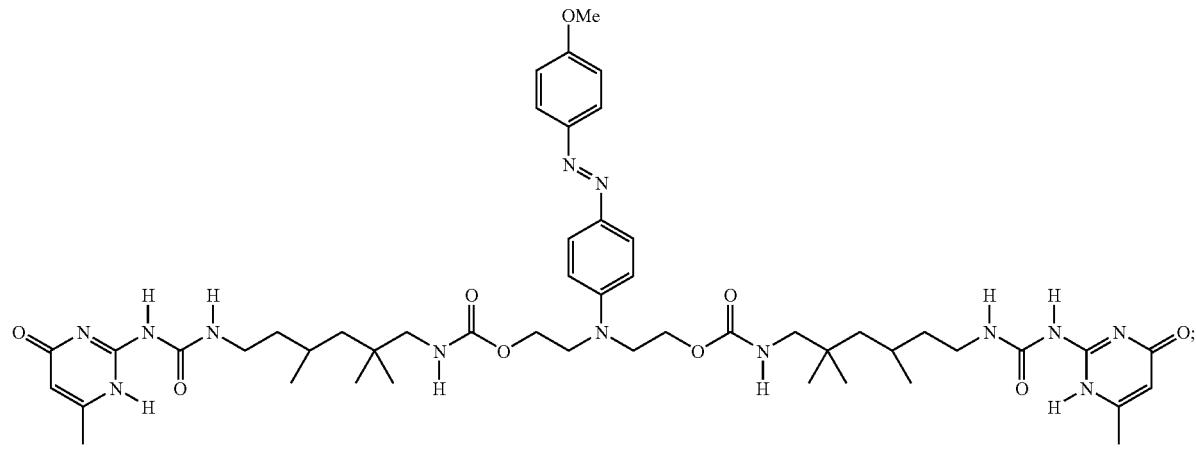
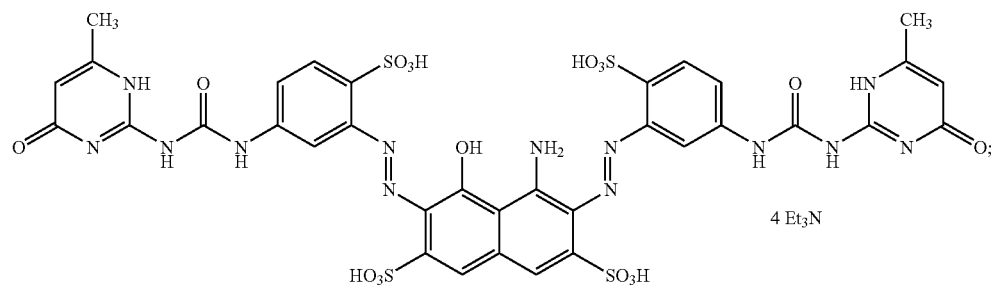
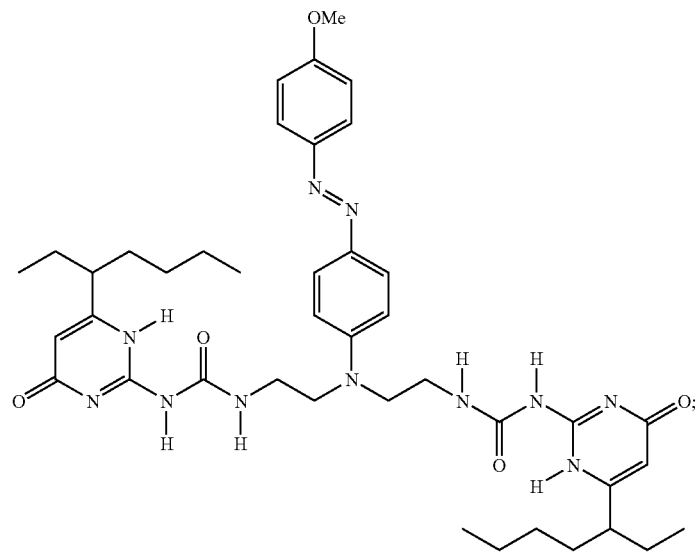

-continued
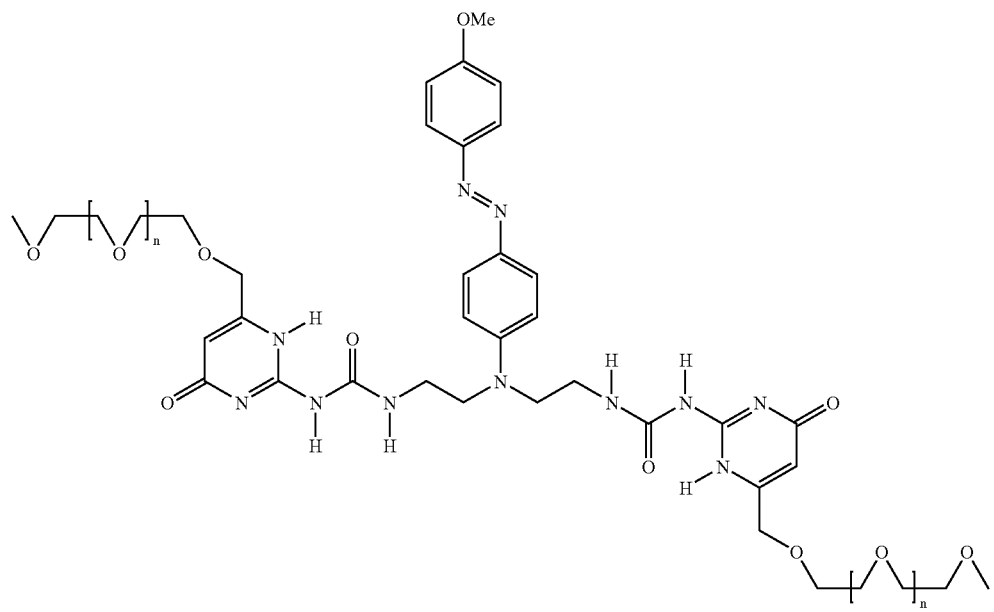
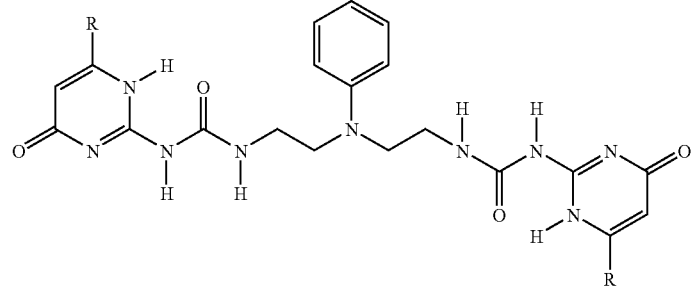 with R = ;
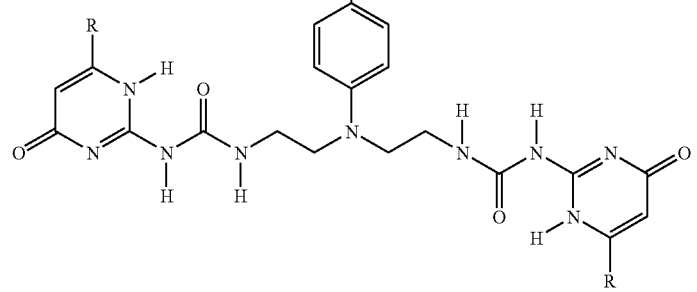 with R = ;

-continued
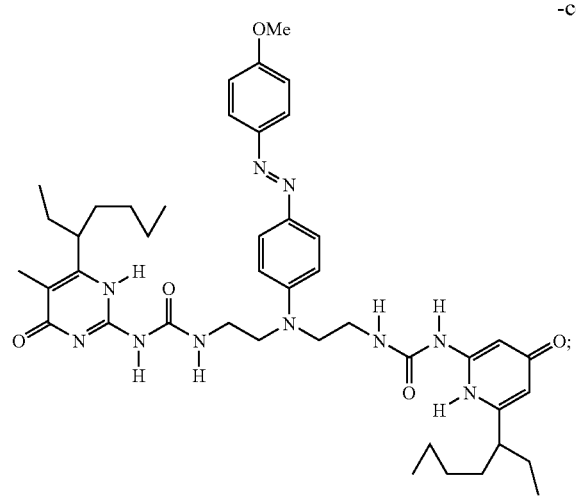
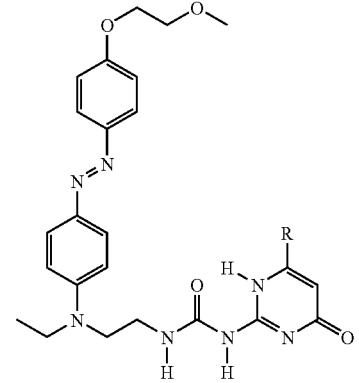
with R = 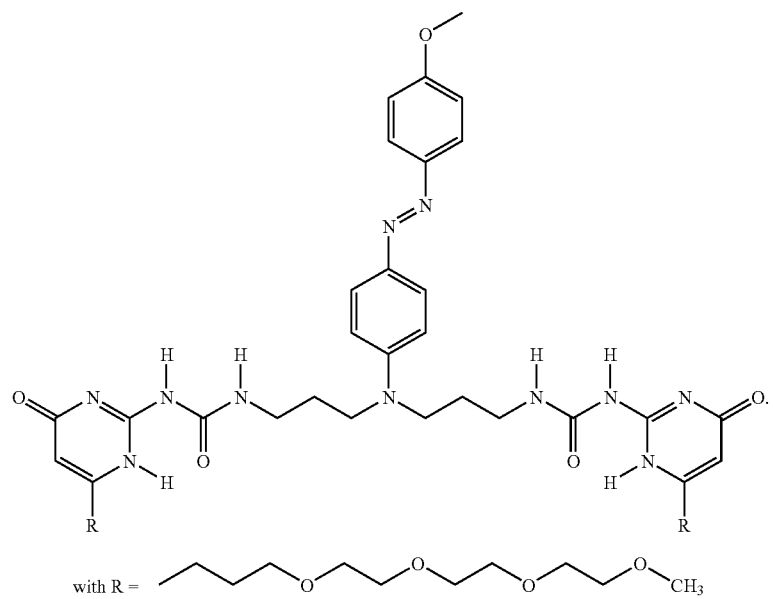; and
with R = propyl-O-CH2CH2-O-CH2CH2-O-CH2CH2-O-CH3
* * * * *